United States Patent
Johnson et al.

(10) Patent No.: US 9,458,488 B2
(45) Date of Patent: Oct. 4, 2016

(54) POINT OF CARE SENSOR SYSTEMS

(71) Applicant: Nanomix, Inc., Emeryville, CA (US)

(72) Inventors: Bradley N. Johnson, Berkeley, CA (US); Jui-Ming Yang, El Cerrito, CA (US); Kanchan A. Joshi, Carlsbad, CA (US); Ray R. Radtkey, Oakland, CA (US); Garrett Gruener, Berkeley, CA (US); Sergei Skarupo, Berkeley, CA (US)

(73) Assignee: Nanomix, Inc., Emeryville, CA (US)

( * ) Notice: Subject to any disclaimer, the term of this patent is extended or adjusted under 35 U.S.C. 154(b) by 686 days.

(21) Appl. No.: 13/844,334

(22) Filed: Mar. 15, 2013

(65) Prior Publication Data

US 2014/0273187 A1    Sep. 18, 2014

(51) Int. Cl.
*G01N 27/416* (2006.01)
*C12Q 1/00* (2006.01)
*G01N 33/543* (2006.01)
(Continued)

(52) U.S. Cl.
CPC ......... *C12Q 1/001* (2013.01); *B01L 3/502738* (2013.01); *G01N 27/4163* (2013.01); *G01N 33/492* (2013.01); *G01N 33/5438* (2013.01); *B01L 2200/04* (2013.01); *B01L 2200/10* (2013.01); *B01L 2300/0645* (2013.01); *B01L 2300/0809* (2013.01); *B01L 2400/0487* (2013.01); *B01L 2400/0633* (2013.01); *G01N 27/27* (2013.01); *G01N 35/1079* (2013.01);
(Continued)

(58) Field of Classification Search
CPC .......................... G01N 33/49–33/4925; G01N 27/327–27/3274; G01N 27/4163; A61B 5/14532–5/14542; A61B 5/1468–5/1477; A61B 5/1486–5/14865; C12Q 1/00–1/006; B01L 3/5027–3/502715
See application file for complete search history.

(56) References Cited

U.S. PATENT DOCUMENTS 6,893,552 B1   5/2005  Wang et al.
2004/0189311 A1*  9/2004  Glezer ............... B01L 3/5027
                                                           324/444
(Continued)

FOREIGN PATENT DOCUMENTS

WO         99/62918      12/1999
WO       2009/042631      4/2009
(Continued)

OTHER PUBLICATIONS

International Search Report and Written Opinion, dated Jul. 7, 2014, issued in Application No. PCT/US2014/029162.
(Continued)

*Primary Examiner* — J. Christopher Ball
(74) *Attorney, Agent, or Firm* — Weaver Austin Villeneuve & Sampson LLP

(57) ABSTRACT

Provided are point of care sensor systems that include portable readers and disposable cartridges for receiving and analyzing samples. A cartridge may be equipped with one or more sensor channels, each containing one or more sensors. After providing a sample to a cartridge, the cartridge can be inserted into a reader, which can interact with the cartridge to perform on-cartridge sensing and receive signals indicating the presence and/or quantity of one or more targets in the sample. Examples of cartridges can include cardiac panels, sepsis panels and the like. In some embodiments, the same sensor hardware may be configured for multiple measurements of different targets conducted at different time frames. Also provided herein are novel on-cartridge solid and liquid reagent storage and delivery mechanisms.

65 Claims, 36 Drawing Sheets

(51) Int. Cl.
  *B01L 3/00* (2006.01)
  *G01N 33/49* (2006.01)
  *G01N 35/10* (2006.01)
  *G01N 27/27* (2006.01)

(52) U.S. Cl.
  CPC ............... *G01N 2035/1018* (2013.01); *G01N 2035/1034* (2013.01)

(56) References Cited

U.S. PATENT DOCUMENTS

| | | |
|---|---|---|
| 2006/0040311 A1 | 2/2006 | Thomas et al. |
| 2006/0264783 A1 | 11/2006 | Holmes et al. |
| 2006/0275852 A1 | 12/2006 | Montagu et al. |
| 2007/0081920 A1 | 4/2007 | Murphy et al. |
| 2010/0075311 A1 | 3/2010 | Barrault et al. |
| 2010/0076287 A1 | 3/2010 | Feldman et al. |
| 2010/0267063 A1 | 10/2010 | Billadeau et al. |
| 2011/0213229 A1 | 9/2011 | Benoit |
| 2012/0190589 A1 | 7/2012 | Anderson et al. |
| 2012/0305409 A1 | 12/2012 | Davis et al. |
| 2014/0138260 A1 | 5/2014 | Briman |
| 2015/0060272 A1 | 3/2015 | Blidner et al. |

FOREIGN PATENT DOCUMENTS

| | | |
|---|---|---|
| WO | 2013/015822 | 1/2013 |
| WO | 2013/117681 | 8/2013 |

OTHER PUBLICATIONS

European Supplemental Search Report issued on Aug. 16, 2016, in Application No. 14762982.8.

* cited by examiner

POINT OF CARE SENSOR SYSTEMS

BACKGROUND

In vitro diagnostic (IVD) tests are becoming more used in modern health care. These tests are performed using devices that analyze specimens drawn from patients. Unlike in vivo diagnostic tests, IVD tests are generally performed in a controlled environment outside a living organism. Blood and tissue specimens can be derived from a subject to identify information concerning a physiological or pathological state. Examples of IVD tests can include tests for glucose, liver enzymes, electrolytes, and tests for illegal and legal drugs.

Conventional IVD equipment can be complex, requiring specialized training, and heavy. As such, these tests are generally run in hospital pathology laboratories. IVD equipment is generally not suitable for use in medical offices or field use by medical professionals, such as during emergency responses, and by patients themselves. Point of care uses of conventional IVD equipment are limited.

SUMMARY

Provided are point of care sensor systems that include portable readers and disposable cartridges for receiving and analyzing samples. A cartridge may be equipped with one or more sensor channels, each containing one or more sensors. After providing a sample to a cartridge, the cartridge can be inserted into a reader, which can interact with the cartridge to perform on-cartridge sensing and receive signals indicating the presence and/or quantity of one or more targets in the sample. Examples of cartridges can include cardiac panels, sepsis panels and the like. In some embodiments, the same sensor hardware may be configured for multiple measurements of different targets conducted at different time frames. Also provided herein are novel on-cartridge reagent storage and delivery mechanisms. For example, a sample may be mixed with one or more lyophilized reagents, such as a lyophilized reporter, which may be provided as part of a cartridge. Aspects of the description herein include cartridges, systems, and methods that provide dissolution and mixing of lyophilized reagents in a sample, ensuring repeatable and precise measurements. Liquid reagents, such as wash or substrate liquids, may also be provided as part of the cartridge in sealed bags. The bags can be pierced during operation with the reagents delivered to a sensor channel or other location. In some embodiments, bubble removal and detection mechanisms are provided to increase sensor reliability and reproducibility. In some embodiments, the systems can include low thermal mass screen printed heaters configured to maintain a sensor channel at a desired temperature.

One aspect of the disclosure relates to cartridges for sensing analytes in a sample. The cartridge can include a sample inlet chamber for receiving a sample and one or more sensors configured to detect analytes in the sample. The cartridge can further include a solid phase reagent chambers and/or a puncture-able compartment containing liquid reagent. In the some implementations, the cartridge can further include a mixing circuit connected to the sample inlet chamber and comprising a mixing chamber and the solid phase reagent chamber. In some implementations, the cartridge can further include de-bubbling channel disposed between the sample inlet chamber and the detection channel and configured to vent out bubbles in the sample. The de-bubbling channel may or may not be part of a mixing circuit. In some implementations a buffer zone may be disposed between a solid-phase reagent chamber and the de-bubbling channel. The buffer zone may be part of a mixing circuit. The de-bubbling channel may be covered by a hydrophobic membrane.

The cartridge may optionally include a plasma filter to filter whole blood samples. A vacuum line may be connected to the plasma filter. In some implementations in which the cartridge includes a puncture-able compartment, the cartridge may further include a puncture mechanism configured to puncture the puncture-able compartment. The puncture mechanism may be pneumatically actuated. In some implementations, the cartridge can further include a screen-printed heater configured to heat the detection channel. The cartridge may further include a screen-printed thermocouple configured to provide temperature feedback of the detection channel. The cartridge may further include a sensing assembly including screen-printed electrodes. The one or more sensors can include two or more screen-printed electrodes. The cartridge can be configured to perform electrochemical enzymatic sensing and electrochemical enzyme-linked immunosorbent assay (ELISA) sensing on a single sample. The cartridge can be configured to perform non-capture based electrochemical sensing and capture-based electrochemical sensing on a single sample.

The cartridge may be configured to receive only pneumatic and electric inputs from a reader, with no mechanical actuation or inputs. All liquid movement within the cartridge can be pneumatically actuated. The cartridge can further include a microfluidic layer. The microfluidic layer may be a multi-layer laminate structure. In some implementations, it can include a monolithic membrane. The microfluidic layer can include any of the solid-phase reagent chamber, the mixing chamber, de-bubbling channel, the buffer zone and the detection channel. In some implementations, the cartridge can include a plurality of fluid stops connected to a hydrophobic membrane. In some implementations, the cartridge can include one or more diaphragm valves. The fluid stops and/or diaphragm valves can be part of a microfluidic layer.

Another aspect of the disclosure relates to an electrochemical sensor assembly including a cartridge and a reader configured to receive the cartridge, the reader configured to provide a plurality of pneumatic inputs to the cartridge and receive electric signals from the cartridge indicating detection information of two or more target analytes in a sample. The cartridge can include a sample inlet port, one or more solid reagent compartments, one or more liquid reagent compartments, and a sensor well including two or sensors configured to detect biomolecules in the sample. Fluid movement in the cartridge may be pneumatically actuated via the plurality of pneumatic inputs. In some implementations, the reader can be configured to supply vacuum at a set level Pv and pressure at a set level Pp, wherein Pp is greater than Pv. The reader can include a single motor single head pump, a first check valve on a first side of the pump and a second check valve on the second side of the pump, the first check valve having a cracking pressure of Pv and the second check valve having a cracking pressure of Pp.

Another aspect of the disclosure relates to a reader configured to receive a cartridge, the reader including a pneumatic assembly configured to supply vacuum to the cartridge, at a set level Pv and pressure at a set level Pp, wherein Pp is greater than Pv. The reader may also include a detection assembly configured to and receive electrical signal information from the cartridge. The pneumatic assembly may include a single motor single head pump, a first check valve on a first side of the pump and a second checking valve on the second side of the pump, the first check valve having a cracking pressure of Pv and the second check valve having a cracking pressure of Pp. In some implementations, a reader may be configured to identify at least two assays associated with the cartridge, and apply first and second measurement voltages, the first measurement voltage associated with a first assay and the second measurement voltage associated with the second assay, wherein the second measurement voltage is applied after the first measurement voltage. The first and second measurement voltages may be applied to the same or different electrodes on the cartridge. The reader may be configured to detect the presence of bubbles on an electrode on the cartridge.

Another aspect of the disclosure relates to a cartridge for sensing first and second target analytes in a biological sample, including a first working electrode coated with one or more enzymes configured to react with a first target analyte to directly or indirectly produce a first electrochemical signal and a second working electrode having capture species attached thereto, the capture species configured to capture the second target analyte to directly or indirectly produce a second electrochemical signal, wherein the cartridge is a single sample, single use, disposable cartridge.

Another aspect of the disclosure relates to a method of detecting two or more analytes in sample, the method including receiving, with a reader, a cartridge including the sample; delivering the sample to a sample well on the cartridge; applying a first measurement voltage to one or more sensors on the cartridge; measuring a first electrochemical signal from one of the one or more sensors; determining the presence, absence, or amount of a first target species in the sample based on the first electrochemical signal; applying a second measurement voltage to one or more sensors on the cartridge; measuring a second electrochemical signal from one of the one or more sensors; and determining the presence, absence, or amount of a second target species in the sample based on the second electrochemical signal.

Another aspect of the disclosure relates to a reader configured to detect bubbles on a sensor of a cartridge, the reader including an interface for receiving the cartridge; computer readable media including instructions to measure the impedance of a sensor well on the cartridge; determine the series resistance Rs and the series capacitance Cs of an equivalent circuit; determine if a relationship between series resistance Rs and the series capacitance Cs meets a specified criteria; and based on the determination of the relationship, determine whether a bubble is detected.

Another aspect of the disclosure relates to chemical sensor cartridge including a cartridge casing; a pouch containing a liquid reagent disposed in a first location the casing; a pneumatically actuate-able puncture mechanism disposed in the casing, the pneumatically actuate-able puncture mechanism including a spike disposed in a cavity having an opening onto the first location. In some implementations, the puncture mechanism includes a deformable membrane configured to push the spike toward the pouch when the mechanism is pneumatically actuated. In some implementations, the puncture mechanism includes a vacuum line configured to draw the pouch onto the spike.

Another aspect of the disclosure relates to a cartridge for sensing one or more analytes in a sample including a sample inlet port configured to receive a sample; a sensor well including one or more sensors; and a de-bubbling channel disposed between the reagent chamber and the sensor well and configured to vent out bubbles in the sample.

Examples of samples that may be used with the methods and devices described herein include blood, urine, saliva, cerebrospinal fluid, and milk. These and other aspects are described are described further below with reference to the figures.

DETAILED DESCRIPTION OF EXAMPLE EMBODIMENTS

Figure 1A:
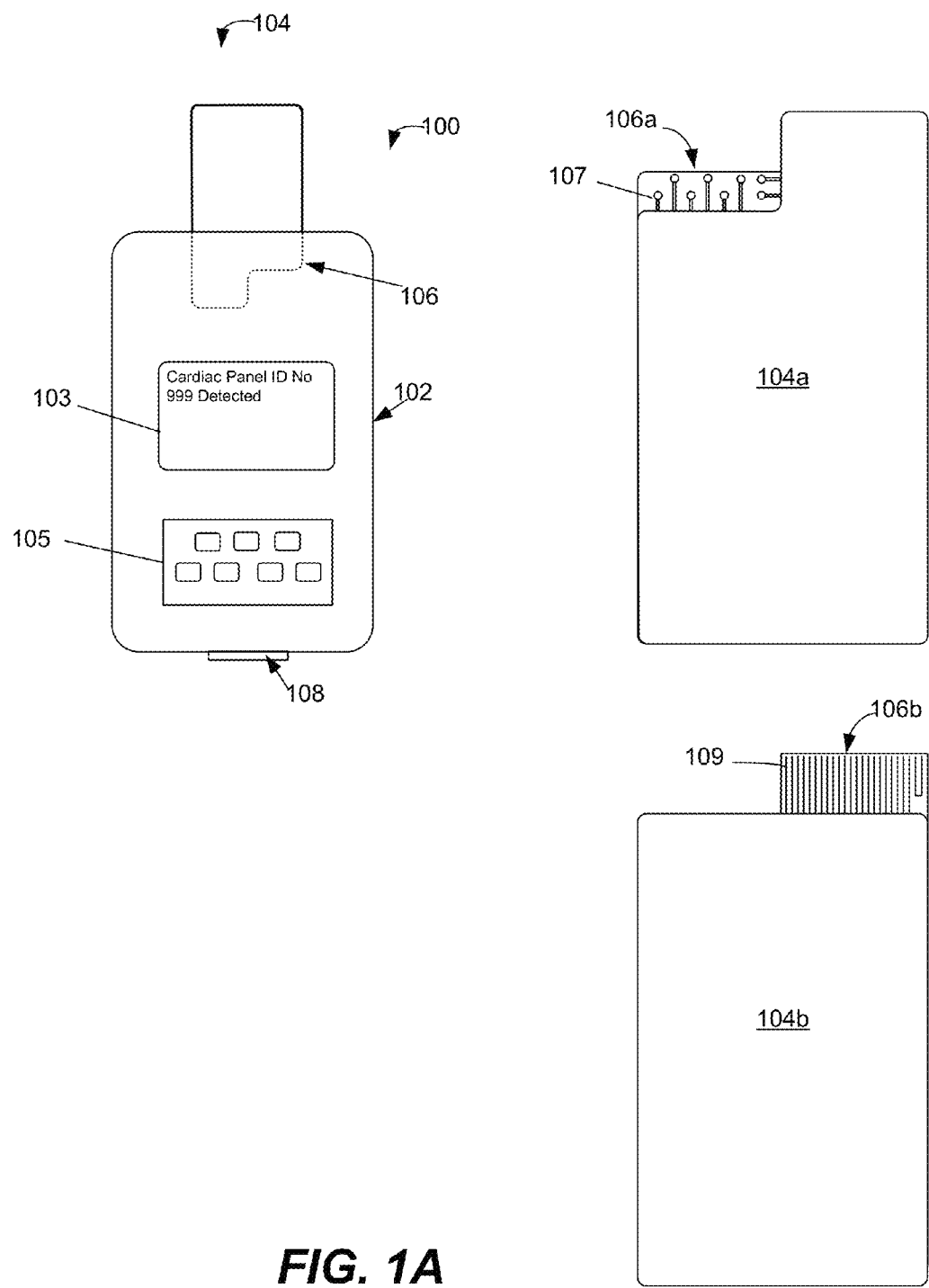
FIG. 1A is an example of a simplified schematic showing an example of a point-of care system, including a reader and a cartridge that can be inserted into the reader.

In the following description, numerous specific details are set forth to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Point-of-care testing is performed at or near the site of patient care. The driving notion behind this approach is to bring the test conveniently and immediately to the patient. This increases the likelihood that the patient and medical professional receive results quicker and make more immediate clinical management decisions. Some examples of point-of-care testing include blood glucose testing, blood gas and electrolytes analysis, rapid coagulation testing, rapid cardiac markers diagnostics, rapid sepsis markers diagnostics, drug abuse screening, urine strip testing, pregnancy testing, fecal occult blood analysis, food pathogen screening, hemoglobin diagnostics, infectious disease testing and cholesterol screening.

Point-of-care testing may be accomplished using portable instruments and/or test kits. Small bench analyzers or other fixed equipment are often used because portable devices are not available for many types of tests. The goal of point-of-care testing is to collect specimens and obtain results quickly at or near the location of the patient so that the treatment plan can be adjusted as necessary before the patient leaves or condition worsens. Point-of-care testing instruments can allow for more rapid decision making and triage, reduce operating times, reduce high-dependency, postoperative care time, reduce emergency room time, reduce the number of outpatient clinic visits, reduce the number of hospital beds required, and ensure optimal use of professional time.

The portable instruments described herein for point-of-care testing are relatively simple to accommodate a wide range of medical professionals, non-professional administrators and even patients. They are sufficiently robust and can withstand transportation, changes in temperatures, mechanical stresses, and other environmental impacts typically associated with portable devices. For example, in some implementations, the portable point-of-care testing instruments described herein may be used in moving emergency vehicles (such, as ambulances, helicopters), military missions, and other like environments. Additionally, in some implementations, a variety of tests are supported by one portable instrument. This can be advantageous as many point-of-care environments cannot support multiple instruments. In some implementations, the portable point-of-care testing instruments are configured to provide fast responses and perform multiple parallel tests on a single sample. The systems also provide precise measurement in a cost-effective manner. In some implementations, the systems provided herein allow for point-of-care assays that are stable at room temperature and have high sensitivity. The systems can provide the same or better performance as plate-reader systems using refrigerated liquid reagents.

Aspects described herein include on-cartridge sample delivery, reagent storage and delivery, bubble detection and elimination, temperature control as well as mechanically robust and simple readers. These and other aspects are described below in the context of examples of point-of-care systems. FIG. 1A is a simplified schematic showing an example of a point-of care system 100, including a reader 102 and a cartridge 104 inserted in the reader 102. In use, blood or other fluid to be analyzed is placed in the cartridge 104, with the cartridge 104 then placed in the reader 102. In some implementations, the sample and other fluids are moved through the cartridge solely by application of pressure and/or vacuum. This can eliminate the use of mechanical solenoids and other complex non-pneumatic actuators. As a result, the reader 102 may be configured to interface with only a small portion 106 of the cartridge 104, for example to provide an electrical interface to sensor electrodes and vacuum and/or pressure lines to move fluids and open/close valves. As described further below, the sample can be mixed with a reporter and delivered to one or more electrochemical sensors for analysis. Signals from the electrochemical sensors can be read and stored by the reader 102. In some implementations, the systems can be used to perform enzyme linked immunosorbent assays (ELISA) or other ligand binding assays that detect substances in a liquid sample. In some implementations, the systems can be used to performed enzymatic assays such as glucose sensing.

The reader 102 may include a pneumatic system including one or more pumps to provide vacuum and pressure to the cartridge and software and hardware to control the assay and read the results. These components can be housed within a sturdy, impact resistant polymer casing. The reader 102 may further include an interface 108 to connect to a computer system. User interface features of the reader 102 can include a display 103 and keyboard 105. In some implementations, the reader can be configured to handheld, e.g., with a single hand of an operator. In some implementations, the reader may include a handle portion configured for easy handling during operation. Example masses of the reader 102 can be around 500 g-1200 g, e.g. 900 g. Example volumes of the reader can be around 1000 cm$^2$-2500 cm$^2$, with dimensions on the order 5 cm-25 cm. In one example, a reader can be around 18 cm×13 cm×5 cm.

FIG. 1A also shows examples of interface portions 106*a* and 106*b* of first and second sides a104*a* and 104*b* of cartridge 104. First side 104*a* includes interface portion 106*a*, which includes pneumatic ports 107 configured to connect to pneumatic lines in the reader 102 and provide vacuum, pressure and/or ambient to the cartridge 104. In the example of FIG. 1A, eight ports 107 are depicted, though fewer or more may be used according to the particular implementation. Interface portion 106*b* includes conductive traces 109.

Figure 1B:
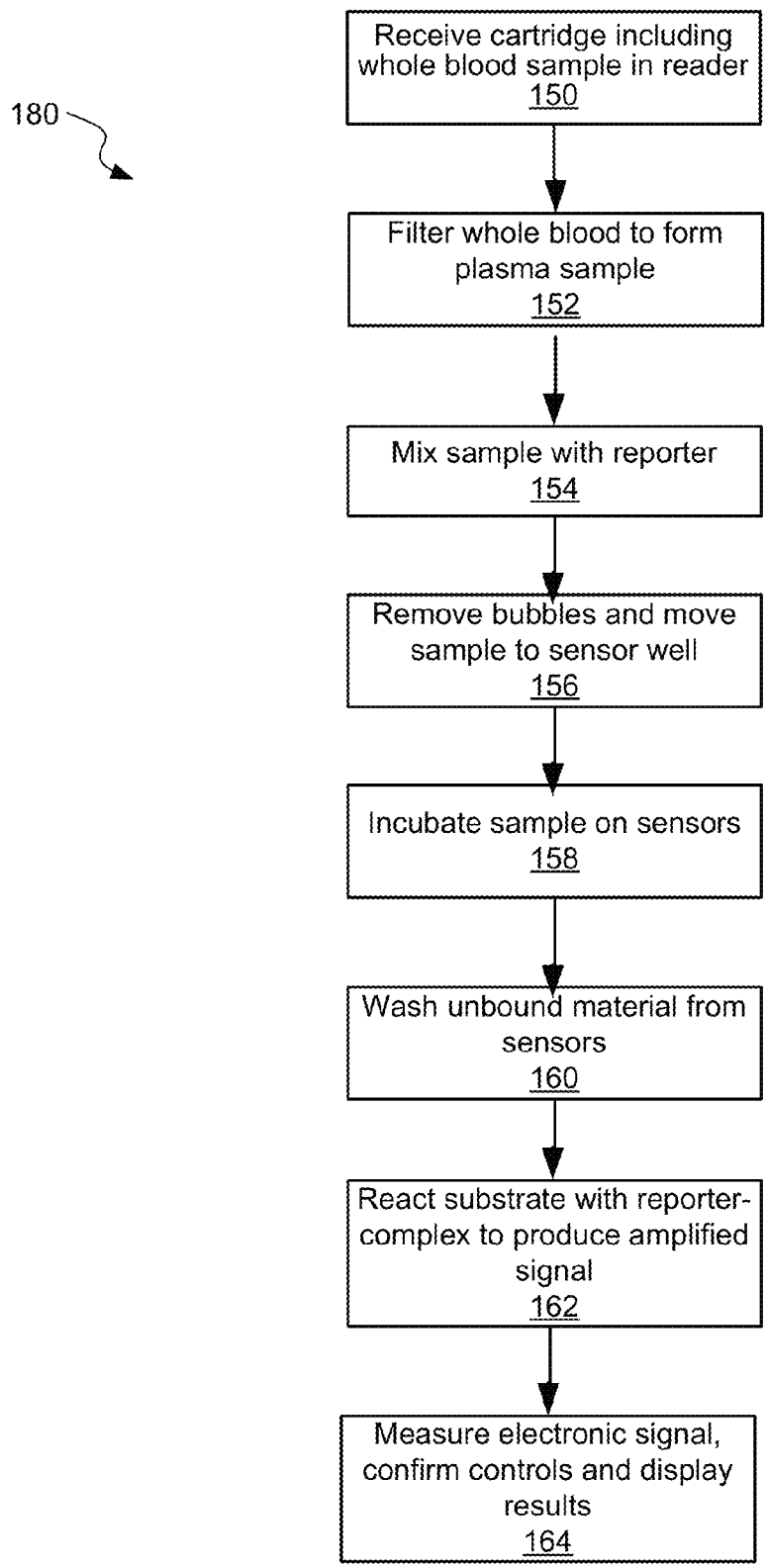
FIGS. 1B-1D show example process flows for electrochemical ELISA and enzymatic assays that may be implemented using the systems described herein.
Figure 1C:
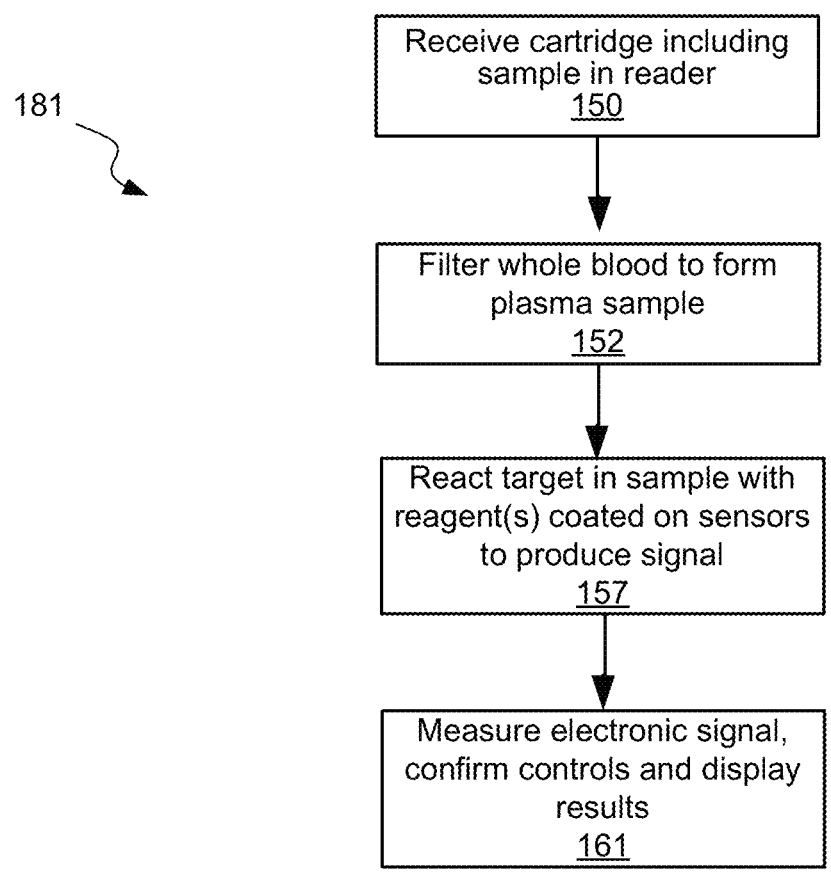

The cartridges and readers described herein may be used for various assay types and modalities, including but not limited to, electrochemical enzyme-linked immunosorbent assays (ELISA) and enzymatic assays such as assays for glucose or lactate levels. As described further below, in some implementations, multiplexed testing of a single sample for multiple analytes may be performed using a single cartridge. FIGS. 1B and 1C show example process flows for electrochemical ELISA and enzymatic assays that may be implemented using the systems described herein.

FIG. 1B is a process flow 180 showing certain operations in an electrochemical sandwich ELISA assay using a whole blood sample according to certain implementations. After receiving the sample, all of the operations in FIG. 1B may be performed on-cartridge, with the reader controlling all on-cartridge operations. First, a cartridge including a whole blood sample is received in the cartridge (block 150). Prior to block 150, a whole blood sample may be transferred to the cartridge via a sample inlet port. In some implementations, the transfer device and/or an on-cartridge port or compartment that receives the sample is sized to obtain a specified quantity of whole blood that will provide that will provide a certain amount of plasma. The clinician or other user turn the reader on and insert the cartridge into the reader. The reader can be configured to automatically turn on when a cartridge is inserted. In some implementations, the reader may identify the type of assay the cartridge is designed for and ask the user to confirm that this is the desired assay. In certain implementations in which the reader is designed to work with different types of cartridges and/or samples, the reader may further identify the type of cartridge and/or sample and ask the user for confirmation. Next, the whole blood is filtered to form a plasma sample (block 152). One or more target species to be assayed may be present in the plasma sample. As described further below, pneumatics draw the plasma through the filter in certain implementations. The sample then mixes with a reporter compound stored on-cartridge (block 154). Storage of thermostable reporters (or other bioreagents) and subsequent mixing can be challenging outside of a laboratory environment. Aspects of the systems and methods described herein address these challenges, providing precise quantities of reporter and sample. Bubbles are then removed from the sample and the sample is moved to the sensor well (also referred to as a sensor channel, detection channel, or sensor chamber). (Block 156). The presence of bubbles in a sample can significantly affect assay precision. Aspects of the systems and methods described herein provide precise results by reducing or eliminating bubbles. Also provided are bubble detection and calibration. The sample is then incubated on one or more sensors in the sensor well (Block 158). This binds reporter-target complexes to capture species on each of the sensors. In certain implementations, electrochemical sensors including nanostructured electrodes are provided. For example, carbon nanotube (CNT)-based electrochemical sensors can include, for example, networks of CNT's as high surface area working electrodes and can provide highly sensitive detection. In some implementations, nanostructured electrodes allow a relatively small amount of sample and reagents to be used for multiple sensors, facilitating on-cartridge reagent storage and portable readers and point-of-care systems. Unbound materials are then washed. (Block 160). In certain implementations, wash liquid stored on-cartridge is flowed over the sensor well after a set incubation time. A substrate is then reacted with the bound reporter complex to produce one or more amplified signals. (Block 162). Electrochemical reduction of the reporter complex generating a current in proportion to the amount of target present such that an amplified signal indicates the amount of target present. The reader measures the electronic signal(s), and after confirming controls, displays the results of the assay (164). The reader can converted the electronic signal to clinical units for display.

FIG. 1C is a process flow 181 showing certain operations in an electrochemical enzymatic assay using a sample according to certain implementations. Blocks 150 and 152 can be performed as described above with respect to FIG. 1B. Once the sample is moved into the sensor well, a target analyte in the sample is then reacted with one or more reagents (e.g., one or enzymes and/or mediators) on a sensor to produce an electrochemical signal indicating the amount of target present. (157). The reader measures the electronic signal(s), and after confirming controls, displays the results of the assay (161). The reader can converted the electronic signal to clinical units for display. Unlike the ELISA assay described with respect to FIG. 1B, the enzymatic assays generally do not involve a binding reaction with a capture species bound to the sensor. Moreover, if performed, an enzymatic assay can occur at a different time scale than the ELISA assay described above, such the electronic signal produced in block 157 is produced prior to that in block 162 described above. In some implementations, a cartridge is configured for both enzymatic and ELISA assays. According to various implementations, running a single cartridge can involve performing only one or both of methods 180 and 181. If both enzymatic and ELISA assays are performed, they can occur in the same or parallel sensor wells.

While aspects of the cartridge and reader and related systems and methods are described below in the context of an electrochemical ELISA assay and/or electrochemical enzymatic assay such as that described in FIGS. 1B and 1C, they are not so limited. For example, aspects described herein may be implemented in cartridges and other microfluidic environments, including on-cartridge storage of lyophilized reporters and other bioreagents as well as liquid reagents. In another example, aspects described herein may be implemented in mixing of solid compounds with liquids in a cartridge or other microfluidic environment. In another example, aspects described herein may be implemented with on-cartridge movement of liquids for other types of assays or other on-cartridge processes. In yet another example, aspects described herein may be implemented for on-cartridge bubble detection and bubble removal. In another example, aspects of the disclosure may be implemented for on-cartridge release and control of stored liquids. Aspects described herein may be implemented with other types of ELISA assays, as well as other types of electrochemical assays, non-ELISA assays, and non-electrochemical assays. For example, aspects described herein may be implemented in an enzymatic assay employing optical detection. For example, a cartridge may be configured for electrochemical ELISA as well as optical detection employed in an enzymatic assay. Moreover, aspects of the disclosure may be implemented in any on-cartridge or on-chip context, including biochip, lab-on-a-chip, and microfluidic cell culture chip contexts.

Figure 2A:
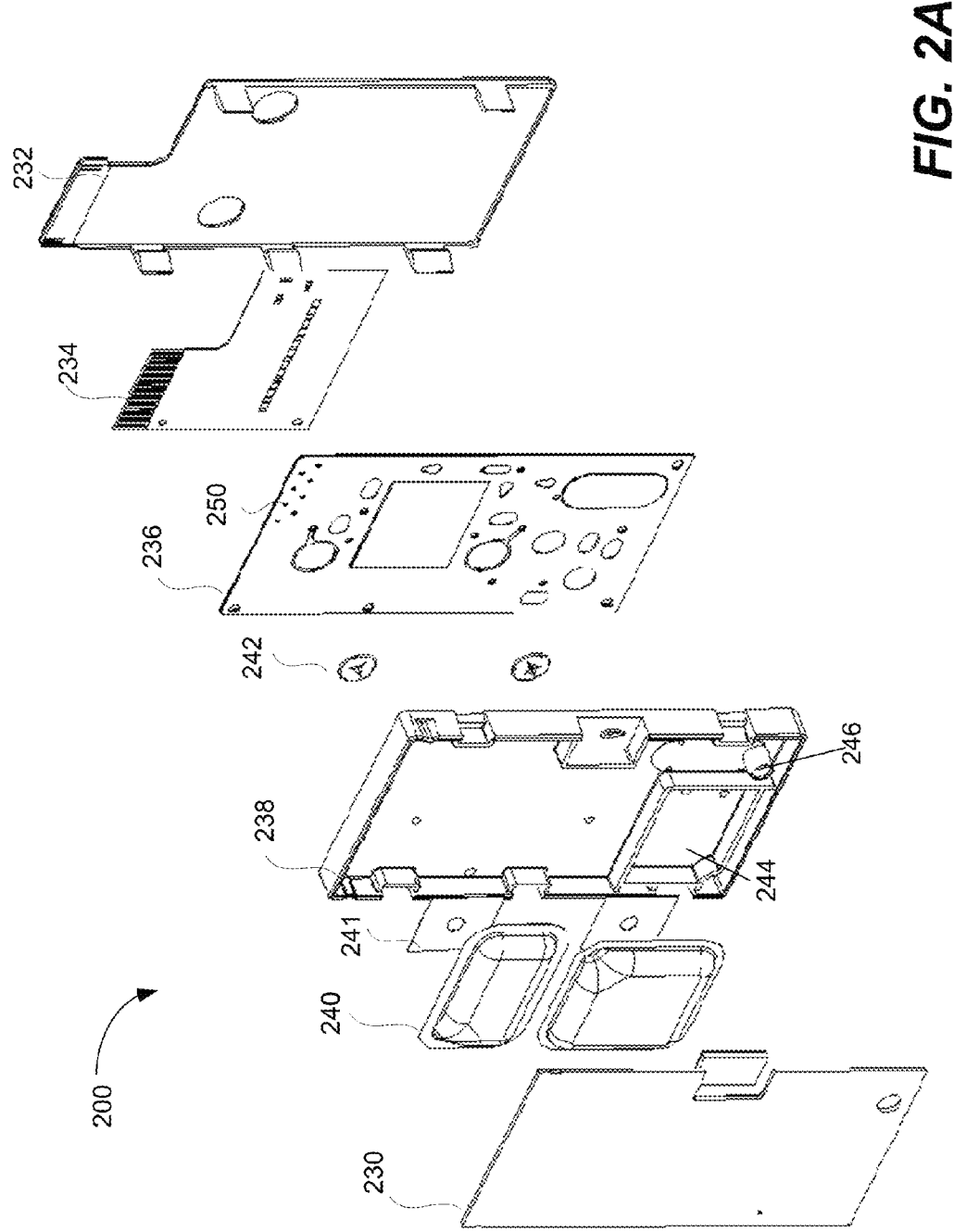
FIG. 2A is an example of a schematic representation of an exploded view of a cartridge, in accordance with certain embodiments.

FIG. 2A is a schematic representation of a cartridge 200, in accordance with certain implementations. Components of cartridge 200 include top and bottom plates 230 and 232, respectively, sensor assembly 234, microfluidic layer 236, airline plate 238 and reagent pouches 240. The components may be arranged in a plastic body including top plate 230, bottom plate 232 and airline plate 238, which may be formed from multiple different parts assembled together. Each part may be individually molded during fabrication of cartridge 200 followed by assembly of these parts. The components of cartridge 200 may be formed during these molding operations and/or assembly operations. The plastic body may be any thermally stable, chemically inert plastic. Some of the components of the cartridge 200 may be made from materials that are different than plastic body 202.

The cartridge 200 may further include a microfluidic layer 236, which includes pneumatic channels and microvalves and microfluidic channels and chambers. The microfluidic layer is discussed further below with respect to FIGS. 2A, 2B and 4A-4H. Airline plate 238 provides connections (not shown) from pneumatic ports 250 to pneumatic channels on the microfluidic layer 236. Airline plate 238 may include a sample inlet port 246 and a waste chamber 244.

The sample inlet port may include an opening and reservoir for at least temporary storage of provided samples. Examples of samples include whole blood, plasma, and urine. Non-biological samples like water and milk can also be used. A sample may be delivered into a sample inlet port using, for example, a dedicated transfer device, a capillary fingerstick, a VACUTAINER™ draw available from Becton Dickinson (BD) in Franklin Lakes, N.J., a syringe, a pipette, or other appropriate instrument. According to various implementations, a sample can be delivered directly from skin puncture or may undergo some processing, such as plasma separation and/or addition of one or more additives, prior to delivery. Moreover, samples are not necessarily limited to blood samples, but may include any fluid sample or sample contained in a fluid appropriate for the assay, including serum, urine, saliva and cerebrospinal fluid (CSF). If the sample is a blood sample, an anti-coagulant may be included in the VACUTAINER or other collection instrument, or the sample may be first transferred from the collection instrument to a transfer device with an anti-coagulant. In some implementations, the cartridge 200 is not pre-loaded with anti-coagulant. In this manner, the cartridge 200 can be configured to be used with collection devices that include anti-coagulants as well as those that do not. In some other implementations, the cartridge 200 may include anti-coagulants. In many implementations, the cartridge does not need to be refrigerated prior to sample addition as it includes only reagents stable at the point-of-care environment.

Figure 2B:
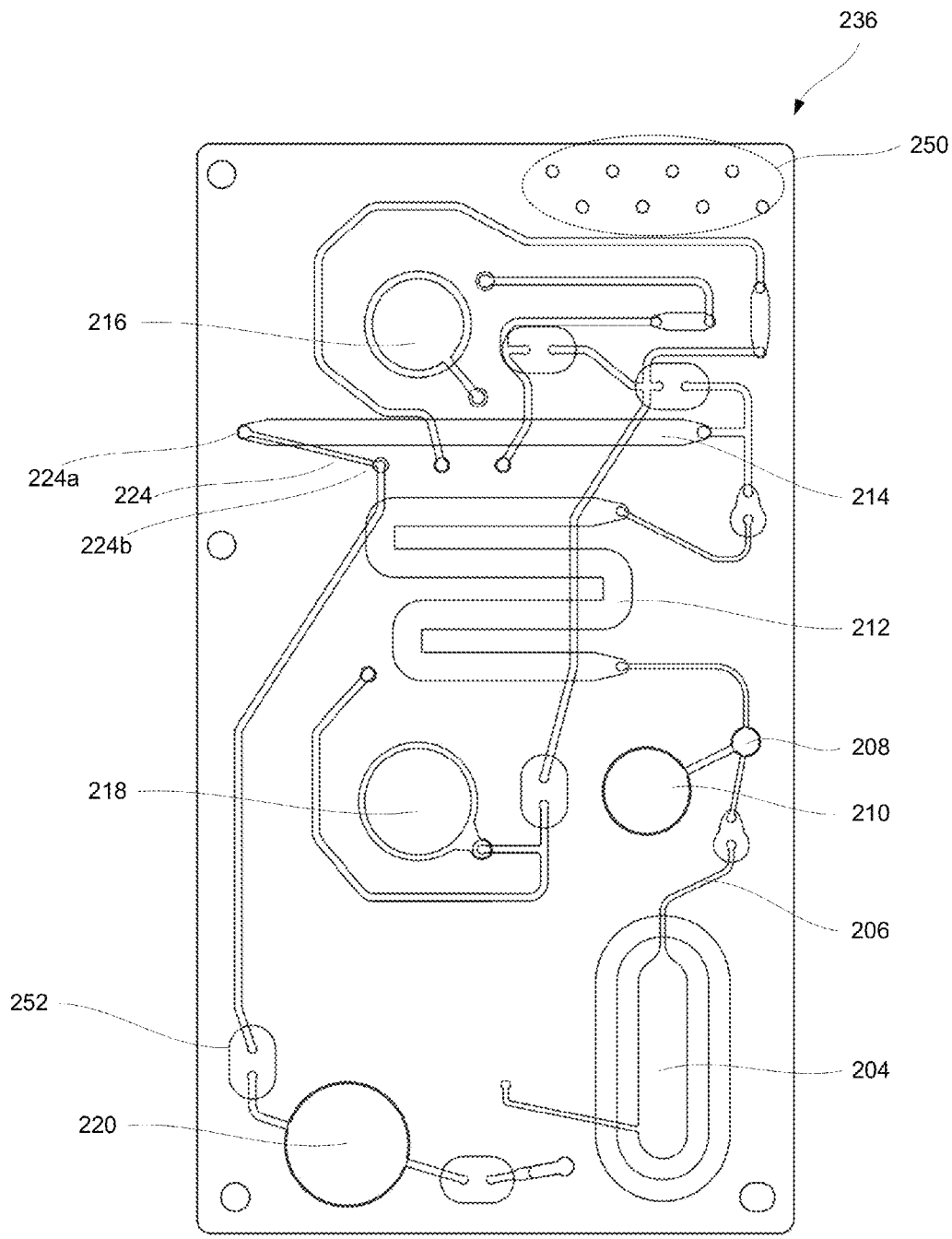
FIGS. 2B-2E are examples of schematic representations of micro-fluidic layers of a cartridge.

FIG. 2B is a schematic representation of micro-fluidic layer 236. It shows various compartments, channels, valves, and other components of microfluidic layer 236. The microfluidic layer 236 is a multilayer microfluidic layer 236, with various components arranged in multiple different levels. Accordingly channels and other components that overlap in FIG. 2B are in different layers and may not intersect or have fluid communication with each other. While detailed descriptions of each layer are provided further below, FIG. 2B provides an example of an arrangement of various components of the microfluidic layer 236 on a cartridge.

A sample chamber 204 may be connected to sample line 206 that pulls the sample from the sample inlet port 204 and into other components of cartridge 200 further described below. When a sample is initially loaded into sample inlet port 204, sample line 206 may be at a reduced pressure relative to the environment (i.e., the pressure at the opening of the sample inlet port). This pressure differential draws the sample from sample inlet port and into sample line 206 for delivery to other components. This pressure differential can depend on the viscosity of sample, the size of the sample line 206, flow rates, and other fluid dynamic considerations. In certain implementations, this pressure differential is between about 1 psi and 7 psi or, for example, between about 3 psi and 5 psi. As described further below, a whole blood may be passed through a filter to separate and create a plasma sample.

From sample line 206, the sample flows into a reporter chamber 208. Reporter chamber 208 may include one or more reporters for mixing with the sample. These reported may be provided in a lyophilized form and may be preinstalled in cartridge 200. Examples of reporters include lyophilized phosphatases and peroxidases such as alkaline phosphatase (AP) and horseradish peroxidase (HRP). Lyophilized reporter compounds, in pellet or other forms, can contain other necessary components such as sugars and excipients in addition to the reporter itself that present a challenge in adequate on-cartridge mixing. For example, once a lyophilized pellet is introduced to sample, it can become a gooey, hard-to-dissolve material. If a reporter is provided in lyophilized pellet form, then a sample may be flown passed this pellet multiple time to ensure adequate dissolution of the reporter and mixing with the sample. The use of lyophilized reporter can permit the system to be stable at room temperature, eliminating the need for refrigeration. In some implementations, magnetic lyophilized beads may be used, separated by mixing as described below.

Reporter chamber 208 is also connected to a mixer 210 and de-bubbling channel 212. The reporter chamber 208 and mixer 210 are part of a mixing circuit that allows flowing sample solution through reporter chamber 208 in both directions, which may be used for dissolving lyophilized pellets provided in reporter chamber 208. This feature is further explained below with reference to FIG. 3. In some implementations, the dimensions of the mixing circuit are sufficient to allow the fluid to fold over during mixing. In some implementations, the system mixes the reporter sufficiently with the sample to provide precise quantities of sample and reporter to the sensor well without the need for sonication, vortexing or other laboratory methods used to dissolve reporters.

De-bubbling channel 212 separates gases from liquid in the sample by passing the sample over one or more hydrophobic membranes that transfers gas but not fluids. Removing gases from a liquid sample enhances sensitivity of probes and generally improves performance of cartridge 200. The de-bubbling channel dimensions can be sized such that the surface tension of the fluid cannot hold the internal pressure of the bubble, forcing the bubble to vent through a hydrophobic membrane. Example dimensions of the de-bubbling channel 212 can be about 1 mil. Example membranes can have porosities of about 0.1 μm and thickness of 1-5 mils. The one or more hydrophobic membranes can overlie the de-bubbling channel.

According to various implementations, the de-bubbling channel 212 may or may not be part of the mixing circuit. In some implementations, de-bubbling channel 212 is part of the mixing circuit. This can prevent bubbles caught in a chamber, such as mixing chamber 208 or reporter chamber 210, from reducing the available volume for the plasma filtering. In some cases, for example, an expansion in chamber size, e.g., as the sample is moved into the reporter chamber 210 can cause bubbles to form. Agitating the sample with the reporter can generate foam, with additives in the reporter formulation such as surfactants exacerbating foam generation. Multiple cycles of sending a sample between the de-bubbling channel 212 and the mixer 208 repeatedly washes the sample over the reporter chamber 210, providing good mixing and reducing or eliminating foam from the sample to be sent to the sensor channel 214. According to various implementations, the sample may pass complete at least two passes through the mixer 208, the reporter chamber 210 and the de-bubbling channel 212 prior to delivery to the sensor channel 214, e.g., between three and seven passes.

In some other implementations, a de-bubbler channel may be outside the mixing circuit, with the sample sent to the de-bubbling channel after mixing is complete. In some implementations, a buffer zone (not shown) is disposed between the de-bubbler channel 212 and the mixing chamber 208 to prevent fluid sample from entering the de-bubbler 212 during mixing. This is described further below with respect to FIG. 3. Multiple cycles of sending a sample between a buffer and the mixer 208 repeatedly washes the sample over the reporter chamber 210, providing good mixing and reducing or eliminating foam from the sample to be sent to the sensor channel 214. According to various implementations, the sample may pass complete at least two passes through the mixer 208, the reporter chamber 210 and a buffer prior to delivery to the de-bubbling channel 212 and the sensor channel 214, e.g., between three and seven passes. In some implementations, a cartridge may include multiple parallel de-bubbling channels, e.g., if there are separate sample streams, each of which is to be mixed with a different solid reagent.

As described further below, the mixer 208 can include a fluidic chamber and a pneumatic displacement chamber separated by an elastomer membrane. Actuation of mixer 208 by application of vacuum and/or pressure to the pneumatic displacement chamber can pump the sample in and out of the fluidic chamber during mixing.

In some implementations, the components of the cartridge (e.g., chambers and channels) are sized to prevent passage of a bubble formed in one compartment to another. In some implementations, each subsequent chamber is smaller than the previous one. In some implementations, a volume of the reporter chamber can be between about 1.5-3 times greater than a volume of the de-bubbling channel, while the volume of the de-bubbling channel can be about 1.5-3 times greater than a volume of the sensor well. For example, in some implementations, a volume of the reporter chamber can be about twice greater than a volume of the de-bubbling channel, while the volume of the de-bubbling channel can be twice greater than a volume of the sensor well.

The volume of the fluidic chamber of the mixer may be greater than or equal to a combination of volumes of de-bubbler and reporter well to allow the sample to fold over during agitation. The fluidic chamber of the mixer 208 may have a deeper profile (relative to the de-bubbling channel and reporter chamber) to reduce foot-print and allow optimal mixing. For example, the fluidic chamber of the mixer 208 may have a height at least twice greater than one or more of the nominal channel height of the reporter chamber 210, the de-bubbling channel 212, and the fluidic channels that connect these components to increase turbulence and decrease footprint.

The size of the reporter chamber 210 may be driven by the size of lyphophilized pellets or quantity of lyophilized powder, with the fluidic chamber of mixer 208 and de-bubbling channel 212 sized accordingly. Example sizes of pellets can be about 1-2 millimeters in diameter. In some implementations, the size of the reporter chamber 210 may be just large enough to accommodate a pellet or other quantity of reporter such that the reporter chamber 210 is substantially filled with reporter prior to use. As noted above, in some implementations, the mixing circuit does not include the de-bubbling channel 212. This can preserve the integrity of the hydrophobic membrane that overlies the de-bubbling channel 212, further increasing de-bubbling efficiency. The foam and bubble reduction features described above facilitate the use of room-temperature reporter system that has sensitivity at least as good as laboratory-based systems that use refrigerated liquid reporters.

In some other implementations, the fluid chamber of the mixer and reporter chamber may have similar volumes, with de-bubbler having a smaller volume, the volumes sized according to the desired sample size at each stage. For example, for a plasma sample of 35 µL, a mixer fluid chamber volume can be 35 µL, a reporter chamber volume can be 34 µL, and a de-bubbler volume can be 14 µL. A buffer zone channel having a volume between about 25 µL, and 30 µL, can be interposed between the reporter chamber and the de-bubbler in some implementations.

Returning to FIG. 2A, cartridge 200 also includes one or more substrate bags and one or more wash bags, to be released during the assay. These are indicated at 240 in FIG. 2A. In certain implementations, cartridge 200 includes one substrate bag and one wash bag. Examples of substrates for peroxidase-mediated electrochemical assays include p-phenylenediamine (PPD) and 3,3',5,5'-Tetramethylbenzidine (TMB). Examples of substrates for phosphatase-mediated electrochemical assays include p-aminophenyl phosphate (PAPP). Any appropriate wash solution may be used. Example bag volumes range from 1-5 mL; the cartridge may contain smaller or larger bags in some implementations. In some implementations, only a single reagent pouch is present. For example, a pouch can contain a solution suitable for both washing and performing as an electrochemical substrate.

Wash and substrate bags provided in cartridge 200 may be individually sealed such that no other components of cartridge 200 are exposed to wash and substrate materials prior to testing of a sample. During testing, the wash and substrate bags may be punctured and delivered to the sensor channel 214 in accordance with sequences described with reference to FIG. 1B above and FIG. 3 below. Puncture mechanisms are described with reference to FIGS. 6A-6E. In certain implementations, reagent pouches are opened by rupture spikes 242, which can penetrate through the airline plate 238 and supports 241 to reach the reagent pouches 240. In FIG. 2B, pneumatic rupture spike actuation mechanisms are indicated at 216 and 218.

Microfluidic layer 236 also includes a sensor channel 214, which aligns with one or more electrochemical sensors of a sensing assembly 234 for sensing various components of a sample. Various features of sensor assemblies and corresponding channels are described below with reference to FIGS. 7A-7D. In certain implementations, sensor channel 214 is in proximity with a heater to maintain a certain predetermined temperature of various components in sensor channel 214, such as a sample and probes.

In certain implementations, the volume of a sample introduced to the cartridge is between about 50 microliters and 200 microliters, for example, about 100 microliters of the whole blood. Only a portion of the sample is passed through the plasma separation membrane and used to dissolve the reporter. For example, only about 35 microliters may be used. A portion of this volume containing the reporter is then supplied into the sensor channel. In certain implementations, the sensor channel may support between about 10 microliters and 20 microliter, for example, about 12 microliters.

Liquid communication between different channels and/or compartments of cartridge may be adjusted by operation of valves, such as pneumatically actuated diaphragm valves. For example, one of the diaphragm valves in FIG. 2B is indicated at 252. Diaphragm valves may include an elastomeric membrane separating fluidic channels from pneumatic channels or ports. Application of pressure and/or vacuum may be used to actuate the valve opening and/or closing. According to various implementations, each valve may be closed or open in its unactuated state, as appropriate. Examples of diaphragm valves that may be used are described below with reference to FIGS. 5A-5C. Vents to ambient may also be included. In some implementations, fluid may be pumped by pneumatic displacement chambers separated from a fluidic chamber. For example, mixer 210 and waste pump 220 in FIG. 2B may be used to pump sample and waste, respectively. In the example of FIG. 2B, eight pneumatic inputs from a reader are indicated at 250, though any appropriate number may be used. In some implementations, the total number of valves and displacement chambers may be less than the number of pneumatic inputs, with a single input controlling multiple valves and/or displacement chambers, reducing size and power requirements of the reader.

In some implementations, pressure/vacuum is applied throughout use to actively control and prevent fluid movement. This allows the device to be handheld during use without needing be rested on a flat, stable surface. Active control of the liquid movement prevents it from undesired sloshing, movement, etc. when the reader and cartridge are moved. This can also be useful if the device is used in transit, for example, if detection is performed while in a moving automobile or the reader is on a moving gurney with a patient, liquid remains isolated in the detection channel.

Cartridge 200 may be a single-use cartridge, with the sensors and cartridge materials disposable after use. In certain implementations, some of the reagents are provided in the reader. For examples, substrate and wash liquids may be stored in refillable or replaceable containers in the reader. While this approach simplifies the construction of the cartridge and lowers cartridge costs, it increases the complexity of reader operation and design.

Figure 3:
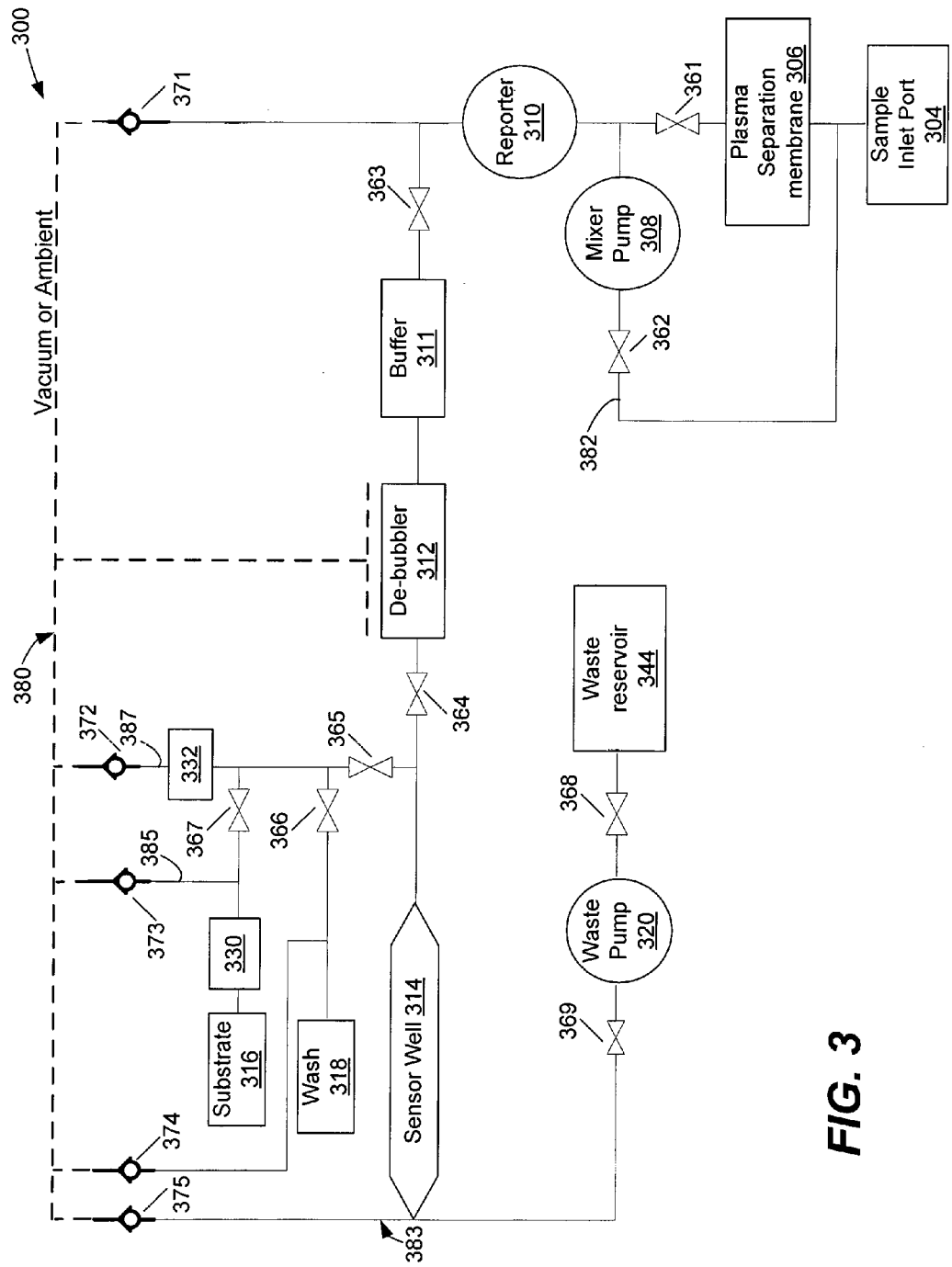
FIG. 3 is an example of a cartridge block diagram for sample filtering, mixing with a reporter, and analysis.

FIG. 3 shows an example of a cartridge block diagram for sample filtering, mixing with a reporter, and analysis. While the diagram and the below explanation refer to a whole blood sample, the block diagram and the process described below may be applied to other types of samples with appropriate modifications. For example, a plasma separation membrane may not be present and in some implementations, may be replaced with an appropriate membrane or filter. A sample input port 304, plasma separation membrane 306, reporter chamber 310, mixer pump 308, buffer zone 311, de-bubbler 312, sensor well 314, wash compartment 318, substrate compartment 316, waste pump 320, and waste reservoir 344 of cartridge 300 are indicated. Also indicated are substrate conductivity check 330, wash conductivity check 332, elastomer valves 361-369, and hydrophobic membrane fluidic stops 371-375. For clarity, pneumatic lines are not illustration, with the exception of line 380, which can lead to vacuum or ambient as indicated.

Fluid may be moved through the cartridge by one of two methods that involve pneumatic actuation via the pneumatic lines: 1) vacuum is applied through a hydrophobic barrier layer in the multi-layer microfluidic layer that functions as fluidic stop and 2) on-cartridge diaphragm pumps actuated by applied pressure and/or vacuum. The same reader pneumatic source can be used for opening and closing diaphragm valves, operating the on-cartridge pumps, de-bubbling, moving fluid to the fluidic stop, and operating bag rupture mechanisms. This permits only a small portion of the cartridge to be inserted and interact with reader, as indicated at interface portion 106a of FIG. 1A.

In use, a sample may be introduced to sample inlet port 304. This can be a set volume determined by a sample collection container with the amount determined by the amount of sample desired in the sensor well. In one example, 100-150 µL of whole blood is introduced. The cartridge is then put into a reader, which in some implementations closes all valves as part of an initiation procedure. The reader may identify the card with the user confirming the type of cartridge and assays. No further user input or attention may be needed in some implementations, with the assays performed automatically by the reader.

At this point, the whole blood sample is held on the sample input side of the plasma separation membrane 306 by the membrane. A vacuum applied through line 380 and valve 361 is opened to extract plasma through the filter and into the reporter chamber 310. (The applied vacuum also causes the substrate bag to rupture and the substrate fluid to be prime channel 385 as described below.) The size of the reporter chamber 310 can set the sample size. For example, for a sample size of 35 µL, a reporter chamber of 34 µL will be filled until full with an additional 1 µL in the channel. A sample size may be slightly larger than the volume reporter chamber 310, due to the presence fluid in the fluidic channels; however, this amount can be precisely known to set a precise sample amount. The vast majority of this volume may be in a molded part of the cartridge, with precision tolerances. In some implementations, the reporter chamber 310 is assumed to be filled after a programmed amount of time is elapsed, e.g., 2-5 minutes. In some other implementations, a feedback mechanism may be employed to confirm the reporter chamber is completely filled. Note that if there reporter chamber 310 is not filled, e.g., because the user did not add enough whole blood sample to the cartridge, one or more mechanisms may be employed to detect insufficient sample. Insufficient sample can cause bubble formation, for example, which may be detected as discussed further below.

In some implementations (not shown), valve 362 can be connected to ambient. However if the valve is not airtight, some small amount of air may be pulled into the sample when the vacuum is applied during the filtration process. This may be a very small amount, e.g., on the order of ten or a hundred nL/min. In some implementations, however, the valve is made airtight by providing a liquid in the channel 382. The liquid prevents air from entering the channel 382 through the valve 362, providing an airtight seal. In the example of FIG. 3, the channel 382 is connected to the sample inlet such that liquid is supplied by the unused whole blood sitting on the membrane 306. Preventing formation of even 50 nL or smaller bubbles from being in the plasma sample can provide precision liquid measurements and assays and cartridge-to-cartridge uniformity.

The reporter chamber 310 contains lyophilized reporter, e.g., 10 mg antibody, along with sugars and other components of a lypohilized reporter pellet. These begin to dissolve in the sample. Valve 361 is closed, the vacuum turned off, and valve 363 is opened. The displacement chamber of mixer pump 308 is opened and closed to pump the sample back and forth over the reporter chamber 310. As the sample is pumped, air is introduced to the sample from line 380 (now at ambient), with the sample volume increasing as the sample froths. In the example depicted in FIG. 3, there is a buffer zone 311, which may be a long channel. The width of the buffer zone channel is sufficiently narrow such that the fluid moves as a column. For example, it may be between 300 µm-400 µm wide.

The buffer zone 311 prevents the sample from reaching the de-bubble 312 during mixing. (As described above, in some other implementations, the de-bubbler may be part of the mixing circuit). The volume of buffer zone 311 is large enough such accommodate the increasing sample size without allowing the sample to reach the de-bubber 312 during mixing. For example, a cartridge using about 35 µL plasma sample may have a buffer zone channel volume of about 25 µL-30 µL. The buffer zone channel may be fairly long to accommodate the volume and width requirements and can be arranged in a serpentine or other circuitous path as appropriate to fit on the cartridge. The sample proceeds further along the buffer zone with each successive cycle as the amount of air in the sample increase, and accordingly, the volume and length of the buffer zone channel may vary according to a number of mixing cycles desired for a particular cartridge design. The buffer zone 311 may be advantageous when exposure to the sample may be apt to foul the hydrophobic membrane of the de-bubbler 312, e.g., by having antibodies and other biomolecules in the sample adhere to the membrane. This can hamper the ability of air to be vented out of the de-bubbler membrane, as well as the ability of air to be introduced to the sample during mixing.

Once mixing is complete, vacuum is applied to the de-bubbler channel 312. The sample, including dissolved reporter and air, is pulled into the de-bubbler channel. Any air bubbles inside of the sample are pulled through the hydrophobic membrane overlying the de-bubbler until is filled with a continuous bubble-free liquid. For example, a 14 μL de-bubbler will have 14 μL of bubble-free liquid. The reader may apply vacuum to the de-bubbler for a few minutes to remove micro-bubbles from the frothing, which may take longer to remove than larger bubbles, to leave. Example vacuums may be about 1 to 10 psi, e.g., 5 psi less than ambient atmospheric pressure.

Valves 362 and 364 are then opened and a vacuum is applied to line 380 to move the sample into the sensor well 314. Opening valve 362 allows air from the channel 382 to fill from the backend, allowing the liquid in the de-bubbler 312 to move into the sensor well 314. Most of the liquid is in the sensor well itself, with a small amount of liquid in the channel 383. See, e.g., FIG. 2B, in which 0.1-1 μL may be moved into channel 224. In some implementations, described further below with respect to FIG. 8A, this amount may be reduced or eliminated. Once the liquid is in the sensor well, a check for bubbles may then be performed. Bubble detection methods are discussed further below, with respect to FIG. 10B.

At this point in the process, channels 385 and 387 may be already be primed, with the substrate fluid in channel 385 and wash fluid in channel 387. In the example of FIG. 3, the substrate bag is ruptured when the vacuum is first applied through line 380. The substrate fluid may prime channel 385, removing bubbles from the substrate fluid and the channel 385. The wash bag is ruptured and wash fluid flowed into channel 387, priming channel 387 when valve 366 is opened and removing bubbles from the wash fluid and channel 387. As indicated above, in certain implementations, multiple valves may be connected to the same pneumatic line to reduce space requirements and complexity. In one example, valve 366 may be connected to the same line as valve 363, with the wash fluid moving into channel 387 when valves 363 and 366 are opened simultaneously at the start of the mixing process described above. Conductivity checks 330 and 332 confirm that the substrate and wash fluids, respectively, are released from their bags and are in primed channels 385 and 387. Conductivity checks may include electrodes through which current flows in the presence of conductive fluids.

The sample incubates in the sensor well for a period of time, e.g., 5 minutes, prior to wash fluid being pumped to the sensor well 314 to wash reporter out. Valves 365 and 366 are opened and all other valves are closed. The waste pump 320 and valves 369 and 368 are actuated to move wash fluid from the wash compartment 318 and channel 387 over the sensor well 314 and into the waste reservoir 344. The amount of wash fluid used to wash the sensor well is precisely controlled by the number of pump strokes. In some implementations, the wash fluid can be pumped back and forth over the sensor well 314 before sending the wash fluid to the waste reservoir 344. This may facilitate reducing the amount of liquid washed used and stored on-cartridge. In some implementations, the wash fluid may be allowed to sit in the sensor well 314 to allow a sufficient amount of time for orthogonal diffusion of the unbound reporter into the wash liquid.

Once the wash fluid is pumped to the waste reservoir 344, the substrate is connected is to the waste pump 320 to pump the substrate to the sensor well 314. Valve 366 is closed, with valves 365 and 367 open to connect the substrate in the substrate compartment 316 and the channel 385 to the sensor well 314. The waste pump 320 and valves 369 and 368 are actuated to pump the fluid over the sensor well 314. The amount of substrate passed through may be a multiple of the sensor well volume, e.g., 4-8 times the volume of the sensor well 314. This can ensure any remaining wash fluid in the sensor well is diluted with the electrochemical buffer of the substrate reagent. The substrate can be pumped over the sensor well 314 multiple times, e.g., 2-4 times. The current is measured at each sensor, with the measurement corresponding to the quantity of analyte. At this point, the cartridge is used and can be removed from the reader and discarded.

According to various implementations, the time from insertion to results may be less than 30 minutes, and can be 10-15 minutes or even faster depending on if and how long the sample is incubated. If plasma filtration is not performed (e.g., for whole blood samples, non-blood samples, or plasma delivered to the cartridge), the time may be further reduced. Still further, for a cartridges that do not need sample incubation (e.g., a metabolite panel), the total processing time may be as fast as 2 or 3 minutes.

Figure 11A:
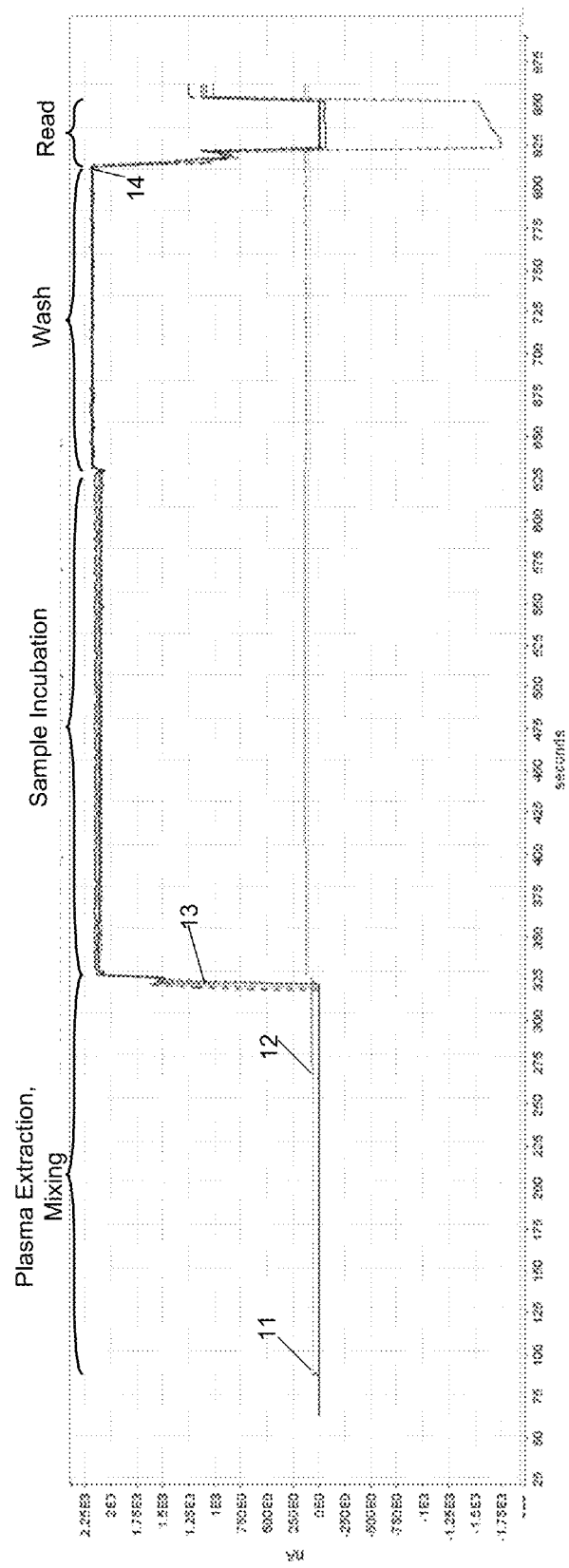
FIGS. 11A-11C show examples of sensor current, reader pressure and vacuum, and sensor temperature and heater duty cycle during operation.

The sensor well may be heated as appropriate for the particular assay(s) performed during sensing. FIG. 11C below provides an example of temperature control in the sensor well during sensing. Heating can occur by any appropriate method, with an examples of heaters according to certain implementations described below with respect to FIG. 7B.

While FIG. 3 provides an example of a flow diagram, various modifications can be made without departing from the scope of the description. For example, while flow through the sensor well is uni-directional in FIG. 3, it some implementations, cross flows may be implemented to split a sample and introduce different portions of the sample at different locations of the sensor well. This may be done to provide uniform exposure characteristics to two or more sensors at two or more locations in the sensor well. In some implementations, a sample may be split and directed to two or more sample wells provided in parallel. Substrate, wash and/or other reagent flows can be redirected to two or more locations of a well or two or more wells as appropriate as well.

Figure 1D:
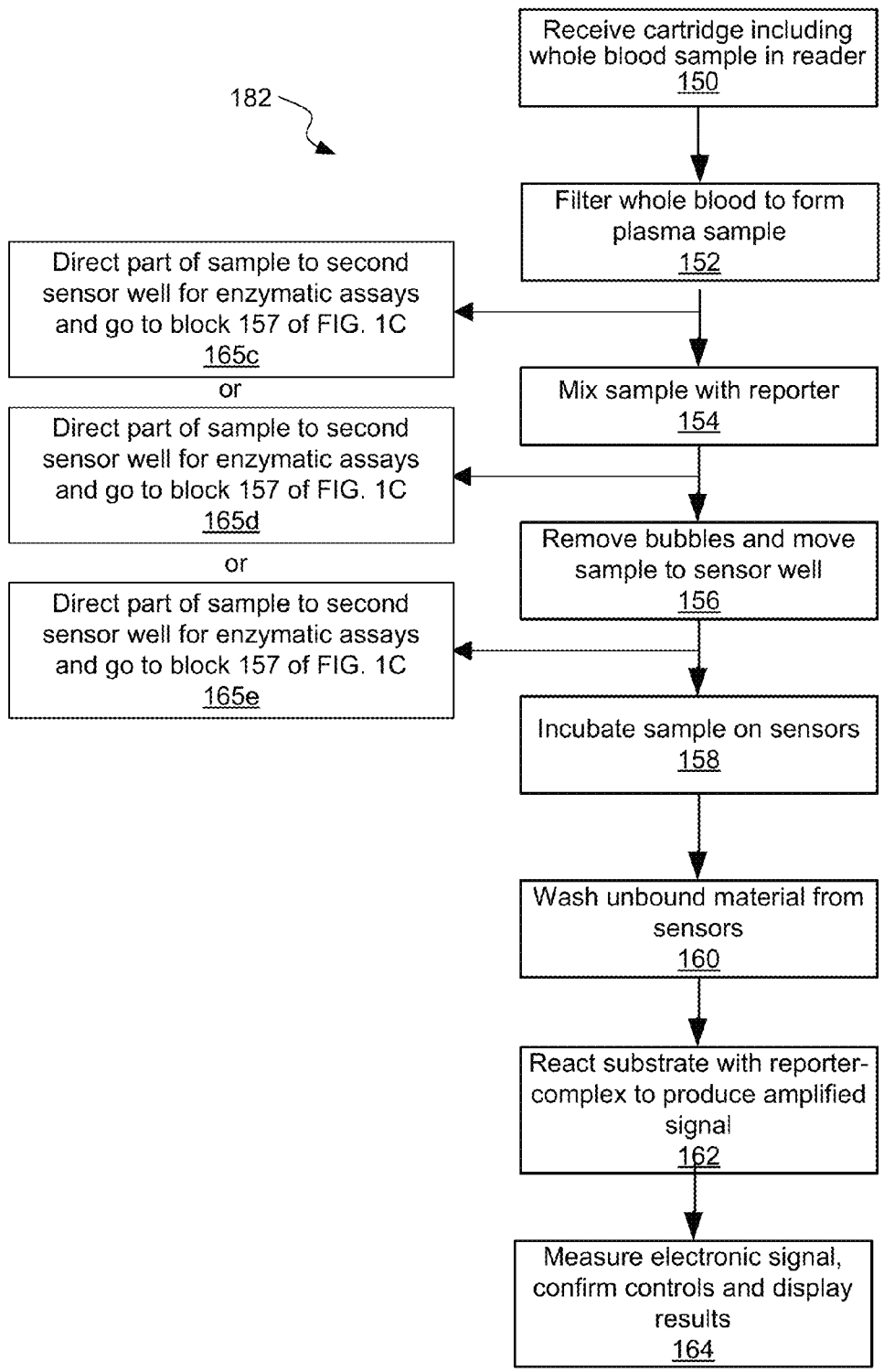
Figure 2C:
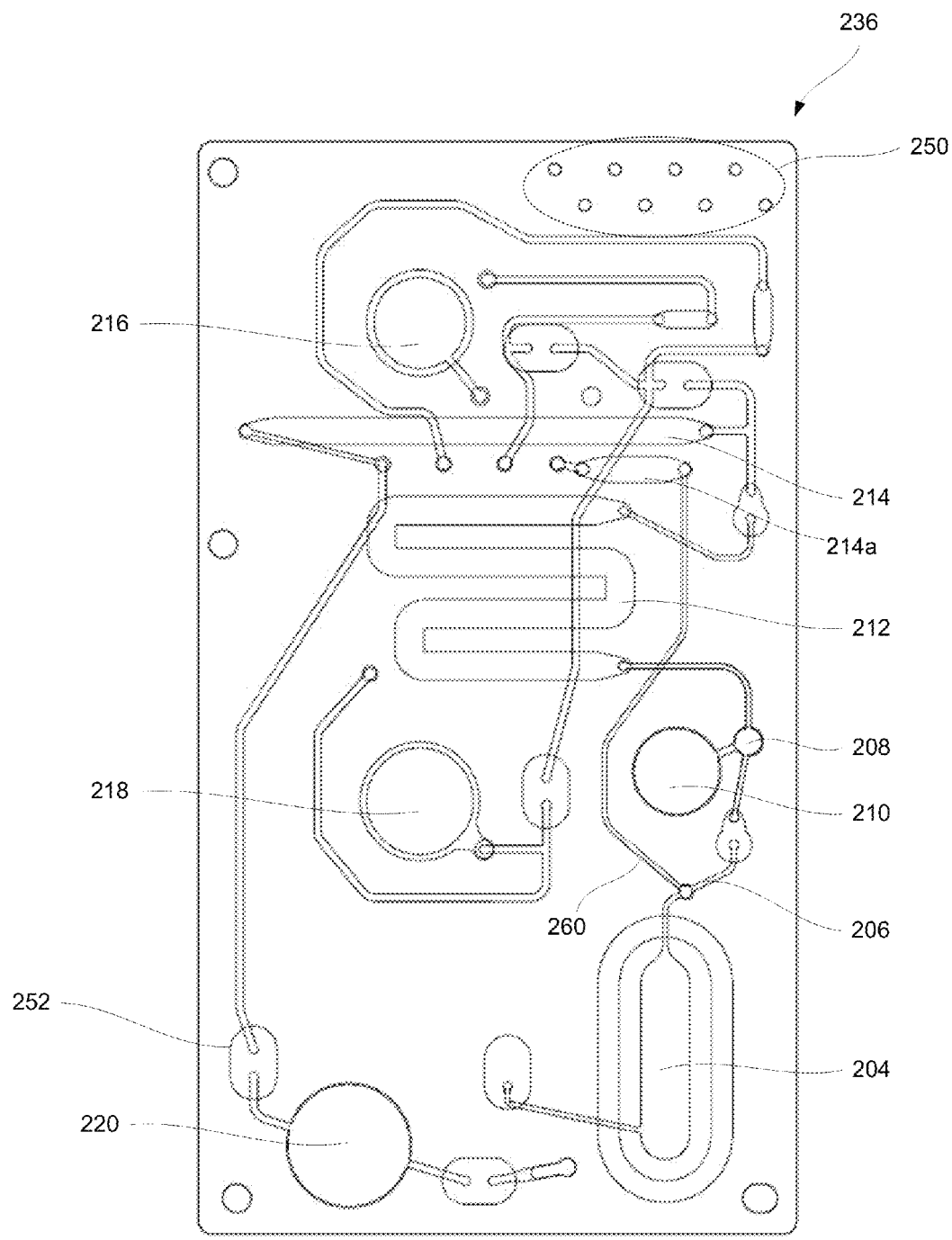

FIG. 1D is a process flow 182 showing certain operations in methods of performing enzymatic and electrochemical sandwich ELISA assays in parallel sensor wells using a single whole blood sample. Blocks 150-164 can be performed as described above with respect to FIG. 1B, with a portion of the sample directed to a second sensor well at one of blocks 165c, 165d, or 165e. If block 165c is performed, the sample is split after the whole blood is filtered to form the plasma sample in block 152. After being split, the enzymatic assay can be performed as described in FIG. 1B. FIG. 2C is a schematic of an example of a micro-fluidic layer 236 that can be used in accordance with process flow 182 if block 165c is performed. FIG. 2C shows various compartments, channels, valves, and other components of microfluidic layer 236 as shown in FIG. 2B, with the addition of a side channel 260 leading to a second sensor channel 214a. In some implementations (not shown), the sample may be mixed with one or more solid or liquid reagents (e.g., reporters, enzymes, mediators, etc.) prior to delivery to the second sensor channel 214a and/or one or more reagents may be delivered to the sensor channel 214a. These can be the same or different reagents delivered to sensor channel

214. If mixed with a solid reagent, the split sample may or may not be sent through a de-bubbling channel according to various implementations. In some implementations, the sample may be split prior to filtration, e.g., if the enzymatic assay is to be performed in whole blood. The second sensor channel 214a may be located parallel and relatively close to sensor well 214 to share a common heater in some implementations.

Figure 2D:
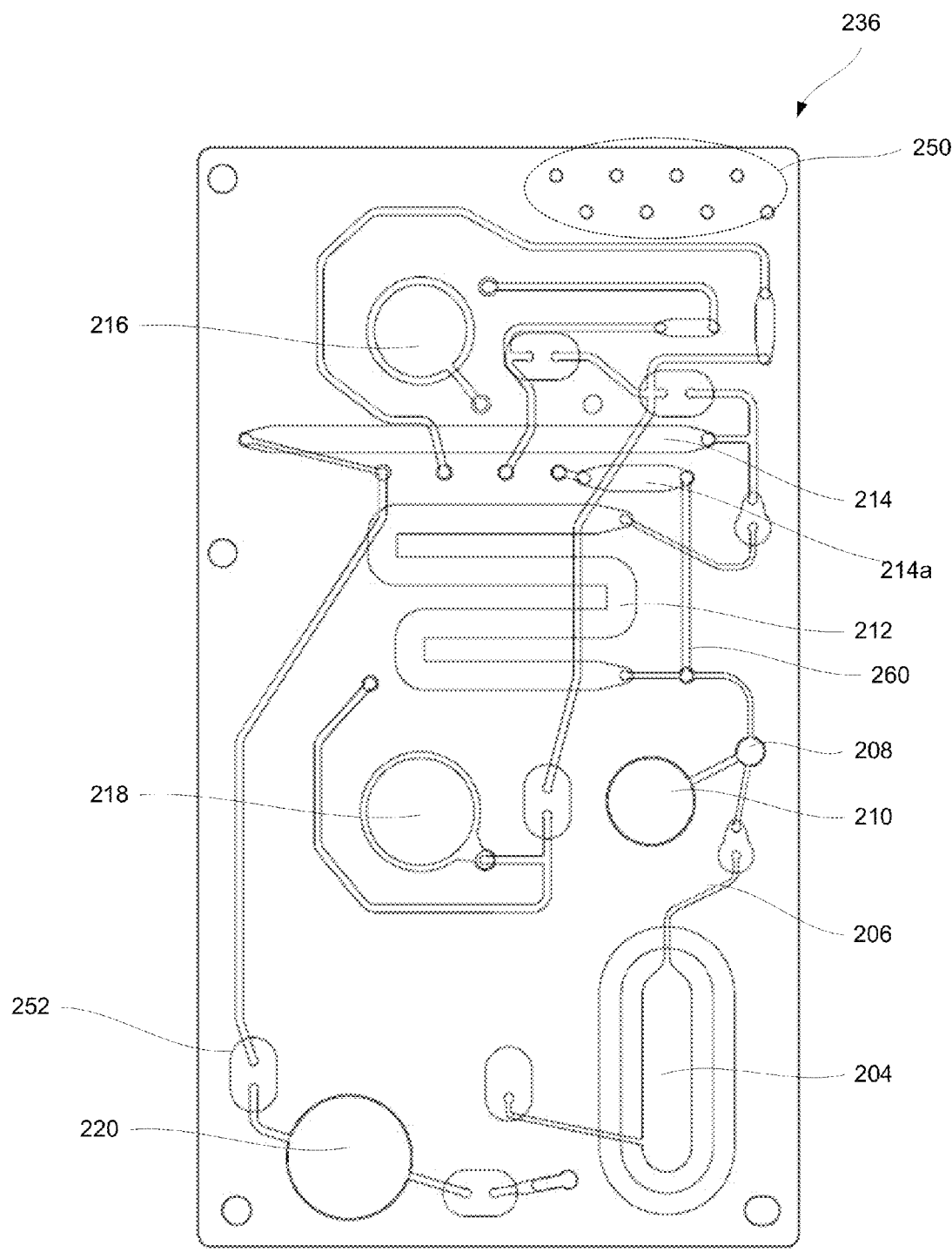
Figure 2E:
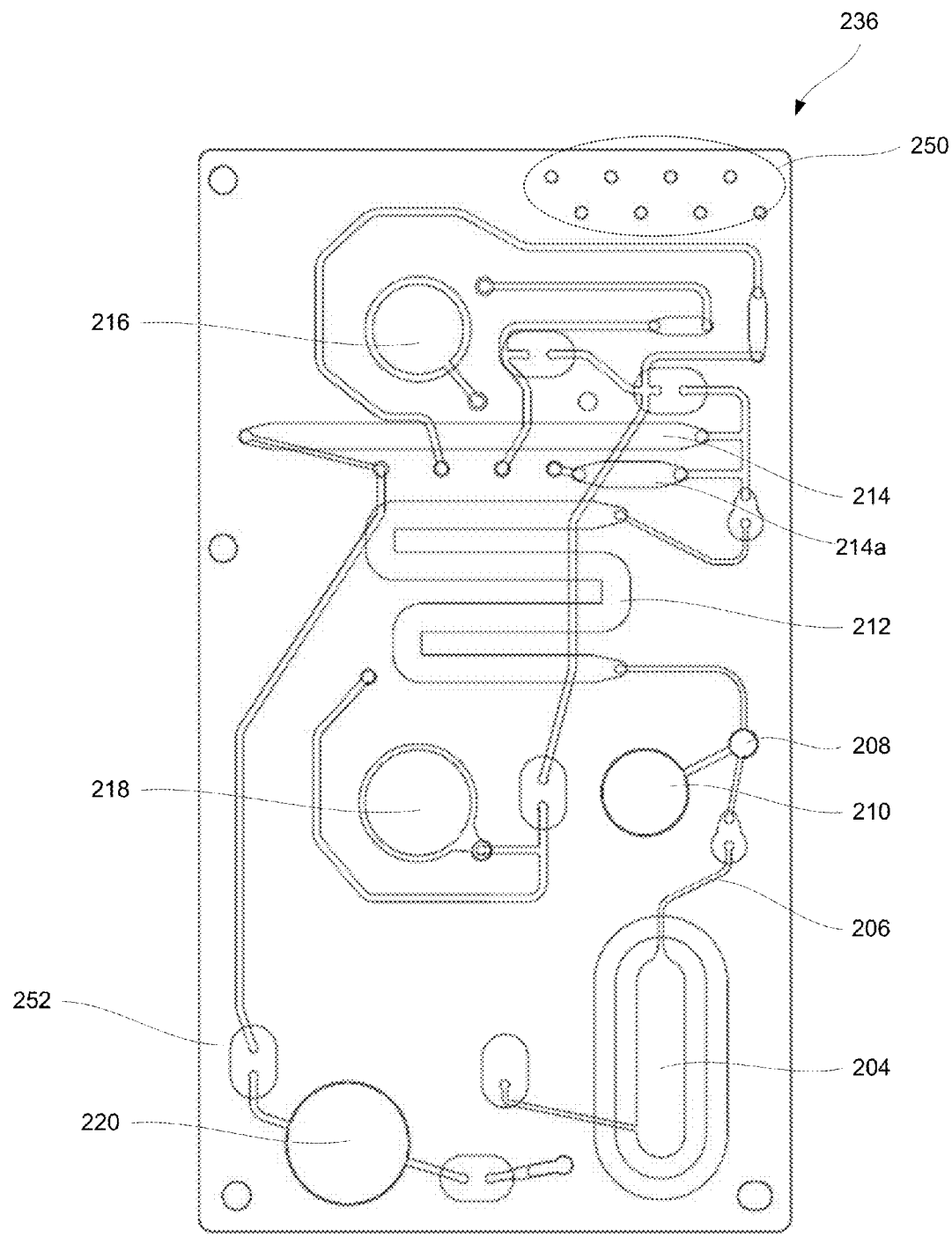

In some implementations, the split sample may be de-bubbled in a de-bubbling channel. In some implementations, the assay performed in the second sensor well may be less sensitive to bubbles and go directly to the second sensor well. Returning to FIG. 1D, if block 165d is performed, the sample is split after the sample is mixed with a reporter in block 154. After being split, the enzymatic assay can be performed as described in FIG. 1B. FIG. 2D is a schematic of an example of a micro-fluidic layer 236 that can be used in accordance with process flow 182 if block 165d is performed. FIG. 2D shows various compartments, channels, valves, and other components of microfluidic layer 236 as shown in FIG. 2B, with the addition of a side channel 260 leading to a second sensor channel 214a. Returning again to FIG. 1D, if block 165c is performed, the sample is split after de-bubbling in block 156. After being split, the enzymatic assay can be performed as described in FIG. 1B. FIG. 2E is a schematic of an example of a micro-fluidic layer 236 that can be used in accordance with process flow 182 if block 165e is performed. FIG. 2E shows various compartments, channels, valves, and other components of microfluidic layer 236 as shown in FIG. 2B, with the addition of a side channel 260 leading to a second sensor channel 214a.

Figure 4A:
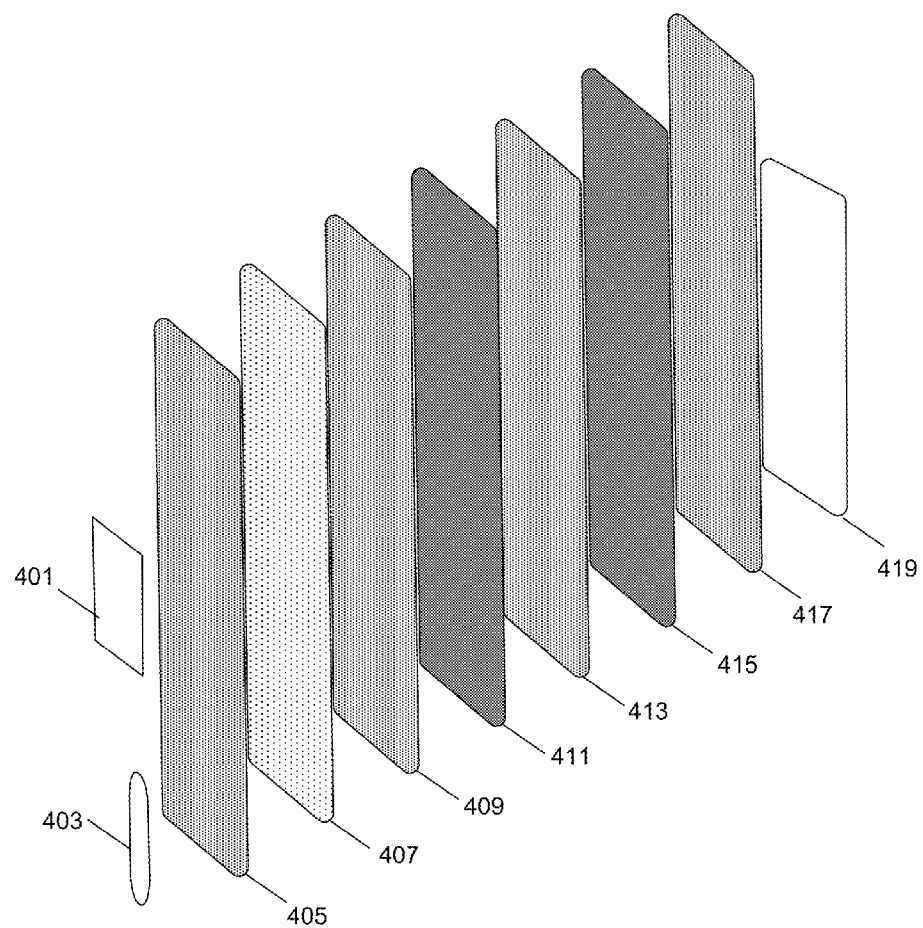
FIGS. 4A-4H are simplified drawings of examples of layers of a multi-layer microfluidic layer.

FIGS. 4A-4H are simplified schematic drawings of examples of layers of a multi-layer microfluidic layer. While some features, such as a de-bubbling channel, are depicted, other fluidic and pneumatic channels, as wells as ports and interlayer vias are not depicted or simplified for illustration. It should be understood that there are various channels, valves, ports and interlayer vias may be arranged in different layers according to various implementations, and that the arrangement of these feature in a particular layer will also vary according to the particular implementation. Turning first to FIG. 4A, layers 405-419 are depicted, as are plasma separation membrane 403 and hydrophobic membrane 401. Layer 407 is a monolithic (single piece) flexible membrane that may function as the diaphragm for all diaphragm valves in the cartridge. Layers 405, 409, 413, and 417 can be laser-cut adhesive material. Layers 411, 415, and 419 can be molded or cut plastic materials.

Examples of adhesives include pressure-sensitive adhesives by 3M including 300LSE, 200 MP, 300 MP, acrylic adhesives, optically clear acrylic adhesives, and silicon adhesives. Other adhesives that may be used include other pressure sensitive adhesives, heat active adhesive, screen printable adhesives, pad printable adhesives, laser (IR) welding for injection molded parts, sonic welding, heat seal, and solvent bonding.

Each of the layers of a multilayer laminate described herein is generally stable at temperatures at which the sensing is performed. In some implementations where higher temperatures are used, pressure/vacuum to the valves may be turned off during heating to help prevent delamination.

Each of layers 405, 409, 413, and 417 can include one or more fluidic channels, with layer 413 providing including most of the fluidic channels, layer 409 including the main portion of the de-bubbling channel in one example, and layer 417 including the sensor well in one example. Layer 405 can provide pneumatic chambers of microvalves, pumps and bag rupture mechanisms and can be connected to pneumatic lines in an airline plate. Layers 409-413 can provide fluidic chambers and seats for diaphragm valves and pumps and bag rupture mechanisms. Each of the layers may include vias for inter-level pneumatic and fluidic connections. Layer 415, for example, may include vias for fluidic connection between layers 413 and 417 and layer 411 may include vias for fluidic connection between layers 413 and 409.

Figure 4B:
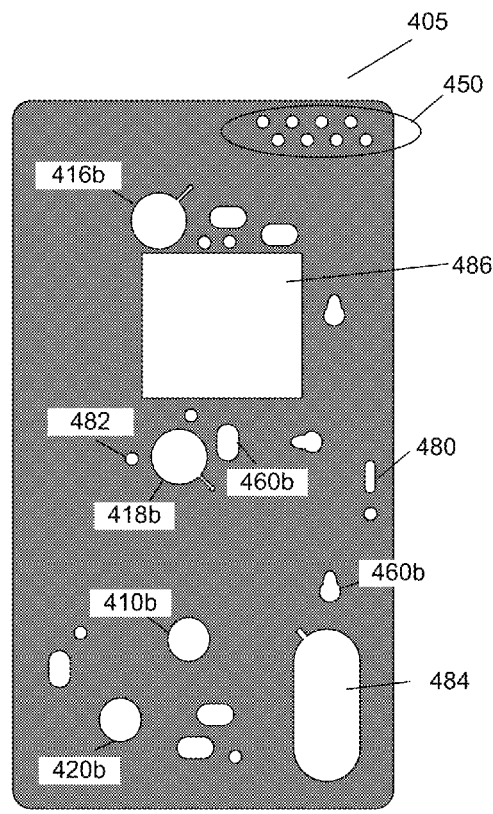
Figure 4C:
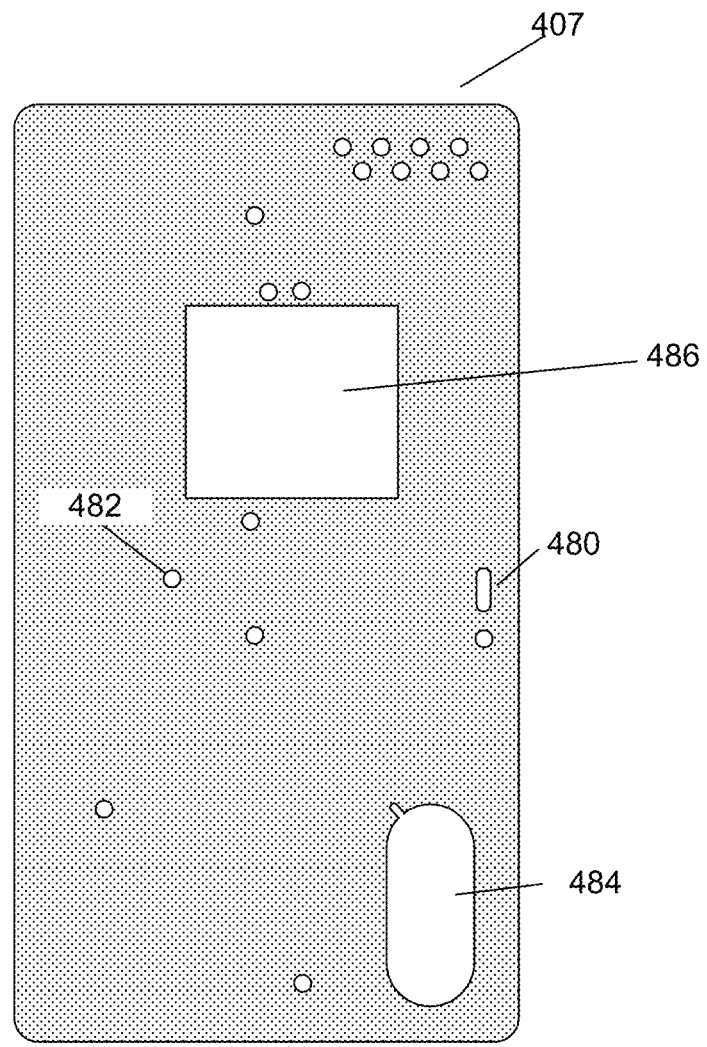
Figure 4D:
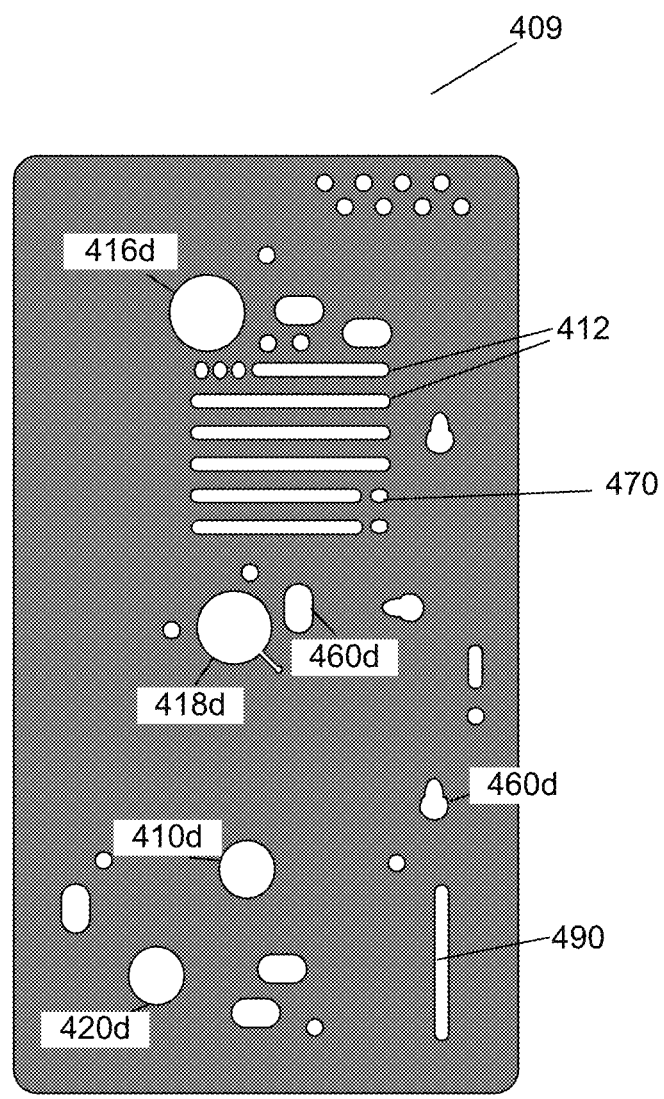
Figure 4E:
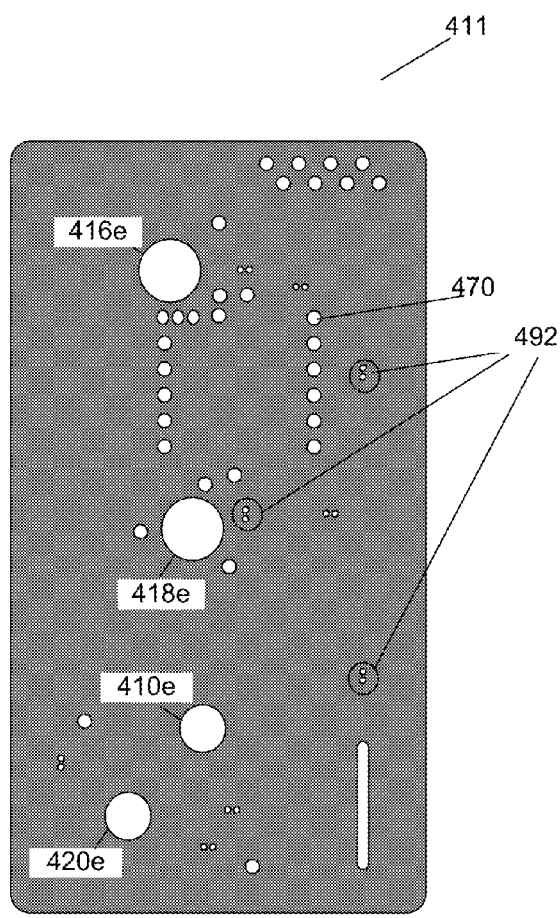
Figure 4F:
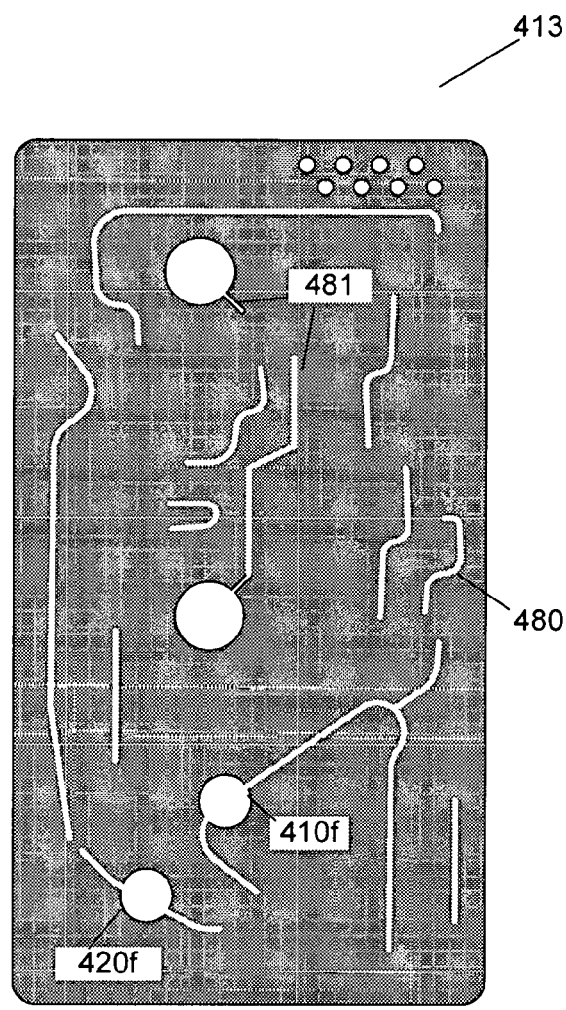
Figure 4G:
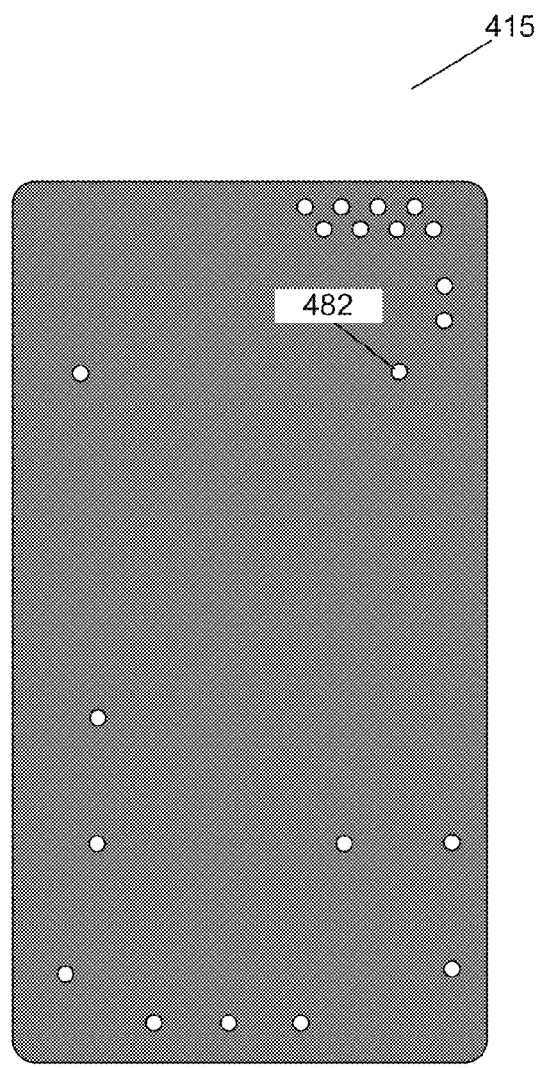
Figure 4H:
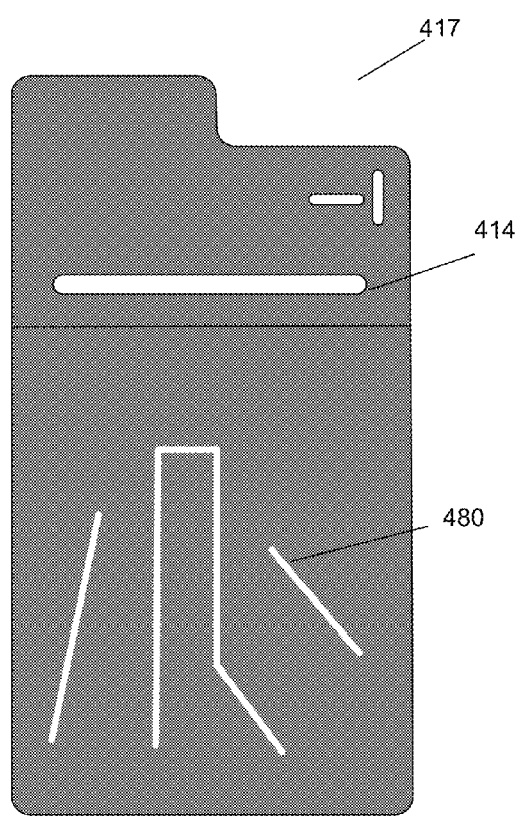

Turning to FIG. 4B, a simplified schematic diagram of a layer 405 is depicted. Layer 405 includes pneumatic ports 450, as well as chambers 416b and 418b of bag rupture mechanisms, pneumatic chamber 410b of a mixer pump, pneumatic chamber 420b of a waste removal pump, and pneumatic chambers 460b of diaphragm valves. Layer 405 may also include one or more fluidic channels 480, and inter-level vias 482. Apertures 484 and 486 are sized to fit the plasma separation membrane 403 and hydrophobic membrane 401 shown in FIG. 4A, respectively. FIG. 4C depicts a simplified schematic diagram of a layer 407. As indicated above, layer 407 is a polymeric flexible membrane and also includes apertures 484 and 486 sized to fit plasma separation membrane 403 and hydrophobic membrane 401, respectively, as well as channels 480 and vias 482. FIG. 4D shows a simplified schematic diagram of layer 409, which includes pneumatic chambers 416d and 418d of bag rupture mechanisms, fluid-side chambers 410d and 420d of mixer and waste removal pumps, fluid side chambers 460d of diaphragm valves. Layer 409 also includes de-bubbler channels 412 and check valves 470, which abut the hydrophobic membrane 401 depicted in FIG. 4A. Channel 490 abuts the plasma separation membrane 403 in FIG. 4A, allowing filtered plasma sample to flow to fluidic channels in layer 413. FIG. 4E depicts a simplified schematic diagram of layer 411, which includes which includes chambers 416e and 418e of bag rupture mechanisms, fluid-side chambers 410e and 420e of mixer and waste removal pumps as wells as vias such vias 470e that connect to de-bubbler channels 412. Layer 411 also includes fluidic passages/vias 492 for diaphragm valves, which are blocked by the diaphragm when the diaphragm valves are closed. FIG. 4F depicts a simplified schematic diagram of layer 413, which includes most of the fluid channels of the cartridge in this example. For example, channels 481 lead from bag rupture mechanisms to a sensor well of layer 417. The remaining fluidic channels 480 are depicted generically with arrangement and detail of specific fluidic channels omitted. Examples of fluid flow paths are shown above with respect to FIG. 3. Fluid-side chambers 410f and 420f of mixer and waste removal pumps are also depicted. FIG. 4G depicts an example of layer 415, which is a plastic layer including vias for inter-layer connections, including fluidic connections to the sensor well of layer 417. FIG. 4H is a schematic depiction of layer 415 including sensor well 414 and additional fluidic channels 480 that may be connected to layer 413 by vias in layer 415. Layer 417 may provide, for example, space for fluidic channels that cannot be accommodated on layer 415. While FIGS. 4A-4H provide examples of arrangements of layers of microfluidic layer, according to various implementations, a microfluidic layer may include any number of layers. For example, a smaller form factor cartridge may include additional layers to accommodate the channels. Similarly, a larger form factor cartridge may include fewer layers.

Figure 5A:
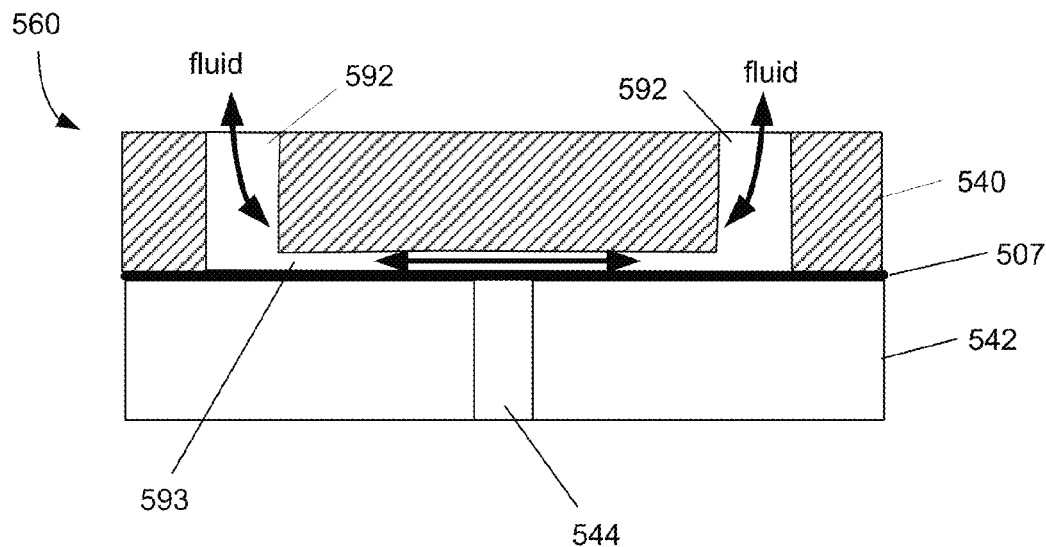
FIGS. 5A-5C are schematic drawings of examples of diaphragm valves that may be used in accordance with various implementations.
Figure 5B:
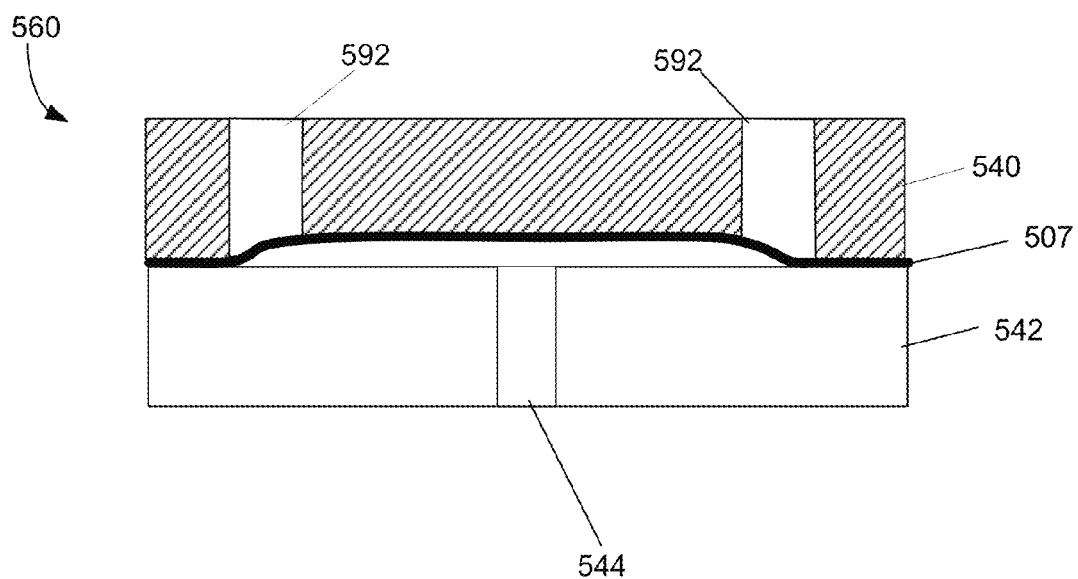

FIGS. 5A and 5B provide one example of a diaphragm valve that may be used in accordance with various implementations. FIG. 5A depicts diaphragm valve 560 open, which can allow bi-directional fluid flow as depicted. Diaphragm valve includes membrane 507, and fluid-side and pneumatic-side layers 540 and 542. (Each of layers 540 and 542 may be composed of one or more layers or the microfluidic layer.) Fluid-side layer 540 includes vias 592 and fluidic channel 593 and pneumatic layer 542 includes pneumatic port 544. (Examples of fluid passageways in a layer of a multilayer microfluidic layer are shown in FIG. 4E at 492). Vacuum and/or pressure from the reader can be applied to the valve 560 via pneumatic lines within the cartridge to deflect the membrane 507 to open and close the valve 560. FIG. 5B shows the valve 560 in a closed position.

Provided also are novel reagent delivery methods and mechanisms for used in point-of-care systems, for example, in cartridges that store liquid reagents used during testing. Various types of liquid reagents are used in biological assays. For example, an ELISA based measurement technique generally uses a wash buffer liquid to clear out unbound species and a substrate reagent to facilitate various reactions and measurements. These techniques use specific wash buffer solutions and substrates for electrochemical sensors to operate. Integration and handling and delivery of various liquid reagents in point-of-care devices may be challenging. While the description herein chiefly references substrate and wash liquids for use in cartridges in electrochemical ELISA systems, these methods and mechanisms described are applicable to any type of liquid reagents that are provided in sealed bags.

In some implementations, the provided reagent delivery methods and mechanisms are based on a pneumatic mechanism that is activated to pierce open seal foil bags. These methods and mechanisms can be easily integrated into microfluidics cartridges described above, since these cartridges already have pneumatic lines (e.g., pressure and/or vacuum lines) provided in the cartridges to control valves, pumps, and liquid movement. The pneumatic power can be supplied by the reader as described above and further below with respect to FIG. 9A. These pneumatic features may be applied to control various components of the delivery system include component that are used to rupture bags containing liquid reagents and delivery of the reagent to the channels.

In certain implementations, the provided reagent delivery methods and mechanisms do not require separate mechanical mechanism and electronic mechanisms for operation. Furthermore, a single pneumatic feature of a cartridge can control delivery of multiple different reagents from different bags in accordance to various operating schemes (e.g., simultaneously or in sequence).

Figure 6E:
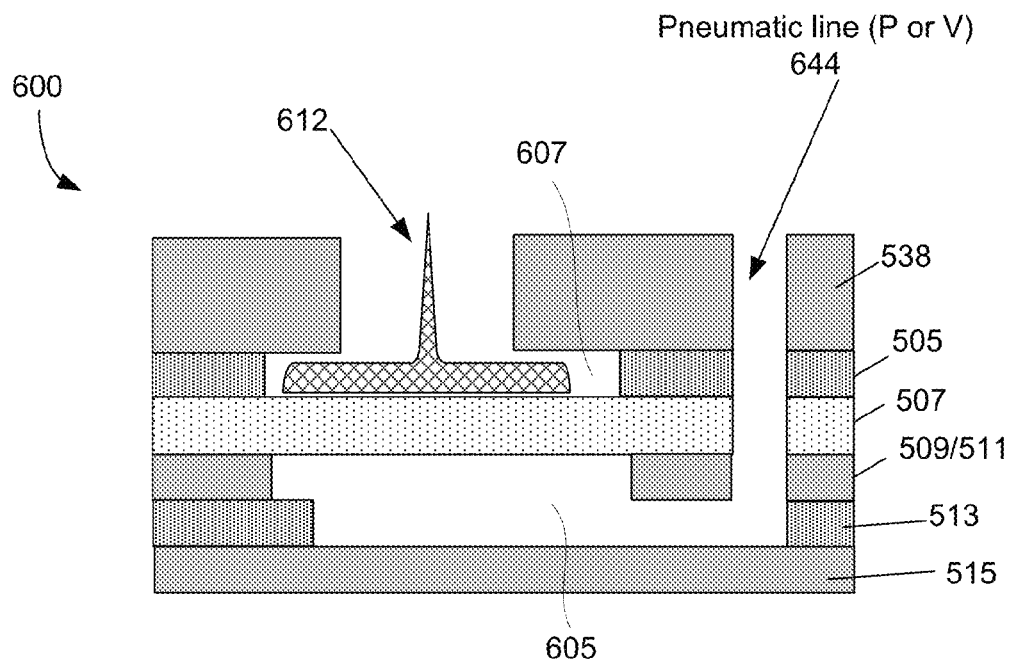
FIGS. 6A-6E are schematic drawings of examples of pneumatic rupture mechanisms in accordance with various implementations.
Figure 6A:
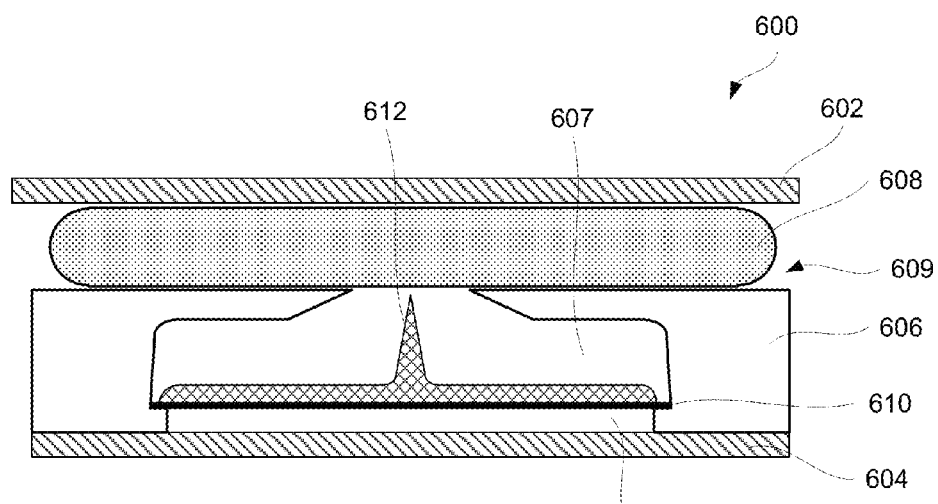

FIG. 6A is a schematic representation of a pneumatic rupture mechanism 600 prior to puncturing a liquid containing bag 608, in accordance with certain implementations. Pneumatic rupture mechanism 600 may be provided between top plate 602 and bottom plate 604 of a cartridge. In some implementations, one or more of top plate 602 and bottom plate 604 may not be an outer plate of a cartridge, but rather housed within a cartridge. For example, bottom plate 604 may be a layer of a microfluidic layer as described above. Other implementations are possible as well, including pneumatic rupture mechanisms in apparatuses such a readers, laboratory instrumentation, and the like. Pneumatic rupture mechanism 600 includes a flexible membrane 610 and spike 612. Flexible membrane 610 separates bottom cavity 605 of mechanism 600 from top cavity 607. Top cavity 607 may be defined by a support 606 that has an opening through which spike 612 can penetrate. Support 606 may be used for supporting liquid containing bag 608. A volume between support 606 and top plate 602 is defined as an external cavity 609. However, a portion of liquid containing bag 608 is exposed to top cavity 607, as for example, shown in FIG. 6A. Liquid containing bag 608 is sealed to the support 606 around the opening in support 606. Flexible membrane 610 can be a membrane such as layer 407 described above with reference to FIG. 4A.

Flexible membrane 610 is used as an actuator for lifting spike 612. In some implementations, flexible membrane 610 is configured to change its shape based on a pressure differential across the membrane, i.e., a difference in pressure between bottom cavity 605 and top cavity 607. When the pressure levels in both cavities are substantially the same, flexible membrane 610 may be substantially flat keeping spike 612 away from liquid containing bag 408 as, for example, shown in FIG. 6A. Flexible membrane 610 may be supported by support 606. For example, flexible membrane 610 may be laminated to support 606 or some other component of the cartridge.

Flexible membrane 610 may be made from polyurethane or other flexible material. Spike 612 may be injection molded from rigid plastics, or may be another suitable material such as metal. In certain implementations, spike 612 can be color coded to easily identify the presence or absence of spike 612 in the assembly during fabrication.

Before actuation of the mechanism, spike 612 may already be in contact with both liquid containing bag 608 and membrane 610. In this example and state, top cavity 607 may have a height that is just enough to accommodate spike 612 such that the tip of spike 612 is just in contact with liquid containing bag 608 without puncturing it. In certain implementations, a height of top cavity 607 may be greater than the height of spike 612. In these implementations, spike 612 may be free floating within top cavity 607 or spike may be attached to membrane 610 and be kept away from liquid containing bag 608.

Figure 6B:
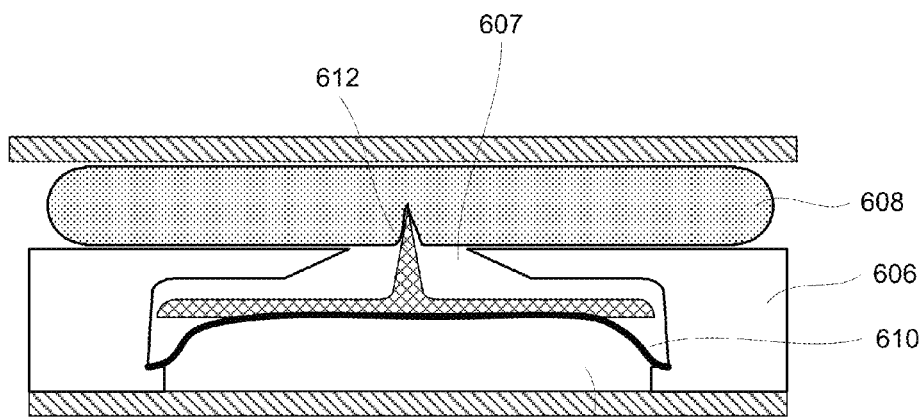

When the pressure inside bottom cavity 605 is greater than the pressure inside top cavity 607, flexible membrane 610 may deform upwards as, for example, shown in FIG. 6B. This deformation raises spike 612 and pushes it again liquid containing bag 608. At certain conditions, spike 612 punctures liquid containing bag 608 and allows liquid to escape from the bag into top cavity 607. In certain implementations, a pressure differential between bottom cavity 605 and top cavity 607 may be at least about 5-10 psi or, for example, at least about 5 psi to achieve bursting of liquid containing bag 608. However, it will be understood that these pressure ranges depend on the particular spike and bag design, e.g., a sharper spike and weaker bag yield strength may require less deformation of the flexible membrane to achieve puncture of the bag. The rupture force or displacement can also be tuned by the design of the surface area of the circular base of the spike. Furthermore, the rupture force or displacement can be tuned by changing the relative pressure differences applied to two sides of the cavities. In certain implementations, a system may have a feedback control loop which causes the pressure differential to increase until the liquid is sensed with top cavity 607. The feedback control loop can include a sensor located in the top cavity 607 or the fluidic channel that extends from the top cavity 607 that senses the presence of fluid. In some implementations, a sensor may be used outside a feedback control loop to provide a check that the cartridge is working. A user may be provided with an indication that the cartridge is not working and needs to be replaced if the sensor does not detect the presence and/or a certain quantity of fluid. For example, in certain implementations, pneumatic rupture mechanism 600 includes a conductivity probe that determined presence or absence of liquid in a line leading to the top cavity. One example is conductivity check 330 in FIG. 3.

The pressure differential between bottom cavity 605 and top cavity 607 that allows to go from a state depicted in FIG. 6A to a state depicted in FIG. 6B the may be achieved by increasing pressure in bottom cavity 605, by reducing pressure in top cavity 607, or both. As noted above, a cartridge may be equipped with both elevated pressure and reduced pressure (relative to the atmosphere) lines. Elevated pressure and/or reduced pressure in the respective cavities are created through these lines connected to the cavities. Furthermore, pressure inside external cavity 609 may be adjusted to push on liquid containing bag 608 to ensure its puncture and/or to ensure adequate displacement of the liquid from bag 608. After bursting, the liquid may be delivered to top cavity 607, which can be connected to other chambers on a cartridge by one or more fluidic channels. In some implementations, air in the top cavity 607 is removed from the liquid, e.g., by moving the released liquid to a fluidic stop and venting out the air. Examples are described above with respect to FIG. 3. In this manner, the liquid can be delivered to a sensor well or other destination without bubbles. Top cavity 607 may be generally circular or teardrop shaped to help prevent bubble formation.

The pneumatic rupture mechanism 600 described above minimizes possibility of premature rupture of bags. Spike 612, whether floating or attached to flexible membrane 610, has very little inertia and generally cannot accidentally trigger rupture by random external forces exerted onto the cartridge, such as shaking, drops, and other such forces commonly occurring during transportation and use of the cartridge. Furthermore, fluidic extraction from bags is more controllable with pneumatic rupture mechanisms in comparison, for example, with mechanical rupture or mechanical displacement mechanisms. Since a pneumatic rupture mechanism moves a spike into a bag, instead of pushing the bag against the spike, the pressure build ups in the bag can be substantially reduced. This can prevent uncontrolled and premature rupture of bags. Additionally, during fluidic extraction, the spike can be lowered and moved away from the rupture point to provide a more open fluidic passage. Approaches that rely on a frangible seal between the bag compartment and the reagent outlet may also need sophisticated travel and/or force controlled systems to drive the seal to rupture.

Another advantage is to the devices described herein is reducing the complexity of the device manufacturing processes. Approaches that rely on assembling a bag against a spike, such that the bag can later be pushed against the spike, can be challenging to perform without premature rupture. For the frangible seal approach, the bag manufacturing process itself presents a challenge.

Pneumatic rupture mechanism 600 may be used to rupture bags containing any type of fluids, such as substrate, wash, and reporter systems. Fluids are stored in bags that are sealed prior to actuation of corresponding pneumatic rupture mechanisms. Bags may be made from metalized plastic materials, such as low density polyethylene (LDPE) metalized with aluminum.

In certain implementations, an adhesive is provided at least at the interface between support 606 and liquid containing bag 608. This adhesive may be used to seal the interface and to prevent the liquid from escaping into external cavity 609 and to prevent any gas or liquid flow between external cavity 609 and top cavity 607. As such, external cavity 609 and top cavity 607 may be kept at different pressure levels, which may be used to assist in discharging or puncturing liquid containing bag 608. Some examples of adhesives include acrylic based adhesives.

Figure 6C:
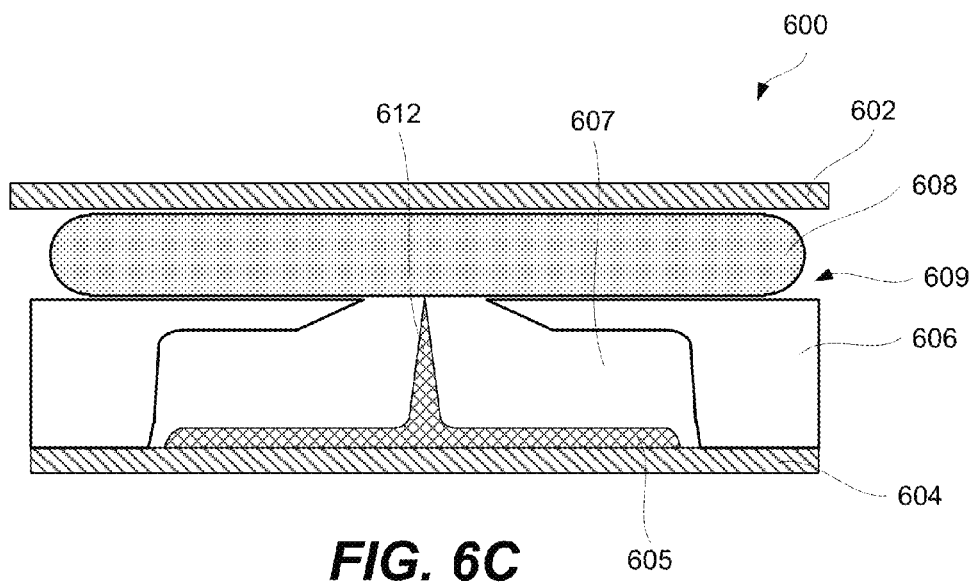
Figure 6D:
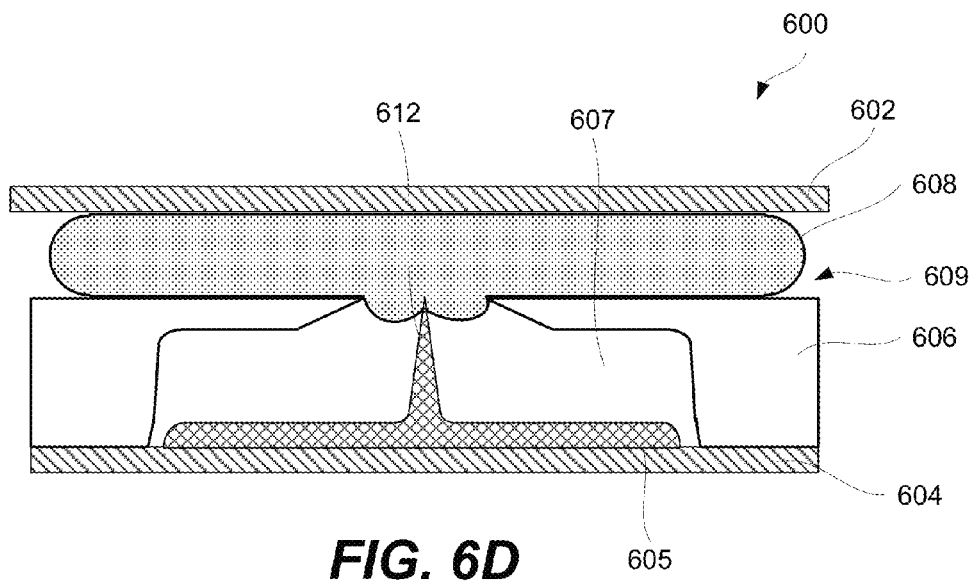

FIGS. 6C and 6D illustrate a pneumatic rupture mechanism according to another implementation. In this example, pneumatic rupture mechanism 600 includes a spike 612 fixed to bottom plate 604. As in the examples shown in FIGS. 6A and 6B, a portion of liquid containing bag 608 is exposed to a cavity 607. In this example, a vacuum may be drawn in cavity 607 to pull liquid containing bag 608 onto spike 612, thereby rupturing the bag 608. In any of the above examples, rupture and liquid delivery to the sensor well may be separated in time, for example as described above with reference to FIG. 3. This allows greater control over liquid delivery.

Aspects of the cartridge and fluid delivery system described herein include multi-layer microfluidic layers including a monolithic membrane layer and liquid and pneumatic chambers and channels on both sides of the monolithic membrane layer. Examples are discussed below with reference to FIGS. 5C and 6E, which depict a diaphragm valve and a bag rupture mechanism, respectively, in a multi-layer stack.

Figure 5C:
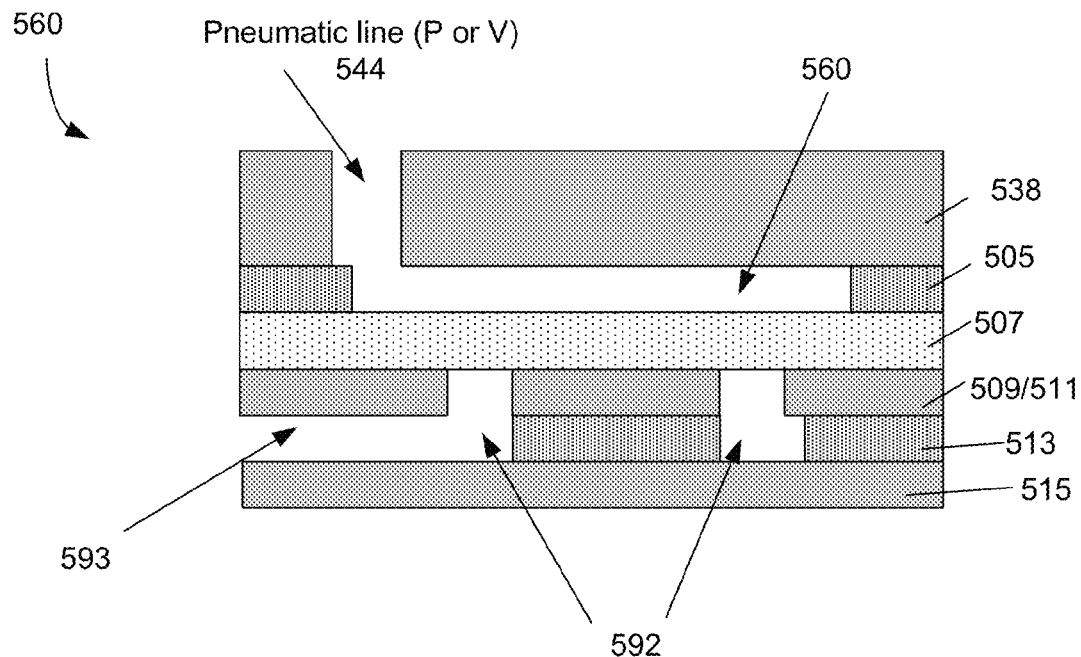

FIG. 5C shows another example of a diaphragm valve that may be used in accordance with various implementations. Layer 538 can be, for example, an airline plate as shown in FIG. 2A described above. Pneumatic chamber or channel 560 can be formed in a layer 505, such as layer 405 in FIG. 4B, that abuts a membrane 507 and can be connected to a pneumatic port or line 544 in layer 538. The valve is depicted closed; when open, fluid can pass through fluidic channel 593 using vias 592. Vias 592 can be formed in one or more layers 509/511 such as 409/411 described above with respect to FIGS. 4D and 4E. Fluid channel 593 can be formed in a layer 513 such as layer 413 described above with respect to FIG. 4F and further defined by a layer 515 such as layer 415 described above with respect to FIG. 4G. In the example of FIG. 5C, when pressure is applied, the membrane 507 is pushed against vias 592, closing the valve (shown). When vacuum is applied, the flexible membrane 507 is lifted, opening the valve.

FIG. 6E shows an example of a pneumatic rupture mechanism 600 in another region of the same layer stack shown in FIG. 5C. Pneumatic rupture mechanism 600 includes a flexible membrane 507 and spike 612. Flexible membrane 507 separates bottom cavity 605 of mechanism 600 from top cavity 607. Top cavity 607 may be defined by a layer 538 that has an opening through which spike 612 can penetrate. As discussed above, layer 538 can be an airline plate 238 as shown in FIG. 2A. The other layers 505 and 509-515 may correspond to layers shown in FIG. 4A as indicated with respect to FIG. 5C. Pressure and/or vacuum can be applied through pneumatic port or line 644 to reach bottom cavity 605. When pressure is applied, flexible membrane 507 is pushed against floating spike 612, which protrudes out of the injection molded layer 538 to puncture and rupture reagent bag (not shown). When vacuum is applied, the flexible membrane 607 is flexed down, with the spike 612 at the down position. When the bag is rupture, liquid is released into cavity 607, from which it can enter one or more microfluidic channels (not shown) as described above, for example, with respect to FIG. 3. In particular, the liquid can be routed to a sensor well on the opposite side of the membrane through a via (not shown) that passes through the membrane 507.

Notably, the membrane 507 can be pneumatically actuated on either side as shown by comparing FIGS. 5C and 6E.

Pressure and/or vacuum lines may cross the membrane as appropriate, as shown in FIG. 6E. Similarly, fluid may be routed on both sides of the membrane as well as between opposing sides of the membrane.

According to various implementations, various types of sensors may be used in accordance with aspects of the description provided herein. While the below description refers chiefly to sensors that generate electrochemical signals, the sample and/or reagent storage and delivery mechanisms described above may be utilized with other detection modalities including but not limited to optical, colorimetric, luminescent, fluorescent, photometric, and transmittance-based systems.

Electrochemical sensing devices described herein can include one or more electrochemical cells, each including working and counter electrodes. The working electrode of each electrochemical cell can be independently functionalized, for example, for sandwich ELISA or other assay. In this manner, any number of different, independent assays may be performed from a single sample. An electrochemical signal generates current in proportion to the amount of target present in the sample. Current between the working and counter electrodes of each cell can be measured, and in some implementations, compared to a separate electrode, if present. The reader converts the change in current to the clinical units of measure for each assay and displays it to the user.

In some implementation, the working electrodes can include, for example, a conducting carbon pad having carbon nanotubes (CNTs) deposited thereon. Methods for functionalizing CNTs for working electrodes are described in U.S. Pat. No. 7,955,559, titled "NANOELECTRONIC ELECTROCHEMICAL TEST DEVICE," incorporated by reference herein.

Figure 7A:
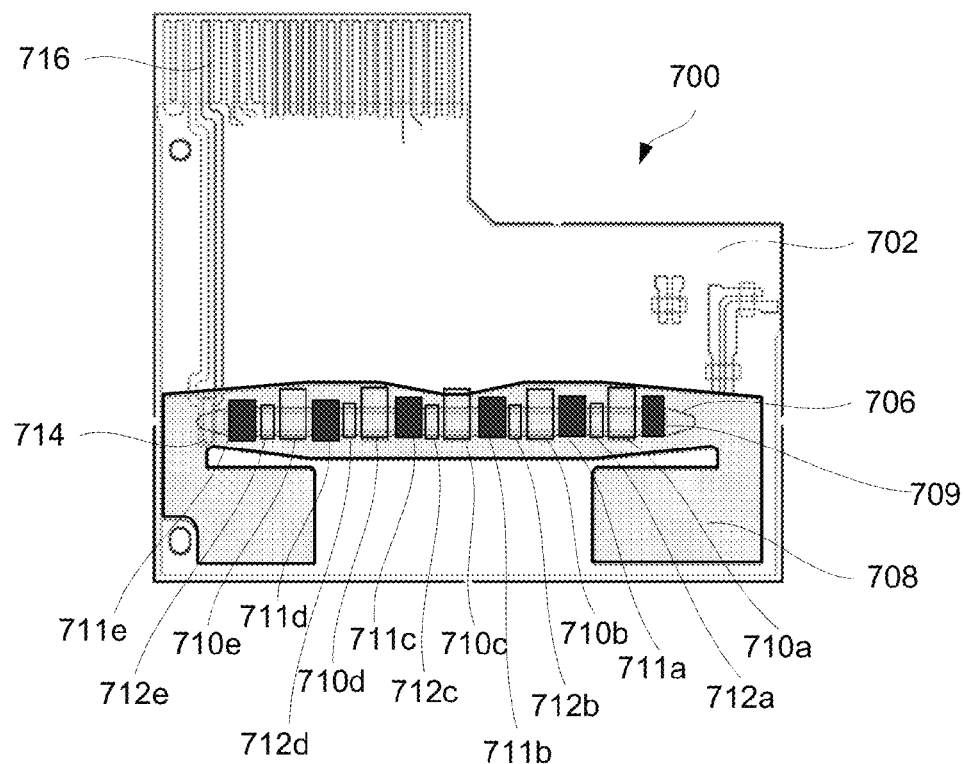
FIGS. 7A and 7C are schematic illustrations of examples of sensing assemblies in accordance with various implementations.

FIG. 7A is a schematic illustration of a sensing assembly 700 that may be used in accordance with certain implementations. Sensing assembly 700 is an example of a sensing assembly 234 incorporated into a cartridge 200 as shown in the example of FIG. 2A. Sensing assembly 700 may be formed on a base sheet 702 by screen printing various components. Base sheet 702 may be made from a polyester-containing material or other appropriate chemically inert material. In certain implementations, the thickness of base sheet 702 is between about 3 mil and 15 mils, for example, about 7 mils.

Figure 9A:
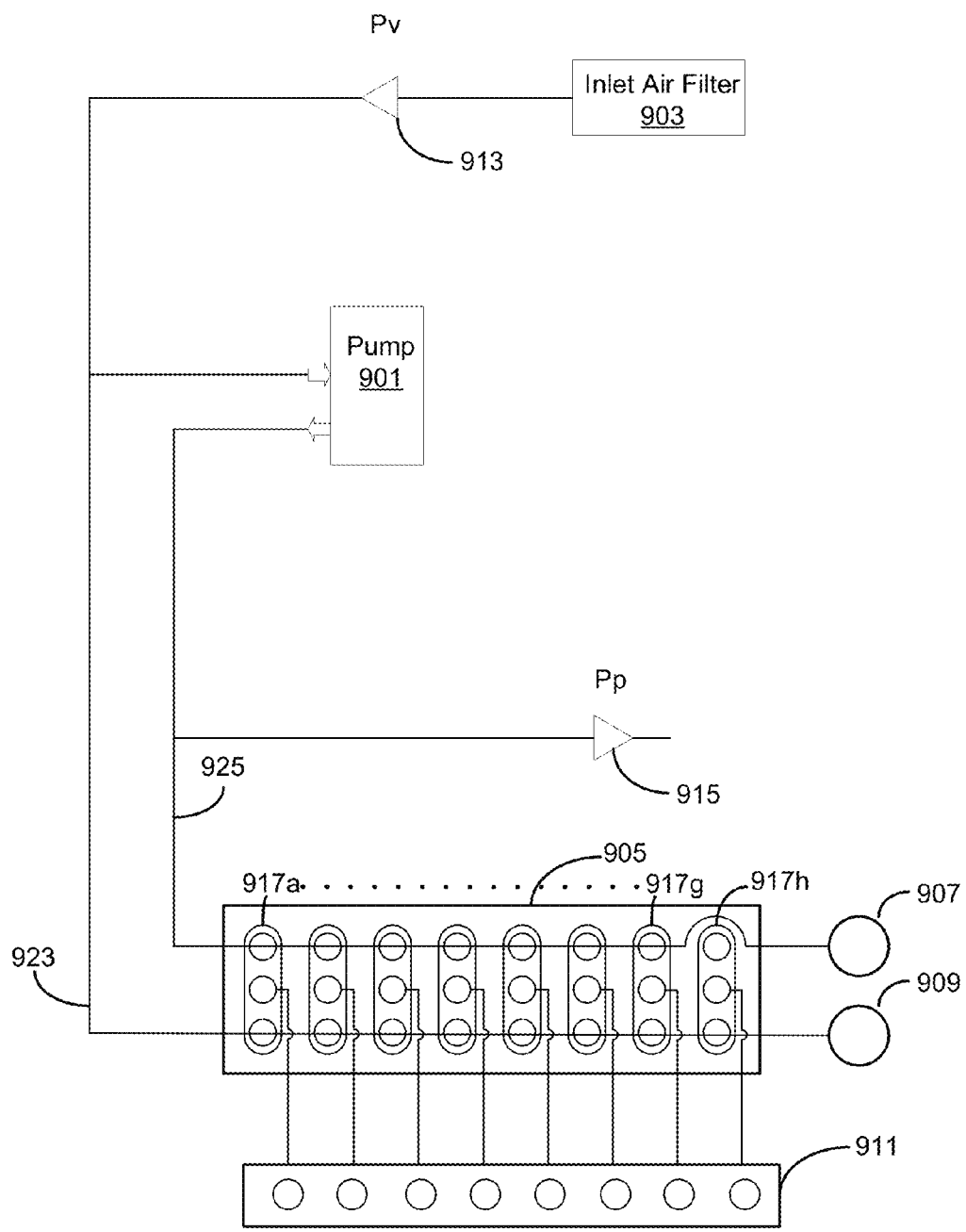
FIG. 9A shows a block diagram of a pneumatic system according to various embodiments.
Figure 9B:
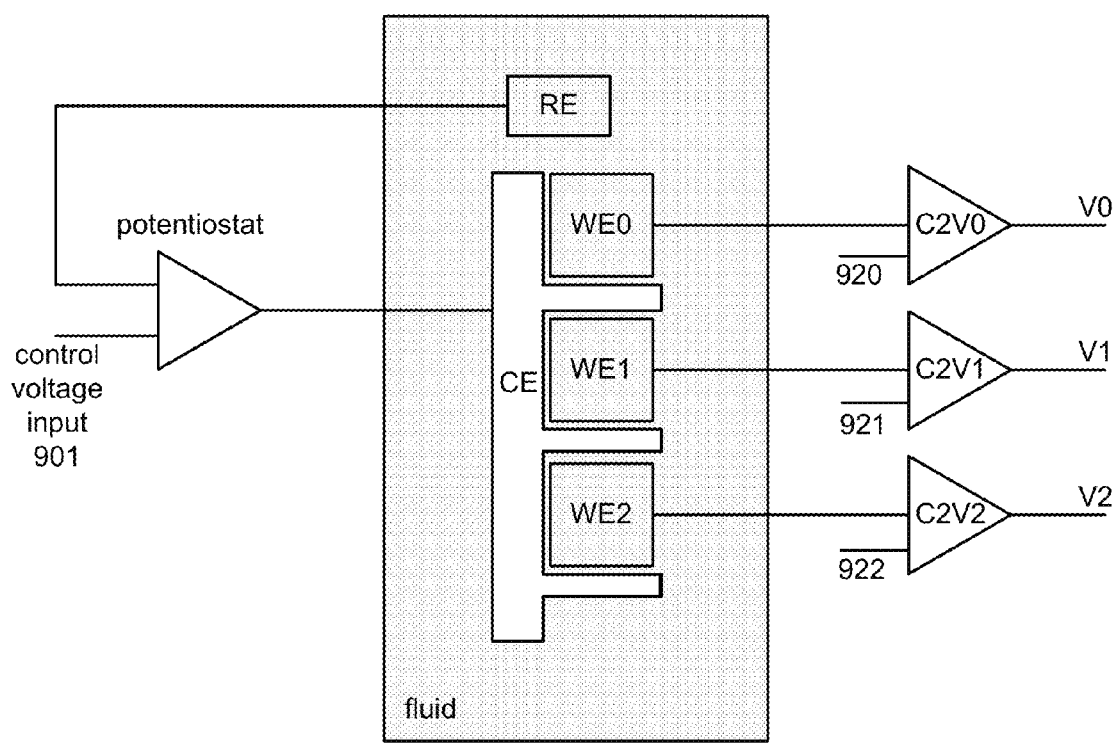
FIG. 9B shows a schematic example of a system for electrochemical testing including a potentiostat.

Components of sensing assembly 700 on base sheet 702 can include working electrodes 710$a$-710$e$, counter electrodes 711$a$-711$e$, reference electrodes 712$a$-712$e$, thermocouple 714, and heater 708. Conductive lines 716, some of which are not shown in FIG. 7A for clarity, extend from each electrode to the top of the sensing assembly 700 for electrical connection to the reader. Each pair of working and counter electrodes 710$a$ and 712$a$, 710$b$ and 712$b$, 710$c$ and 712$c$, 710$d$ and 712$d$, 710$e$ and 712$e$ forms an electrochemical cell and may be used for a different assay. Reference electrodes 711$a$-711$e$ may or may not be present according to the desired implementation. In some implementations, a single reference electrode may be used in turns for multiple working electrodes. An example of such a configuration is shown in FIG. 9B, below. Also, in some implementations, if separate reference electrodes are used, the signals from reference electrodes 711$a$-711$e$ may be tied together on the cartridge or in the reader. For example, the voltages from multiple parallel reference electrodes may be averaged.

The electrodes are at least partially in sensor well region 706, which may be or face a microfluidic channel. Such a microfluidic channel can be defined by, for example, one or more layers of a microfluidic layers as described above with reference to FIG. 2B and FIGS. 4A-4H. All electrochemical cells are exposed to the same continuous liquid film in a microfluidic channel that is or can be open at either end of the sensor well region. Any number of independent electrochemical cells may be present according to the desired implementation.

Different types of inks that can be used for constructing these components include nickel (Ni)-containing ink, silver (Ag)-containing ink, carbon (C)-containing ink, silver-silver chloride (Ag/AgCl)-containing ink, and dielectric-containing ink. All inks with exception of the dielectric-containing ink generate conductive elements, while dielectric-containing ink results in insulating structures and typically used as a blanket coating over other inks All inks can be printed in sequence by standard screen printing techniques following by a curing step, such as infrared, thermal, UV, or other types of curing. In some implementations, working electrodes 710$a$-710$e$ may be carbon, reference electrodes 711$a$-711$e$ may be silver chloride, and counter electrodes 712$a$-712$e$ may be silver.

In certain implementations, all components other than heater 708 are printed on one side of base sheet 702, while heater 708 is printed on other side of base sheet 702. As such, base sheet 702 acts as an electrical insulator between, for example, the electrodes and heater 708. At the same time, base sheet 702 is sufficiently thin that it provides sufficient heat conductivity between heater 708 and sensor well region 706. Furthermore, base sheet 702 may perform heat distribution functions to provide more uniform heat transfer.

Because the heater is separated from the sensor well only by a thin base, heating the liquid in the sensor well is very efficient. In addition, because a screen printed heater have very small mass, it takes very little energy to generate sufficient heat. For example, the heater may be a 0.5 Watt or 1 Watt heater and can heat a sensor well up to 100° C. The thermal efficiency is particularly advantageous for battery-powered point-of-care applications where size and weight requirements place constraints on available battery capacity. Note that there may be other temperature constraints in various implementations, such as a delamination temperature. For example, some adhesives such as those described above with respect to FIG. 4A may fail and delaminate at around 80° C. Higher temperature-rated adhesives may be used in implementations in which the higher temperatures are desired.

Heater fabrication may include certain blends of inks to achieve a specific electrical resistance of the heater for a given area. For example, carbon and silver inks may be blended to give a resistance of 10 ohms. In some implementations, the heater may be configured to provide uniform heating to the sensor well.

Figure 7B:
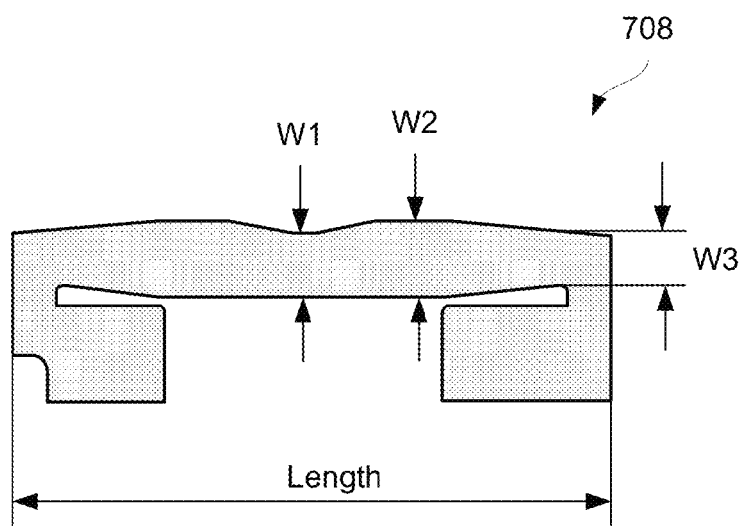
FIG. 7B is a schematic illustration of an example of a screen-printed heater in accordance with various implementations.

FIG. 7B provides an example of a heater shaped to account for uneven heat losses along the sensor well length and uneven power dissipation within the heater element. Heater 708 may have a narrow center portion (W1), a wider expansion (W2) followed by narrower end portions (W3) that end past the sensor well. As such, both ends of the wells coincide with wider expansions (W2) of heater 708 to compensate for additional heat loss in these areas. In certain implementations, both expansions are at least 10% wider, e.g., about 20% wider that the center portion. In one implementation, center portion has a width of about 5.14 millimeters and expansions have widths of about 6 millimeters, while the end portions have widths of 3.98 millimeters. This heater may be about 47.37 millimeters long. Heat generation is generally proportional to the width of the heater. In implementations that employ multiple sensor wells, e.g., as in FIGS. 2C-2E, a single screen-printed heater may be used to heat multiple wells simultaneously.

The heater may be coupled and controlled by a thermocouple to provide more precise temperature. In certain implementations, the operating temperature range is between about 20° C. and 50° C. or, between about 25° C. and 45° C., about 40° C. The operating temperature is designed to be above an ambient temperature of any point-of-care setting. This allows sensing to be carried out without the need for cooling. Electrochemical sensors provided in the sensor well may be calibrated to this temperature range. Precise temperature control of the sensor well enables more sensitive measurements within the channel. In some implementations, the point-of-care systems provided herein are configured for active temperature control, as discussed further below.

Figure 7C:
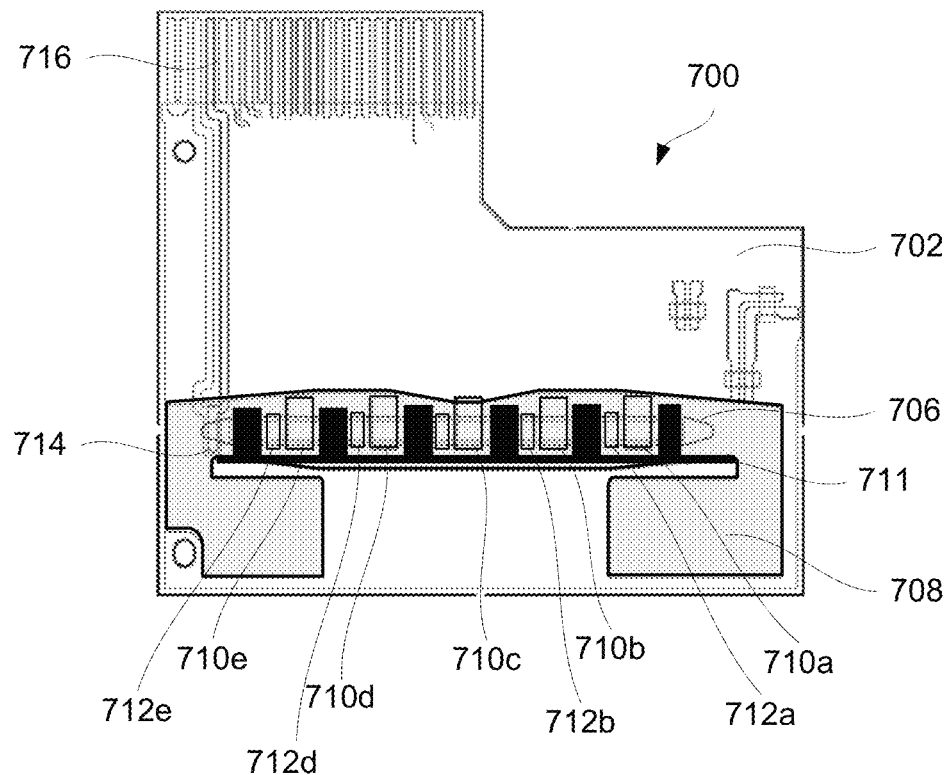

In multiplexed electrochemical assays, the electrodes can be arranged in any appropriate fashion. In some implementations, the electrodes are arranged along the length of the channel, with the reference electrodes 712a-712e located adjacent the working electrodes 710a-710e. Counter electrodes 711a-711e, along with electrode 709 can be spaced such they provide a uniform electrical field along the length of the sensor well region 706. In some implementations, multiple electrochemical cells can share a counter electrode. This reduces the number of electrodes and leads required for multiplexed assays. FIG. 7C shows an example of a sensor having working electrodes 710a-710e, reference electrodes 712a-712e, and a common counter electrode 711. In the example of FIG. 7C, the common counter electrode 711 is a bar along the length of the sensor well 706, with fingers interdigitated with the working electrodes 710a-710e and reference electrodes 712a-712e. The common counter electrode 711 can also have other shapes and arrangements. For example, the common counter electrode 711 may be a simple bar extending along and contacting fluid in the sensor well 706. Unlike the arrangement depicted in FIG. 7A, which uses three traces per electrochemical cell (one each from the working, reference and counter electrodes), the arrangement in FIG. 7C uses two per electrochemical cell and one from the common counter electrode 711.

Figure 7D:
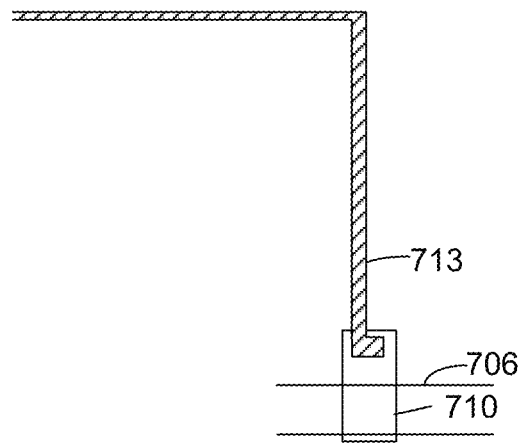
FIG. 7D is a schematic illustration of an example of a conductive trace and carbon electrode connection in accordance with various implementations.

In some implementations, the conductive traces providing electrical connection to an interface region of the sensing assembly 700, such as interface region 106b in FIG. 1A, are Ag traces. In some implementations, an Ag trace connected to a carbon working electrode as shown in FIG. 7D. In the example, of FIG. 7D, Ag trace 713 contacts only a portion of working electrode 710 outside of the sensor well region 706 to prevent the trace from contacting any liquid and interfering with electrochemistry of the assays. In the same or other implementations, the Ag trace 713 may be contact the underside of the working electrode 710. According to various implementations, the portions of the counter electrodes 711a-711e or common counter electrode 711 that are exposed to the sample in the sensor well 706 have surface areas greater than or equal to the corresponding portions of the working electrodes 710a-710e. The reference electrodes 711a-711e may be fairly small to reduce the amount of sample needed.

In some implementations, the heights of the electrodes and conductive traces are fairly uniform and small compared to the total height of the sample channel to provide uniform flow characteristics. For example, for a channel height of 140 microns, electrodes and traces may be on the order of about 8-12 microns. For example, the channel height may be at least 10 times the height of the tallest electrode. According to various implementations, a dielectric ink or other gap fill material may or may not be incorporated into gaps between electrodes. Including a gap fill material can further facilitate providing uniform lateral flow characteristics in the microfluidic channel.

The working electrodes 710a-710e may each have a uniform or varying surface area according to the desired implementation. For example, in some implementations, the area of each working electrode can be based on a desired sensitivity for the particular assay in question. Reducing surface area for assays that can tolerate lower sensitivity and/or need less sample exposure can facilitate increasing the number of assays without a corresponding increase in sensor well and sample volume. Example surface areas of a carbon working electrode can range from about 1 mm$^2$ to about 5 mm$^2$, though electrode sizes outside this range may be appropriate in some implementations.

The sensing assemblies described herein may include one or more controls and/or fluid flow checks. For example, in some implementations in which ELISA is performed, a positive and/or negative control is provided, the positive control to confirm that a known analyte in the sample is detected and a negative control to provide background signal. An example of a positive control for an immunoassay is an anti-mouse antibody that will capture all type of the reporter antibodies derived from mouse antibody. An example of a negative control for an immunoassay is mouse anti-human serum albumin or other antibody non-specific to the reporter and target. Positive and/or negative controls may be used for other types of assays as well. In some implementations, a fluid flow check may include a conductivity check. Moreover, in some implementations, a positive control may also be used as a fluid flow check to confirm whether the sensor well is filled and/or adequate flow past the sensors in the sensor well.

Figure 8A:
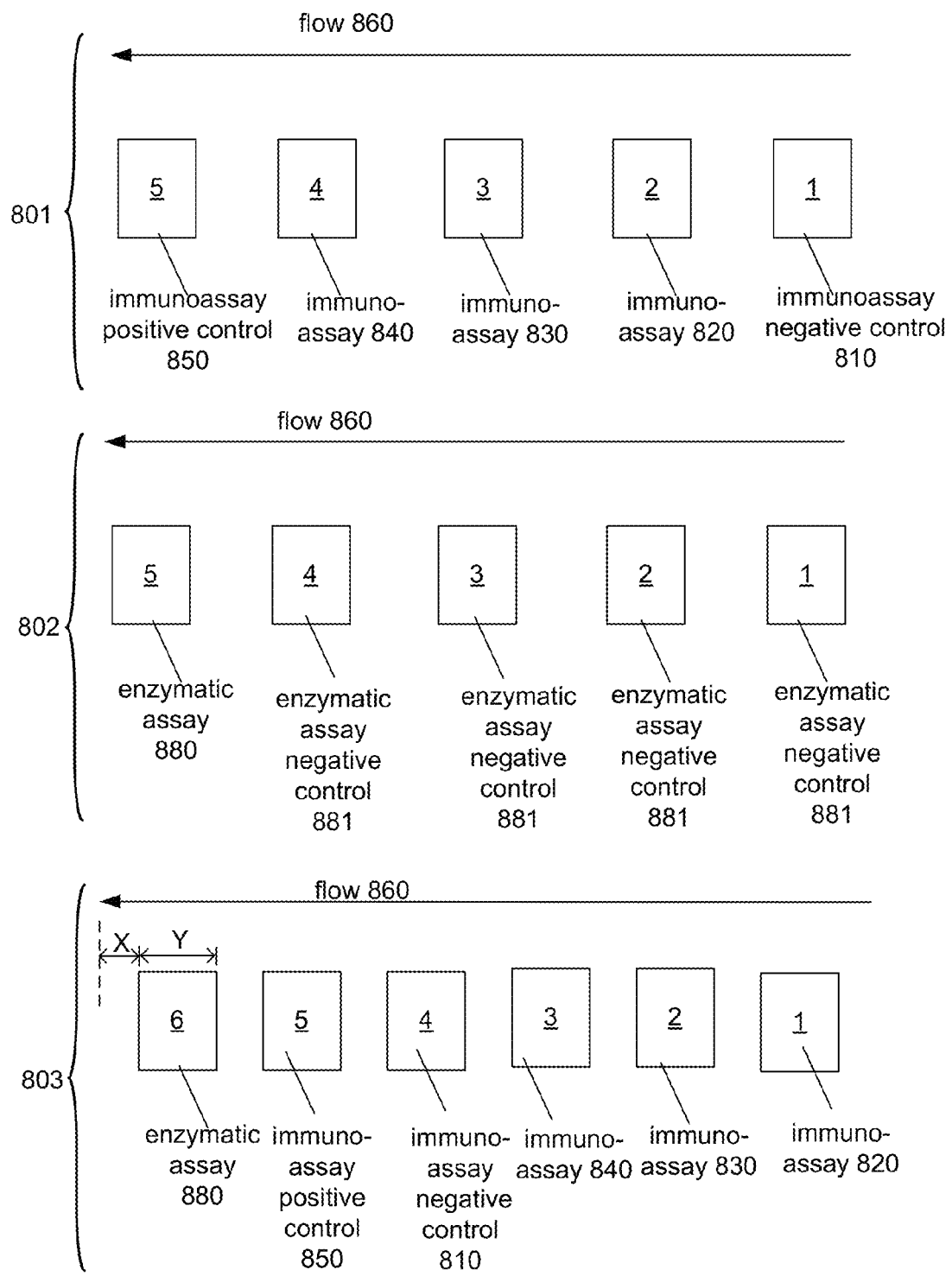
FIG. 8A provides examples of arrangements of electrodes for assays and controls according to various embodiments.

For example, one or more of the electrochemical cells depicted in FIG. 7A can be used as controls. FIG. 8A provides examples of arrangements 801 and 802 of electrodes for assays and controls according to various implementations. If used as a conductivity check, a control can be located furthest along a flow path, such as positive control 850 in arrangement 801 being located furthest along the flow path 860 through the sensor well, though in some other implementations a positive control may be located at the beginning or in the middle of a flow path either in addition to or instead of at the end of the flow path. If inadequate current is generated between the working and counter (and/or reference) electrodes of a positive control and/or conductivity check, the reader may indicate that the card is defective and/or adjust the measurements to reflect the diminished sample or flow. A negative control 810 may be located at any appropriate place, e.g., at the beginning of the flow path 860 in arrangement 801 in arrangement 802, next to the positive control, etc. If current generated between electrodes of the negative control 850 exceeds a threshold current, the reader may indicate that the card is defective.

According to various implementations, a single cartridge for a point of care electrochemical sensor may be configured for one or more enzymatic (non-immuno) assays and immunoassays. Examples of enzymatic assays include assays for glucose, galactose, lactose, glutamic acid, cholesterol, xanthine, hypoxanthine, uric acid, choline, creatinine, acetylcholine, tyrosine, and hydrogen peroxide. In an electrochemical enzymatic assay, one or more enzymes and one or more mediators can be coated on the working electrode. The one or more enzymes will depend on the desired assay, with examples including oxidases (e.g., glucose oxidase, cholesterol oxidase, xanthine oxidase, glycerol-3-phosphate oxidase, choline oxidase), esterases (e.g., cholesterol esterase, acetylcholinesterase), uricase, and kinases (e.g., protein tyrosine kinase). The one or more mediators will depend on the desired assay, with examples including ferrocene, hydroquinone, and derivatives thereof.

In some implementations, an electrode configured for an enzymatic assay (or other assay involving dissolution in the sample of one or more reagents that are coated on the electrode) may be covered with a water-soluble polymer to prevent premature dissolution or being washed away by liquid flowing by. One example of a polymer is polyvinylpyrrolidone (PVP). The presence or amount of soluble polymer may depend on the surface on which the enzymes/mediator is coated: a polymer may not be needed or as needed if the reagents are on surfaces to which they may adhere better e.g., on a carbon electrode (or other appropriate electrode surface) or CNT's. In implementations in which they do not directly coat an electrode surface or CNT, they may have lower adhesion and benefit more from an overlying soluble polymer. One such example is discussed below with reference to FIG. 8B.

In some implementations, in addition or instead of using a water soluble polymer, the "dead" volume in the sensor well past a coated working electrode may be reduced or eliminated, such that relatively little or no liquid washes over the working electrode during fill. In some implementations, this can include placing an enzymatic sensor at the end (furthest along the flow path) of a sensor channel. An example is shown at 802 and 803 in FIG. 8A, in which the enzymatic assay sensor 880 is the last sensor (sensor 5 for arrangement 802 and sensor 6 for arrangement 806) and so has the least amount of liquid initially flowing by as the sensor well fills. Moreover, in some implementations, the available volume past the enzymatic sensor is reduced or eliminated. Referring to FIG. 2B, for example, channel 224 connected to sensor channel 214 may be reduced or eliminated, such that instead of flow stopping at 224b during fill, it stops at or closer to 224a. In some implementations, the distance past the working electrode of an enzymatic assay sensor is no more than a certain fraction of the width of the working electrode. For example, referring to arrangement 803, the working electrode of sensor 6 may have a width Y, with the distance the past working electrode that the sample flows during fill being X. According to various embodiments, X may be between about 0 to 1.5Y, e.g., 0.5Y or 0.1Y. In this manner, the amount of enzyme that may be washed off is reduced.

In some implementations, one or more enzymes and/or mediators may be provided as a solid phase reagent and mixed with the sample prior to delivery to the sensor well, rather than being coated on the working electrode. In one example, this may be done as described above with respect to with respect to an electrochemical ELISA assay in which the sample can be mixed with a lyophilized reporter. While reporter concentration in a sample may be desired to be very precise for the electrochemical ELISA described herein, in some implementations, mediator or other reagent concentration in a sample may be less precise. In one example, an assay is configured to determine the presence/absence rather than quantity of the target, may not need a precise amount of solid phase reagent to dissolve in the sample. Accordingly, in another example, a mediator or other solid-phase reagent may be coated along a channel disposed between the sample inlet and the sensor well, without active mixing and/or de-bubbling performed.

A cartridge may also be configured for one or more non-enzymatic assays in some implementations. As indicated above, in some implementations, a cartridge may be configured for electrochemical ELISA. In general, the technique may use any ligating reagent that can be immobilized on a working electrode along with a detection reagent that will bind specifically and use an enzyme to generate an electrical signal that can be properly quantified. Examples of biomarkers that a cartridge may be configured to assay include, cardiac troponin I (cTnI), myoglobin (Myo), fatty acid binding protein (FABP), prostate-specific antigen (PSA), prostate specific membrane antigen (PSMA), platelet factor-4 (PF-4), interleukin-6 (IL-6), 17 beta-estradiol (17 beta-E2), creatinine, C-reactive protein (CRP), procalcitonin (PCT), brain natriuretic peptide (BNP), creatine kinase-MB (CK-MB), fibrin degradation products (FDP) including D-dimer, interferon-gamma, endotoxin, 1-3-beta glucan, human immunodeficiency virus (HIV), hepatitis C virus (HCV), and herpes simplex virus (HSV).

Figure 8B:
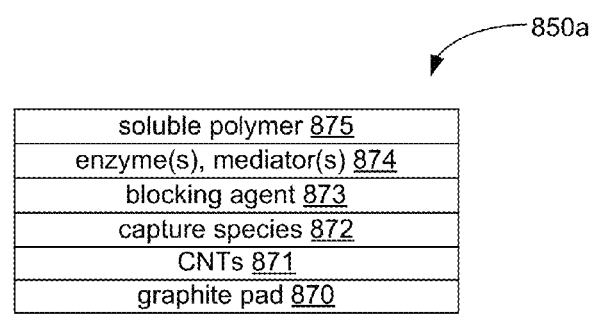
FIG. 8B shows an example of material layers at a working electrode of a sensor used for an enzymatic assay and for a positive control of an immunoassay according to various implementations.

In some implementations, a cartridge may be configured for multiplexed assays, including at least one assay involving capture species (e.g., ELISA) and at least one non-capture assay (e.g., enzyme mediated glucose assay). In some implementations, an electrochemical cell may be configured for a capture species-based assay or control and a non-capture assay. FIG. 8B shows an example of a working electrode 850a for a positive control, e.g., as shown at 850 in FIG. 8A. In the example of FIG. 8B, working electrode 850a includes a graphite pad 870, e.g., a screen-printed graphite pad, CNTs 871 functionalized with antibodies or other capture species 872 selective to a known target in the sample and a blocking agent 873 to prevent non-specific binding. Components 870-873 can provide a positive control, e.g., for ELISA or other immunoassay. In the example of FIG. 8B, one or more enzymes and mediators 874 are also included on working electrode 850a, deposited over the functionalized CNTs and a hydrophilic blocking agent. A soluble polymer 875 may optionally be included as described above to control dissolution. In this manner, the positive control 850 for an immunoassay is also is an active electrochemical cell for a glucose or other non-immuno-based assay. In some implementations, a separate blocking agent 873 may not be used, with the enzyme(s)/mediator(s) 874 acting as a blocking agent.

An arrangement as in FIG. 8B can be used to increase the number of assays for a given number of electrodes in an electrochemical sensing assembly. In some other implementations, two or more sensor channels or wells may be provided. For example, immunoassays may occur in one sensor channel and non-immuno enzymatic assays in a separate channel. Examples are described above with reference to FIGS. 2C-2E.

Returning to FIG. 8A, each of sensors 1-5 can be used both for analyte detection/quantification as well as a control in different phases of sensing. For example, referring to arrangement 802, during an enzymatic assay 880 using sensor 5, sensors 1-4 can each act as an independent negative control 881 for enzymatic assay 880. The same five sensors can then each be used in one or more immunoassays, with sensors 2, 3, and 4 used for detection/quantification in immunoassays 820, 830, and 840, sensor 5 used as a positive control for the immunoassays, and sensor 1 used as a negative control. In some other implementations, sensor 5, used for the enzymatic assay, may be used as a negative control for the immunoassay.

In some implementations, a separate sensor may be used for positive/negative control of the immunoassay. Referring to arrangement 803, sensor 6 may be used for enzymatic assay 880, with sensors 5 and 4 used as the positive and negative controls, respectively, for the immune-assay and sensors 1, 2, and 3 used for immunoassays 820, 830 and 850. In this case, electrode 850a in FIG. 8B for sensor 6 may include only graphite pad 870, optionally CNTs 871, one or more enzymes and mediators 874, and optionally a soluble polymer 875 to control dissolution.

In some implementations, the cartridge includes a panel of assays including or detecting biomarkers implicated for certain conditions or otherwise related. Examples include a critical cardiac panel including cTnI, Myo, FABP, and creatinine; a brain trauma panel including S100 calcium binding protein (S100B), myelin basic protein (MBP) and/or other biomarkers for traumatic brain injury (e.g., TBI-1 or TB1-2), an infectious disease panel including CRP, PCT, interleukin 6 (IL-6) and interferon-gamma, biomarkers for influenza A/B, Lassa fever, and Ebola virus; a metabolism/miscellaneous panel including retinol binding protein 4 (RBP-4), C-peptide, glucose, human chorionic gonadotropin (hCG), and PSA; a cardiac and respiratory stress panel including BNP, CK-MB, D-dimer, and high sensitivity CRP (hsCRP); a cardiac health and congestive heart failure panel including BNP and troponin; a stroke panel including FABP, MBP, and neuron-specific enolase (NSE) and/or other biomarkers for stroke; a sepsis panel including CRP, PCT, IL-6, lactate, endotoxin, and 1-3 beta glucan. Cartridges may be customized for certain uses. For example, a critical cardiac cartridge may be kept in ambulances and emergency departments. Cardiac and respiratory stress cartridges may be used in emergency departments, urgent care facilities, and small labs. Sepsis cartridges may be used in emergency departments, ambulances, and intensive care units. Brain trauma cartridges may be used in ambulances, emergency departments, and urgent care facilities. Stroke cartridges may be used ambulances, emergency departments, urgent care facilities, and intensive care units, etc. Any type of cartridge may be used in the field.

In some implementations, the cartridges described herein include a thermocouple. FIG. 7A, above, depicts thermocouple 714 integrated on the sensing assembly 700 positioned to measure the temperature in sensor well 706. In some implementations, a thermocouple may be used to provide active control over the sensing well temperature via a heater such as heater 707 in the example of FIG. 7A.

Provided herein are screen-printed thermocouple devices. While the screen-printed thermocouples are described below in the context of a cartridge for a portable reader, they may be incorporated into other devices as well, including other types of sensors. Standard thermocouples may be formed when two metals with dissimilar Seebeck coefficients are joined together. The metals are joined by spot welding or similar metal joining techniques. Common thermocouples may use alloys, such as chromel or constantan, and/or pure metals such as copper and iron, which have large Seebeck coefficients of opposite polarity. While these materials can make good thermocouples because they generate relatively large voltage differences, it is very difficult to screen-print thermocouples using these materials.

Screen printing processes push ink through a patterned mesh to form features. Metallic inks are viscous suspensions of metallic particles containing a carrier solvent that is dried off after printing. A first challenge is creating ultra-fine metal particles and keeping them in suspension during the printing process. A second significant challenge is that the ink may remain conductive so that an electrical connection can be made between two disparate inks. For screen-printed thermocouples, the joint is formed by one ink printed on top of the second, thus oxidation is a problem. Copper is one of the more common screen-printed metallic inks, however it easily oxidizes.

Implementations described herein include screen-printed thermocouples that include a carbon-metallic thermo-electric junction, e.g., a silver-carbon (Ag—C) or nickel-carbon (Ni—C) junction. Implementations described herein also include thermocouples including silver-nickel (Ag—Ni) thermo-electric junctions. In testing, screen printed Ag—Ni thermocouples were determined to have a Seebeck coefficient of about 14 µV/K for Ag—Ni and screen printed Ni—C thermocouples were determined to have a Seebeck coefficient of 17 µV/K. The Seebeck coefficient depends on the ink and drying conditions, so the coefficients may vary, but these values demonstrate the feasibility of screen-printed thermocouples using a variety of inks, include Ag, Ni and C.

As the conducting traces and contact pads for thermocouple do not affect the performance of the thermocouple, conducting traces and contact pads and may be selected best for the mechanical and electrical reliability, i.e. scratching resistance and low contact oxidization. In some implementations, Ag leads may be used, e.g., with Ni—C thermocouples. Ag—C thermocouples may be used in some implementations in which carbon and silver inks are used for electrodes and leads as described above with reference to FIG. 7A.

The screen-printed thermocouples described herein can be made with high reproducibility with little added expense as precision thermocouples do not require precise geometry. Inks can be made in very large batch sizes, sufficient to print thousands of thermocouples. In some implementations, a small number of these thermocouples can be tested to determine the specific Seebeck coefficient for that lot based on the specific ink used for the lot. In some implementations, the thermocouples provided herein can be fabricated on very thin substrates. In some implementations, the substrates may be only 3 mils thick. In implementations in which the thermocouples are incorporated into a sensing assembly as described with reference to FIG. 7A, they may be printed alongside screen-printed electrodes.

The screen printed thermocouples described herein can provide active temperature control during sensing, allowing precise and uniform measurements for a variety of cartridges and sensing environments.

As indicated above, in some implementations, the cartridge is configured to perform electrochemical sensing. Further, the cartridge may be configured to perform non-capture electrochemical detection and capture-based electrochemical detection using a single sample and sample inlet, a common plasma filter, and a common heater. These features can enable the cartridge to be small and portable. Still further, the same fluid delivery and detection systems may be used.

Figure 10A:
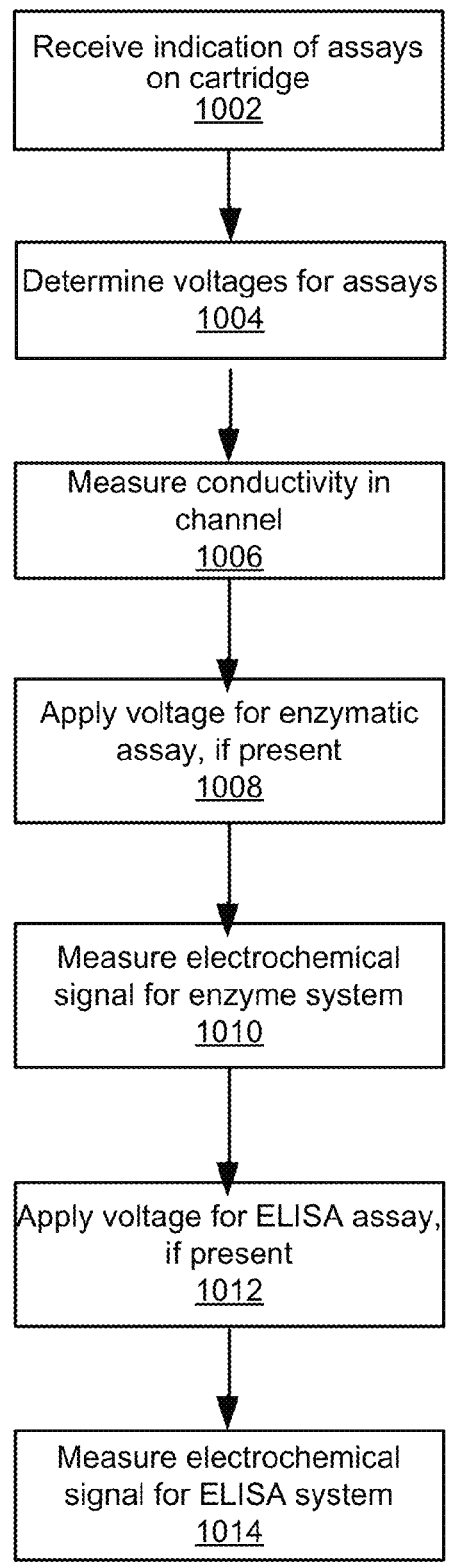
FIG. 10A is a flow diagram illustrating operations in an example of a method of electrochemical sensing.

FIG. 10A is a flow diagram illustrating operations in an example of electrochemical sensing. First, an indication of the assays on a cartridge is received by the reader (1002). In some implementations, the cartridge may include a bar code or other identifier that is read by the reader. In some implementations, for example, a cartridge may include a screen-printed closed circuit having a resistance uniquely associated with a particular type of cartridge (cardiac panel, sepsis panel, etc.). In some implementations, a user may enter or confirm card identification via a user interface. Once the assays are identified, the reader can determine the voltages used for the particular enzyme and/or ELISA assays (and/or other electrochemical assays) on the cartridge. (1004) For example, a particular enzymatic glucose assay may be run at 300 mV. In another example, many ELISA assays are run between 0 and 50 mV. In some implementations, once the cartridge is identified, stored information including the voltages associated with the cartridge assays is retrieved from one or more storage mediums on the reader. In some implementations, a user may be able to enter, modify and/or confirm voltages. At some point prior to sensing, conductivity in the channel can be measured (1006). Any appropriate method of measuring conductivity can be used, including applying a sine, step, or square wave through the counter electrode to induce current in the fluid that is measured at the working electrode. In some implementations, block 1006 can involve detecting current at the last or all of the electrodes in a channel to confirm that the sensor well is filled.

Next, the voltage for an enzymatic assay (if present on the cartridge) is applied (1008). In some implementations, block 1008 occurs during sample incubation for ELISA assays, either in the same or a different channel than the ELISA sensors. If performed in the same channel, the voltage applied in block 1008 may or may not be applied to the ELISA sensors as well as the enzymatic assay sensor. As discussed with reference to FIG. 9B, the voltage at each sensor may or may not be independently controlled according to the particular implementation. The electrochemical signal for the enzyme system is then measured (1010), providing information about the presence and/or concentration of the target analyte in the sample.

Block 1010 can involve any appropriate electroanalytical method including but not limited to chronoamperometry or other amperometric technique, electrochemical impedance spectroscopy, square wave voltammetry, linear sweep voltammetry, and differential pulse voltammetry. In some implementations, block 1010 involves amperometric detection in which the potential is held constant while the current measured. Other techniques may be advantageously employed depending on the particular system. If more than one enzymatic assay is to be performed, blocks 1008 and 1010 can be performed for each enzymatic assay, either sequentially or in parallel, depending on the particular implementation. Next, voltage is applied for an ELISA assay if present on the cartridge. (1012). As discussed above, wash and substrate liquids can be added to the sensor channel between blocks 1010 and 1012. The electrochemical signal for the ELISA system is then measured (1014). Any of the techniques described above with respect to block 1010 may be employed. In some implementations, block 1014 involves amperometric detection in which the potential is held constant while the current measured. Blocks 1010 and 1014 can involve the same or different techniques. If appropriate, the same technique may be employed for simplicity. If more than one ELISA assay is to be performed, blocks 1012 and 1014 can be performed for each enzymatic assay, either sequentially or in parallel, depending on the particular implementation.

in addition to controlling electrode voltage for electrochemical detection (e.g., at blocks 1008 and 1012), the voltage of a working electrode can be controlled at various other times during sensing. For example, sample incubation may involve setting the working electrode potential to enhance electromigration and/or mass transport characteristics of the target species in the sample to the working electrode. In another example, the voltage of the working electrode may be swept to precondition the electrode prior to sensing. For example, if a counter electrode is expected to change by 30 mV during electrochemical measurement of TMB to compensate for signal generated by the TMB, the working electrode voltage may be scanned +/−60 mV prior to measurement of the TMB. In this manner, any signal that occurs due to contamination on the working electrode will occur prior to sensing, e.g., during incubation.

Figure 10B:
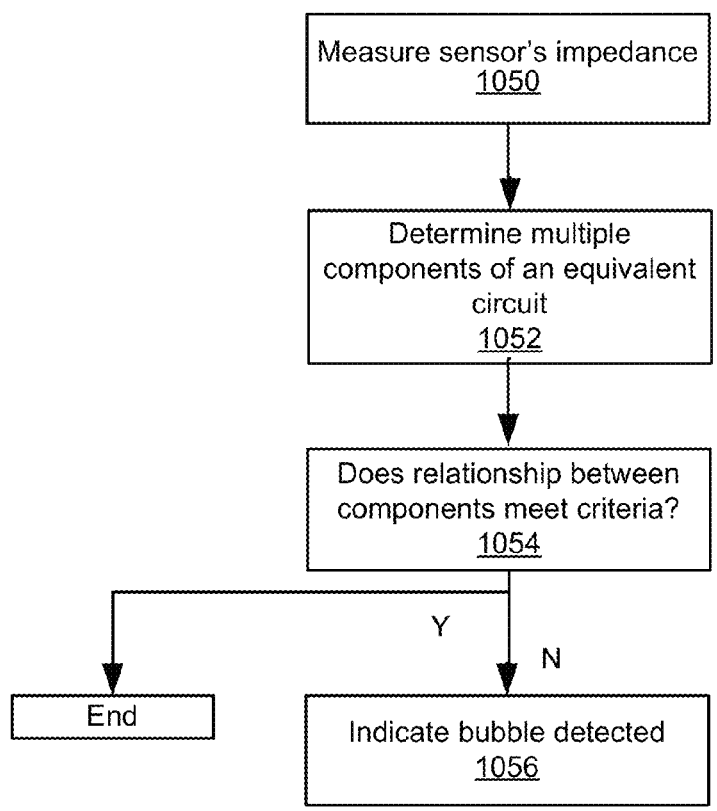
FIG. 10B is a flow diagram illustrating operations in an example of a method of bubble detection in a sensor well.

Also provided are methods and apparatus for confirming that electrodes are in good contact with liquid analyte in an electrochemical sensor and that the sample does not contain any air bubbles. In some implementations, the methods are based on an impedance measurement of the sensor. FIG. 10B shows a flow diagram illustrating operations in an example of a method of bubble detection in a sensor well. The method begins at block 1050 with measuring the sensor's complex impedance value. This can be done by using AC current at one or more frequencies and measuring, for example, the current magnitude and phase shift with respect to the phase of the applied voltage. A multi-component equivalent circuit model is calculated at block 1052. For example, in some implementations, the series resistance Rs and the series capacitance Cs can be determined, where Rs mainly represents the resistance of the electrolyte and Cs mainly represents the liquid-electrode interface capacitance. Both of these components depend on the composition of the analyte and on its contact with the sensor electrodes. Cs and Rs can be determined from the impedance, e.g., as described in Agilent Impedance Measurement Handbook, 4th Edition. Agilent Technologies, 2009, incorporated by reference herein. The detection of bad or questionable samples under the method described here is done based purely on electrical measurements, by extracting and processing information about these components.

The method continues with determining if the relationship between components meets criteria. For example, using Cs and Rs, the method assumes that the relationship between Cs and Rs is affected by air bubbles. For a particular system, an empirical relationship between Cs and Rs components of an impedance measurement may be established, as well as the range acceptable values for each component. These conditions may serve as the acceptance criteria for a sample. In one example, the parameters k0 and k1 and maximum acceptable error ($\epsilon$max) in the linear relationship $CS=k0+k1*RS+\epsilon$ are established experimentally using regression for given sensor geometry and analyte type. The CS-RS relationship is considered acceptable (and in some implementations, the sample is considered acceptable) if and only if $|C_S-k_0-k_1*R_S| \leq \epsilon_{max}$.

The impedance-based method described above detects air bubbles in most instances, though there may be unusual instances in which a bubble may be attached partly to the electrode and partly to the wall of the chamber in such a way that the complex impedance will match that of a sample without any air bubbles whose electrical impedance is higher. Accordingly, a range of values of $R_S$ and/or $C_S$ may be also established, e.g., the sample is acceptable only if Rmin<$R_S$<Rmax and/or if Cmin<$C_S$<Cmax. The $R_S$ and/or $C_S$ criteria may be used in addition to or (in a simplified method) instead of the $C_S$-$R_S$ relationship criteria described above.

Returning to FIG. 10B, if the $C_S$-$R_S$ relationship and/or $R_S$ and/or $C_S$ meet this criteria, the method may end, with the no bubble detection indicated and the sample deemed acceptable. If not, bubble detection may be indicated by the reader at block 1056. In some implementations, the reader indicates that the cartridge is defective and a new cartridge should be used. In some implementations, the reader may adjust a confidence value to the output measurement. In some implementations, the reader may adjust a measurement based on stored calibration information derived from measurements in the presence of bubbles.

For some implementations in which the conductivity of the sample is well regulated, a simplified method involving measuring current may be used. Blood, for example, has fairly uniform conductivity, varying for example, by less than about 10% across patients. FIG. 11A, for example, below shows a measured current for each of five biosensors in a blood sample detection zone. The steady, uniform current of each sensor during sample incubation can indicate that there is no bubble in contact with the sensor. For samples that are not well regulated, e.g., urine, however, multiple components of the impedance measurement can be used.

In some implementations, the electrical impedance may be used to estimate the hematocrit level in blood samples. Since the red blood cells are not conductive, their proportion in the blood sample affects the electrical impedance. However, the plasma salinity also affects the conductivity of the sample and therefore the impedance. By analyzing the relationship between the equivalent circuit components such as $C_S$ and $R_S$ under different conditions and finding different sets of parameters for different salinity levels, information on both hematocrit and salinity can be extracted from from a single impedance measurement.

According to various implementations, a reader described herein may be configured to provide both positive and negative pressure (vacuum) to a cartridge. Provided herein are systems that provide set pressure and vacuum levels. In some implementations, the set pressure level is greater than the set vacuum level. In some implementations, the reader includes check valves on the positive and negative sides of the pump. The cracking pressure of each check valve is set at the desired pressure or vacuum level to be supplied to the cartridge.

In some implementations, the reader includes a single pump pneumatic system configured to provide set pressure and vacuum levels. FIG. 9A shows a block diagram of a pneumatic system according to various implementations. Pump 901 can be, for example, a diaphragm pump or other appropriate pump. Pump 901 is connected to inlet air filter 903, a multivalve manifold 905, and two check valves 913 and 915. The multivalve manifold 905 is connected to a cartridge interface 911. Pressure is supplied to valves 917a-917g via line 925. Vacuum is supplied to valves 917a-917h via line 923. Valve 917h is connected to ambient (not shown) as well to vacuum line 923. In the example of FIG. 9A, the multivalve manifold 905 supplies pressure/vacuum to seven lines of the cartridge via cartridge interface 911 and supplies ambient/vacuum to one line of the cartridge via cartridge interface 911, however, according to various implementations, any number of valves and lines may be used to supply pressure and/or vacuum and/or ambient. In some implementations, a hydrophobic membrane may be disposed between the manifold 905 and cartridge interface 911 to provide a filter on each pneumatic line to the cartridge.

Check valve 913 has a cracking pressure Pv of the desired vacuum to be supplied to the system, and check valve 915 has a cracking pressure of the desired pressure Pp to be supplied to the system. Once turned on, pump 901 initially brings the vacuum down to Pv, moving air to the pressure side of the pump. Because Pv<Pp, this is insufficient to supply the desired pressure Pp. Accordingly, valve 913 on the vacuum side can be used to provide sufficient air to the pressure side. As noted above, the cracking pressure of valve 913 is Pv, such that air is drawn in through only when the vacuum pulled by pump 901 exceeds Pv. In this manner, when vacuum is input to the cartridge it is always at the desired level Pv once the system is operating at steady state. Valve 915 on the pressure side vents out excess air so that pressure is delivered to the cartridge at Pp. The pump reaches steady state 5-10 seconds after the system is turned on. At steady-state, vacuum supplied to the cartridge is a Pv and pressure supplied to the cartridge is at Pp. Because little volume is required to run the cartridge, the system generally continuously operates at steady-state.

In some implementations, one-way flow valves (not shown) on the input and output sides of the pump 901 also allow pressure and vacuum in the cartridge to be maintained while valves 917a-917h are held in place, allowing the pump to be turned off between switching of these valves. Once these valves are switched, e.g., to operate the microvalves or pumps on the cartridge, the pump 901 is turned on to bring the vacuum and pressure levels in the system to Pv and Pp, respectively.

As indicated above, Pv is less than Pp; in one example Pv may be 4.5 psig and Pp may be 7.5 psig. In some implementations, valves 917a-917h may be three-way valves. The pump capacity is such that Pp is less than the pump capacity P minus Pv. The above description allows a single motor single head diaphragm pump to generate set pressure and vacuum levels to a cartridge. Using a single pump and the above configuration can provide a cost effective and space efficient manner to provide set pressure and vacuum levels. In alternate implementations, two pumps or a single motor pump with two heads may be used. The pneumatic system may also include a pressure sensor 907 and a vacuum sensor 909. Microelectromechanical (MEMS) sensors may be used. In some implementations, readings from sensors 907 and 909 may be used as input signals to determine when to turn the pump on and off, if desired to reduce power consumption. The measurements 907 and 909 may also be used in quality control, with the reader monitoring.

In some implementations, the reader switches each of valves 917a-917h after the system is initially pressurized and confirms a characteristic drop in pressure detected by sensor 907 and/or a characteristic rise in pressure detected by sensor 909. Lack of characteristic drop/rise indicates that the valve has not switched, e.g., because it is stuck. This can be performed without a cartridge inserted to ensure that pneumatic assembly is working.

In implementations in which electrochemical sensing is used, the reader can include electronic hardware for running the electrochemical sensing on the cartridge. The measurement of current produced or consumed by electrochemical reactions can be done with a 3-electrode system. Such reactions can be used as the end-point detection for ELISA. In this configuration, a capture antibody is immobilized on a working electrode so that enzyme-labeled reported binds to the working electrode in a target-specific manner. Electrochemical current generated by the specific reaction enters the working electrode to be amplified by a current-to-voltage circuit. The output voltage is used to determine the amount of target present. The electrochemical reaction is often dependent on the electrical potential difference between the fluid and the working electrode. For reproducible current measurements, this electrical potential is maintained at a fixed value throughout the measurement period. The fluid potential is maintained by a potentiostat circuit. This circuit compares the measured potential of the fluid against the desired voltage set point. The circuit changes the voltage of the counter-electrode to maintain the fluid potential to the set point. The potentiostat often uses a third electrode, the reference electrode, as feedback to the control circuit. FIG. 9B shows a schematic example of a configuration including three working electrodes (WE0, WE1, and WE2), a counter electrode CE, a reference electrode RE, and current-to-voltage converters (C2V0, C2V1, and C2V2).

The fluid potential can be controlled by the input to the potentiostat amplifier. According to various implementations, the working electrode potential of each sensor may or may not be independently controllable. In some implementations, all or a subset of inputs 920, 921, and 922 of the C2V0, C2V1 and C2V2 amplifiers may be independently controllable. In some implementations, all or subset of these may be connected to ground. Independent control may be desirable, if for example, the voltage at which an enzymatic assay is performed at WE0 negatively affects the diffusion rates of analyte to WE1 and WE2 during ELISA incubation. In one example, WE0 can be at 300 mV to detect hydrogen peroxide, and WE1 at −300 mV to enhance diffusion of the target protein to be measured at WE1 to the electrode. In some other implementations, it may be simpler and effective to control only the fluid potential using input 901.

With reference to FIG. 9B, in some implementations, the system may include a second reference electrode that is used only to verify that reference electrode RE is working as part of quality control. Such a verification electrode may be placed at another point in the sensor well. A measured voltage that differs from the control voltage 901 would indicate a presence of a problem such as the potentiostat being defective, the reference electrodes being different, e.g., due to screen printing errors, or insufficient electrolytes in the system. Such an indication can cause the reader to provide the user with a notification that the cartridge is defective and should be replaced.

Figure 11B:
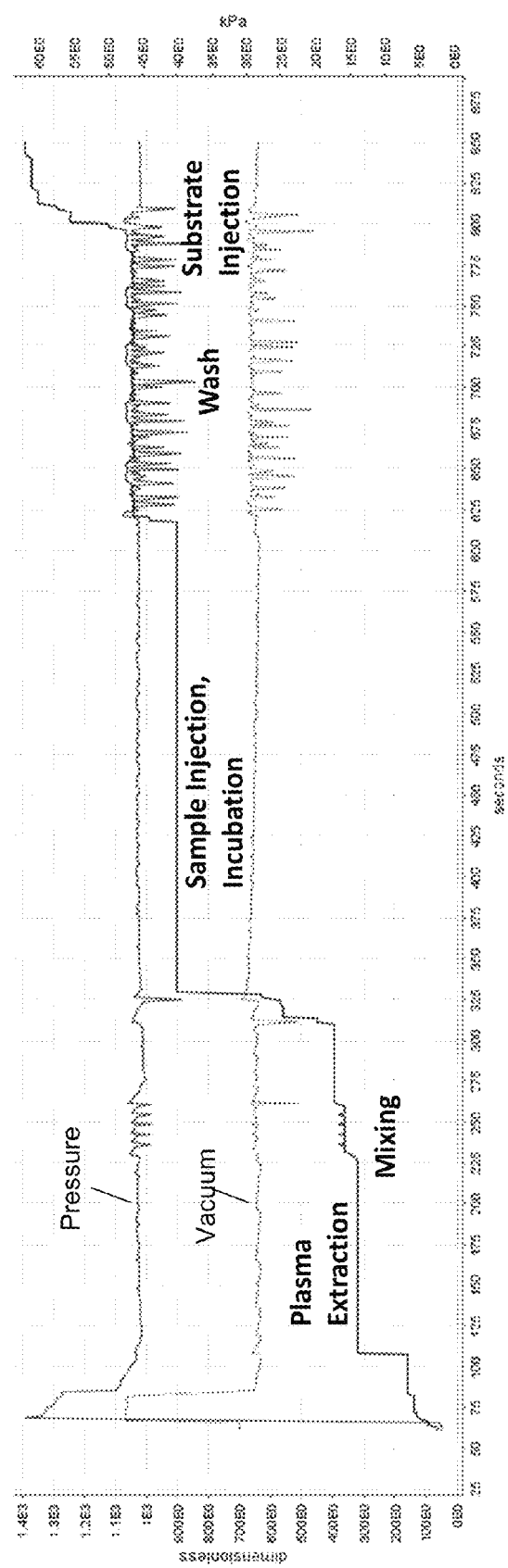
Figure 11C:
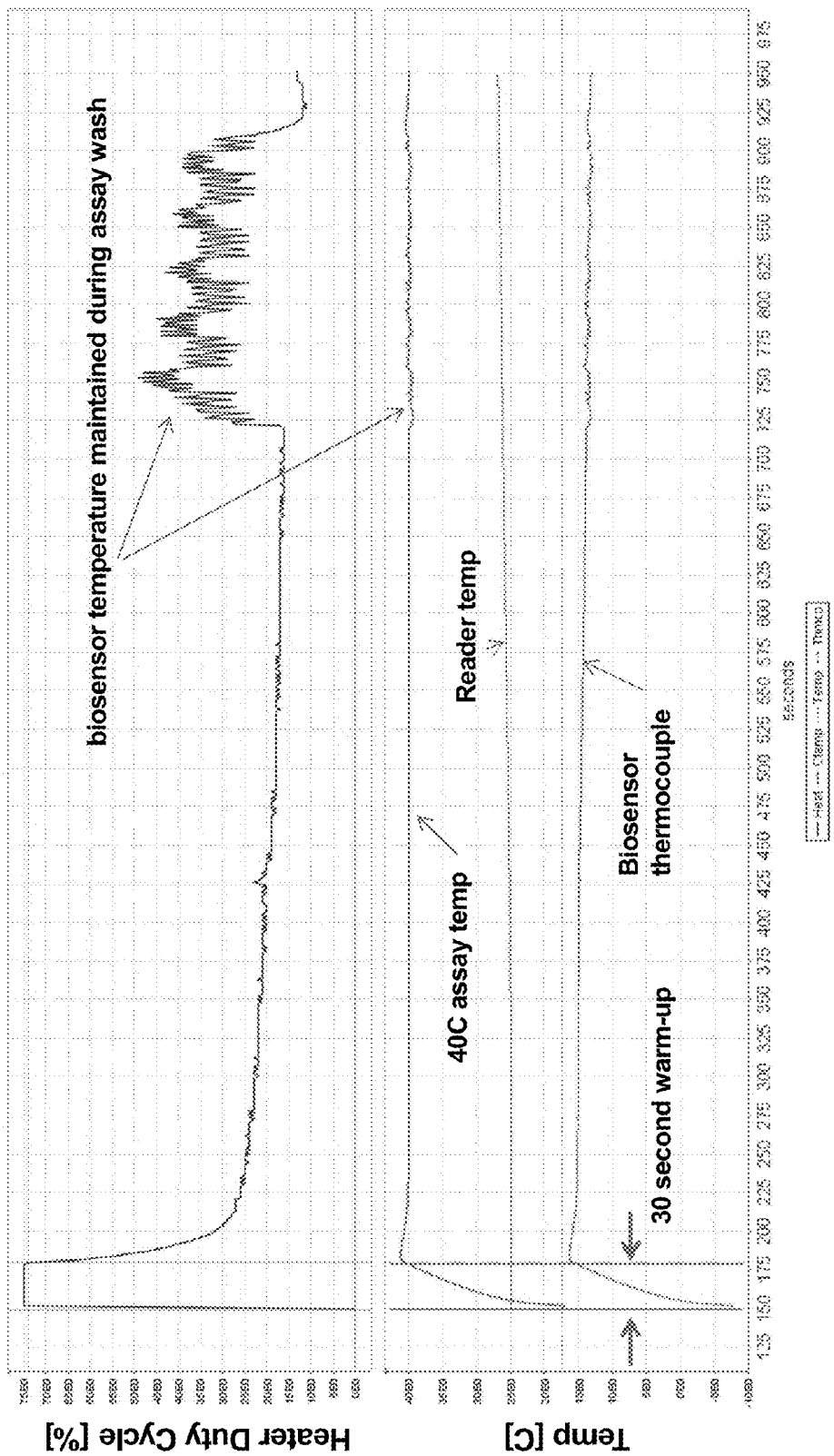

FIGS. 11A-11C show examples of sensor current, reader pressure and vacuum, and sensor temperature and heater duty cycle during operation. First, FIG. 11A shows current for substrate conductivity check, wash conductivity check, and five sensors in a sensor well. Line 11 represents the substrate conductivity check. See, e.g., substrate conductivity check 330 in FIG. 3. In the example of FIG. 11A, the substrate bag is punctured when the pump in the reader is turned on soon after the cartridge is inserted and the process initialized, showing a small amount of current. Line 12 represents current of the wash conductivity check. See, e.g., wash conductivity check 332 in FIG. 3, which has current when the wash bag is punctured and valve 367 is opened. The substrate and wash liquids are released and primed during plasma extraction and mixing phase of the process, as indicated in FIG. 11A. Five lines 13 represent the current from each of five sensors in the sensor well, e.g., as shown in FIG. 7A. Current spikes to about 2E3 nAmps at sample injection into the sensor well. Although difficult to see in the figure, the five lines are separated slightly in time as the fluid moves across the electrodes of each sensor. The sample incubates for about 5 minutes, as shown, followed by the injection of the wash fluid into the sensor well and washing. At 14, the substrate is injected to the sensor well, causing the current in the sensor well to drop.

FIG. 11B shows pressure and vacuum in the reader during operation. Pressure and vacuum remain fairly constant over the cycle, with fluctuations during mixing and washing due to valves (e.g., valves 917a-917h) switching to operate the microvalves and pumps on the cartridge. FIG. 11C shows heater duty cycle and various temperatures during operation. The assay temperature, derived from the screen-printed thermocouple temperature measurement, is maintained at 40° C. in this example, with feedback from the screen-printed thermocouple used to control duty cycle.

Figure 12A:
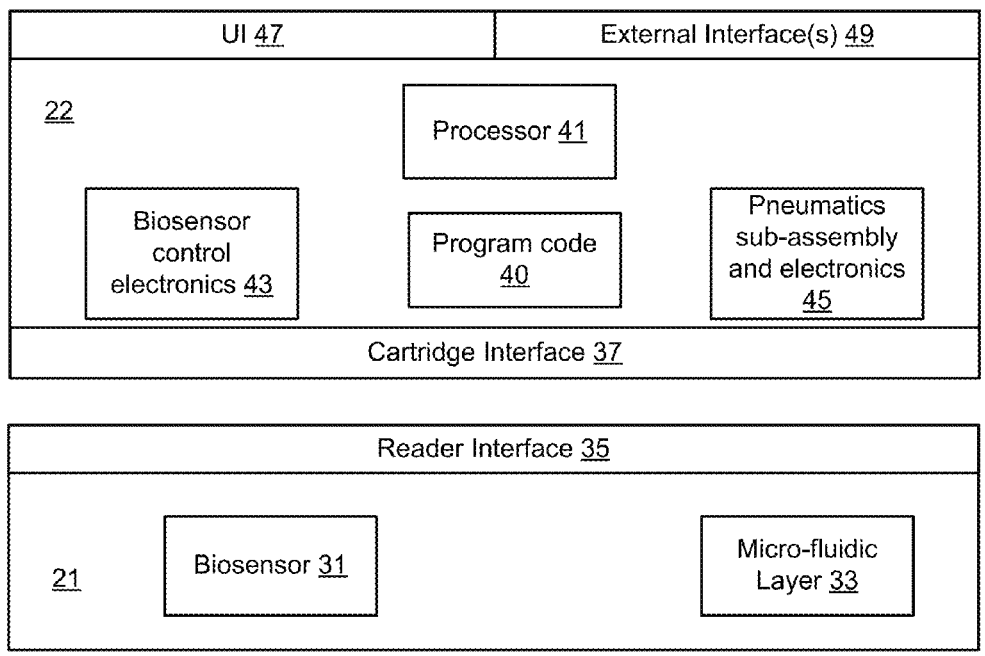
FIG. 12A shows a block diagram of an example of a reader and cartridge system that can be used in accordance with some implementations.
Figure 12B:
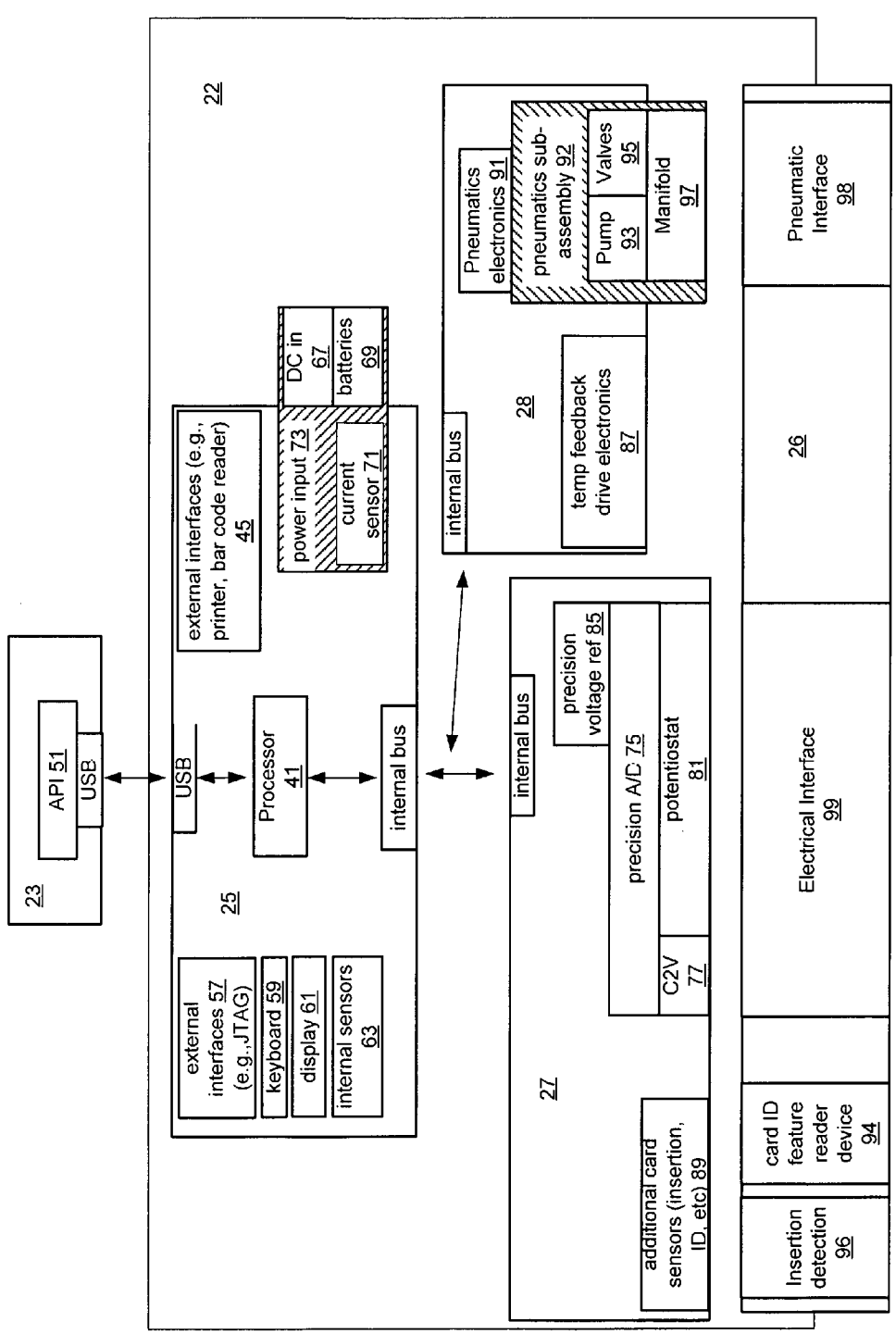
FIGS. 12B and 12C show block diagrams of examples of some implementations of elements of FIG. 12A and various possible interconnections between these elements
Figure 12C:
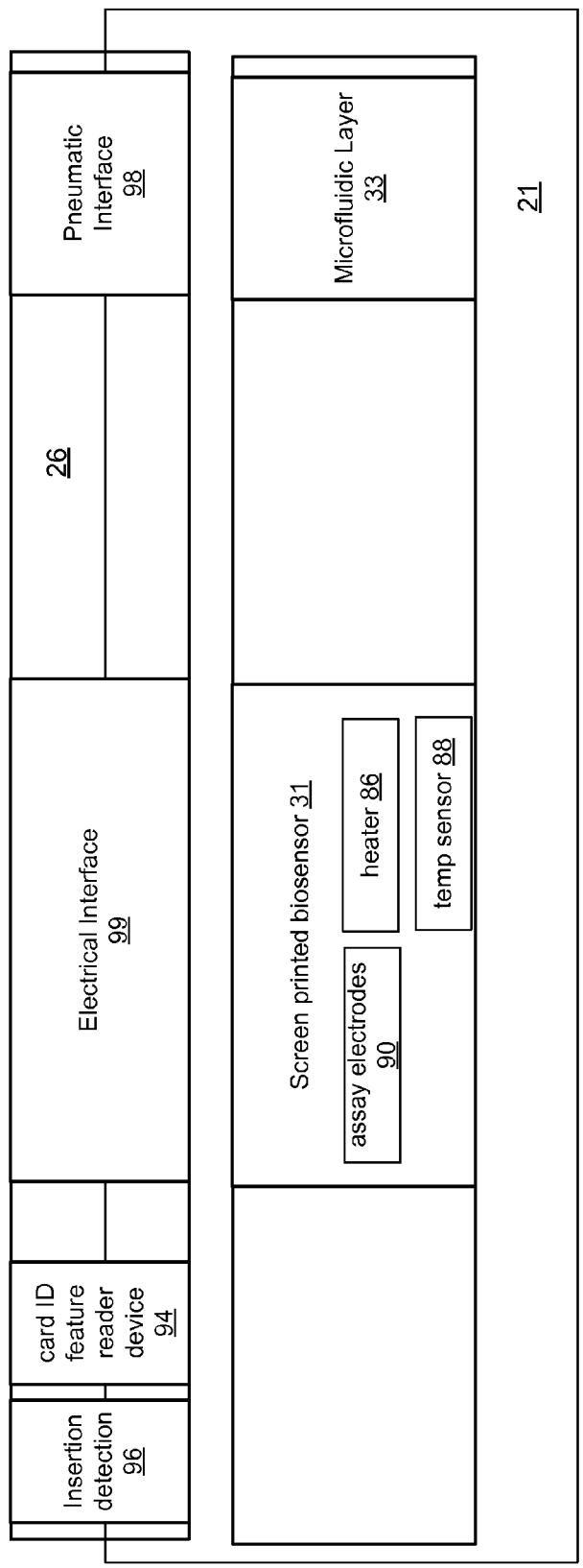

FIG. 12A shows a block diagram of an example of a reader and cartridge system that can be used in accordance with some implementations. FIGS. 12B and 12C show block diagrams of examples of some implementations of elements of FIG. 12A and various possible interconnections between these elements. Turning first to FIG. 12A, a reader 22 includes a processor 41, program code 40, a user interface 47, one or more additional interfaces 49 for external systems and/or devices, biosensor control electronics 43, and a pneumatics sub-assembly and electronics 45, and a cartridge interface 37.

The processor 41 can be one or more microprocessors having low power consumption, such as an ARM processor. Program code 40 implementing instructions for operating reader 22 may be, for example, software or firmware stored in any volatile or non-volatile memory medium or device, including flash memory, ROM or RAM, or provided on any media capable of storing program code, such as any type of rotating media including disks, magnetic or optical cards, nanosystems (including molecular memory ICs), or any other type of computer-readable medium or device suitable for storing instructions and/or data. Additionally, the entire program code, or portions thereof, may be transmitted and downloaded from a software source over a transmission medium to the reader 22. It will also be appreciated that computer code for the disclosed implementations can be realized in any programming language such as, for example, C, C++, and many other programming languages as are known may be used.

User interface 47 typically includes a display (e.g., a monitor screen, LCD display, etc.) and one or more user input devices, such as a keyboard, touch pad, touch screen, pen or the like, for interacting with the reader. External interface(s) 49 can include interfaces to one or more external systems and/or devices, including JTAG interfaces, USB interfaces and the like.

Biosensor control electronics 43 can include circuitry to control assay parameters, e.g., voltage of assay electrodes for an electrochemical assay, assay temperature, and the like. Pneumatics sub-assembly and electronics 45 can include one or more pumps, lines, and valves configured to supply pressure and vacuum to the microfluidic layer 33 of the cartridge 21 and related electronics. The cartridge interface 37 is configured to provide electrical and pneumatic connection to reader interface 35 of cartridge 21. For example, cartridge interface 37 of reader 22 can include contact pads and pneumatic lines configured to connect to corresponding conductive traces and pneumatic ports on the cartridge 21.

In addition to reader interface 35, cartridge 21 includes biosensor 31, which can receive and provide electrical signals from or to the reader via reader interface 35, and microfluidic layer 33, which can receive pressure and vacuum inputs from the reader via reader interface 35.

FIGS. 12B and 12C show block diagrams of examples of some implementations of elements of FIG. 12A and various possible interconnections between these elements. First, turning to FIG. 12B, external system 23, reader 22, and reader/cartridge interface 26 are shown. Several elements in the shown in FIGS. 12A and 12B include conventional, well-known elements that are explained only briefly here. External system 23 can be, for example, a personal computer, workstation, tablet, or any other computing system or device capable of interfacing directly with the reader 22. In the example of FIG. 12B, external system 23 includes an Application Program Interface (API) 51 which can provides an application programmer interface to processes resident on reader 22. Also, in the example of FIG. 12B, the external system 23 is shown connected to reader 22 via a USB connection. In other implementations, it can connect directly or indirectly to the reader 22 via any type of network connection (e.g., the Internet) or non-network connection, wired or wireless (e.g. via Bluetooth or WiFi). Reader 22 is portable and it is generally contemplated that the reader 22 is unconnected to external system 23 while in use. For example, reader 22 may be carried and used in a hospital or field setting by a doctor or other operator unconnected to external system 23. In some implementations, however, reader 22 may be connected to external system 23, for example to transfer data, update program code and the like.

In the example of FIG. 12B, reader 22 includes a main board 25, daughter board 27, and valve interface board 28. In the example of FIG. 12B, main board 25 includes external interfaces 57 including, for example, JTAG pins, a keyboard 59 for a user to key in commands or respond to prompts, a display 61 configured to display a user menus, instructions, prompts and/or assay results, and external interfaces 45 for printers, bar code readers, and/or other devices. Reader 22 also includes power input 73, which can be configured to receive a DC in plug 67 and/or batteries 69. Power input 73 can include current sensor 71. Internal sensors 63 may be included on main board 22 to monitor temperature and other conditions.

In the example of FIG. 12B, main board 25 is connected to daughter board 27 via an internal bus. Daughter board 27 can include electronic for control of the assay, including current-to-voltage converters 77, a potentiostat 81, precision A/D converter 81 to digitize the current and voltage signals, and precision voltage reference 85. Daughter board 27 may also include additional sensors 89 to detect insertion, cartridge identification, etc. Main board 25 is also connected to valve interface board 28, which includes pneumatics electronics 91 and the temperature feedback drive electronics 87. Pneumatics electronics 91 interface with pneumatics sub-assembly 92, which includes pump 93, valves 95 and manifold 97. One example of a pneumatics sub-assembly is described with reference to FIG. 9A.

FIGS. 12B and 12C also depict cartridge/reader interface 26, including electrical interface 99 to connect the assay control electronics with the biosensor 31 (shown in FIG. 12C), pneumatic interface 98 to connect the pneumatics sub-assembly with the microfluidic layer 33 (shown in FIG. 12C), insertion detection 96 and card identification 94 as discussed above. FIG. 12C depicts cartridge 21, which includes biosensor 31. In the example of FIG. 12C, biosensor 31 is a screen printed biosensor 31, for example, as described above with respect to FIG. 7A. Biosensor 31 includes assay electrodes 90, a heater 86, and a temperature sensor 88. The cartridge also includes microfluidic layer 33. An example of a microfluidic layer is described above with respect to FIGS. 4A-4H.

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

The invention claimed is:

1. A cartridge for sensing one or more analytes in a sample, the cartridge comprising:
 a sample inlet chamber for receiving a sample;
 a reagent chamber configured to store a solid phase reagent;
 a mixing circuit connected to the sample inlet chamber and comprising a mixing chamber and the reagent chamber;
 one or more sensors; and
 a detection channel providing a flow path over the one or more sensors, wherein the cartridge includes at least two sensors and is configured to perform non-capture electrochemical enzymatic sensing and electrochemical enzyme-linked immunosorbent assay (ELISA) sensing on a single sample.

2. The cartridge of claim 1, further comprising a de-bubbling channel disposed between the reagent chamber and the detection channel and configured to vent out bubbles in the sample.

3. The cartridge of claim 2, wherein the mixing circuit comprises the de-bubbling channel.

4. The cartridge of claim 2, wherein the de-bubbling channel is external to the mixing circuit.

5. The cartridge of claim 4, further comprising a buffer zone between the reagent chamber and the de-bubbling channel.

6. The cartridge of claim 2, wherein the de-bubbling channel is covered by a hydrophobic membrane.

7. The cartridge of claim 1, further comprising one or more puncture-able compartments containing liquid reagents.

8. The cartridge of claim 7, further comprising puncture mechanisms configured to puncture the puncture-able compartments.

9. The cartridge of claim 8, wherein the puncture mechanisms are configured to be pneumatically actuated.

10. The cartridge of claim 1, further comprising a screen-printed heater configured to heat the detection channel.

11. The cartridge of claim 1, further comprising a screen-printed thermocouple.

12. The cartridge of claim 1, wherein the cartridge is configured to receive only pneumatic and electric inputs from a reader.

13. The cartridge of claim 1, further comprising a microfluidic layer, the microfluidic layer comprising the reagent chamber, mixing chamber, and the detection channel.

14. The cartridge of claim 1, further comprising a sensing assembly including screen-printed electrodes, the one or more sensors including the screen-printed electrodes.

15. The cartridge of claim 1, further comprising a plasma filtration membrane.

16. The cartridge of claim 15, further comprising a vacuum line connected to the plasma filtration membrane.

17. The cartridge of claim 1, wherein all liquid movement within the cartridge is pneumatically actuated.

18. The cartridge of claim 1, further comprising a plurality of fluid stops connected to a hydrophobic membrane.

19. The cartridge of claim 1, wherein each of the two sensors is configured to sense a different cardiac-related biomarker.

20. The cartridge of claim 1, wherein each of the two sensors is configured to sense a different biomarker for traumatic brain injury.

21. A cartridge for sensing first and second target analytes in a biological sample, comprising:
 a first working electrode coated with one or more enzymes configured to react with a first target analyte to directly or indirectly produce a first electrochemical signal; and
 a second working electrode having capture species attached thereto, the capture species configured to capture the second target analyte to directly or indirectly produce a second electrochemical signal,
wherein the cartridge is a single sample, single use, disposable cartridge.

22. The cartridge of claim 21, wherein the first working electrode and the second working electrode are carbon-based electrodes.

23. The cartridge of claim 21, wherein the first target analyte is lactate and the second target analyte is procalcitonin (PCT) or C-reactive protein (CRP).

24. The cartridge of claim 21, wherein at least one of the first target analyte and the second target analyte is a biomarker for sepsis selected from the group consisting of:
CRP, PCT, IL-6, lactate, endotoxin, and 1-3 beta glucan.

25. The cartridge of claim 21, wherein the first and second target analytes include two or more biomarkers for sepsis selected from the group consisting of: CRP, PCT, IL-6, lactate, endotoxin, and 1-3 beta glucan.

26. The cartridge of claim 21, wherein the first target analyte is creatinine and the second target analyte is a cardiac troponin.

27. The cartridge of claim 26, wherein the cardiac troponin is cardiac troponin I.

28. The cartridge of claim 21, wherein the first and second target analytes include two or more cardiac related biomarkers selected from the group consisting of a cardiac troponin, myoglobin, fatty acid binding protein, D-dimer, brain natriuretic peptide, creatine kinase-MB, and creatinine.

29. The cartridge of claim 28, wherein the cardiac troponin is cardiac troponin I.

30. The cartridge of claim 21, wherein at least one of the first and second target analytes is a traumatic brain injury biomarker.

31. The cartridge of claim 21, wherein the first target analyte is selected from the group consisting of for glucose, galactose, lactose, glutamic acid, cholesterol, xanthine, hypoxanthine, uric acid, choline, creatinine, acetylcholine, tyrosine, and hydrogen peroxide.

32. The cartridge of claim 21, wherein the one or more enzymes comprise one or more of an oxidase, an esterase, uricase, and a kinase.

33. The cartridge of claim 21, wherein the first working electrode coated with one or more enzymes is further coated with a water-soluble polymer.

34. The cartridge of claim 21, wherein the first working electrode is further coated with one or more mediators.

35. The cartridge of claim 21, wherein the first working electrode and the second working electrode are in a detection channel on the cartridge, the detection channel having a sample inlet and wherein the second working electrode is closer to the sample inlet than the first working electrode is to the sample inlet.

36. The cartridge of claim 21, further comprising an additional working electrode configured to produce a control electrochemical signal.

37. The cartridge of claim 21, further comprising an additional working electrode configured to react with or capture the third target analyte to directly or indirectly produce a third electrochemical signal.

38. A reader configured to detect bubbles on a sensor of a cartridge comprising:
an interface for receiving the cartridge; and
computer readable media including instructions to:
measure the impedance of a sensor well on the cartridge;
determine the series resistance Rs and the series capacitance Cs of an equivalent circuit;
determine if a relationship between series resistance Rs and the series capacitance Cs meets a specified criteria; and
based on the determination of the relationship, determine whether a bubble is detected.

39. The reader of claim 38, wherein the specific criteria is based on parameters k0, k1, $\epsilon$, and $\epsilon max$, wherein $\epsilon$ is an error, $\epsilon max$ is a maximum acceptable error, and k0 and k1 are experimentally established parameters following the linear relationship $Cs = k0+k1*Rs+\epsilon$ and $|Cs-k0-k1*Rs| \leq \epsilon max$.

40. A cartridge for sensing one or more analytes in a sample, the cartridge comprising:
a sample inlet chamber for receiving a sample;
a reagent chamber configured to store a solid phase reagent;
a mixing circuit connected to the sample inlet chamber and comprising a mixing chamber and the reagent chamber;
one or more sensors; and
a detection channel providing a flow path over the one or more sensors, wherein the cartridge is configured to receive only pneumatic and electric inputs from a reader.

41. The cartridge of claim 40, further comprising a de-bubbling channel disposed between the reagent chamber and the detection channel and configured to vent out bubbles in the sample.

42. The cartridge of claim 40, further comprising one or more puncture-able compartments containing liquid reagents, and one or more pneumatically-actuatable puncture mechanisms.

43. The cartridge of claim 40, further comprising a screen-printed heater configured to heat the detection channel.

44. The cartridge of claim 40, further comprising a screen-printed thermocouple.

45. The cartridge of claim 40, further comprising a microfluidic layer, the microfluidic layer comprising the reagent chamber, mixing chamber, and the detection channel.

46. The cartridge of claim 40, further comprising a sensing assembly including screen-printed electrodes, the one or more sensors including the screen-printed electrodes.

47. The cartridge of claim 40, further comprising a plasma filtration membrane.

48. A cartridge for sensing one or more analytes in a sample, the cartridge comprising:
a sample inlet chamber for receiving a sample;
a reagent chamber configured to store a solid phase reagent;
one or more sensors;
a detection channel providing a flow path over the one or more sensors;
a de-bubbling channel disposed between the reagent chamber and the detection channel and configured to vent out bubbles in the sample; and
a mixing circuit connected to the sample inlet chamber and comprising a mixing chamber, the de-bubbling channel, and the reagent chamber.

49. A cartridge for sensing one or more analytes in a sample, the cartridge comprising:
a sample inlet chamber for receiving a sample;
a plasma filtration membrane;
a vacuum line connected to the plasma filtration membrane;
a reagent chamber configured to store a solid phase reagent;

a mixing circuit connected to the sample inlet chamber and comprising a mixing chamber and the reagent chamber;

one or more sensors; and a detection channel providing a flow path over the one or more sensors.

50. The cartridge of claim 49, further comprising a de-bubbling channel disposed between the reagent chamber and the detection channel and configured to vent out bubbles in the sample.

51. The cartridge of claim 49, further comprising one or more puncture-able compartments containing liquid reagents, and one or more pneumatically-actuatable puncture mechanisms.

52. The cartridge of claim 49, further comprising a screen-printed heater configured to heat the detection channel.

53. The cartridge of claim 49, further comprising a screen-printed thermocouple.

54. The cartridge of claim 49, wherein the cartridge is configured to receive only pneumatic and electric inputs from a reader.

55. The cartridge of claim 49, further comprising a de-bubbling channel disposed between the reagent chamber and the detection channel and configured to vent out bubbles in the sample.

56. The cartridge of claim 55, wherein the mixing circuit comprises the de-bubbling channel.

57. The cartridge of claim 55, wherein the de-bubbling channel is external to the mixing circuit.

58. The cartridge of claim 49, further comprising a microfluidic layer, the microfluidic layer comprising the reagent chamber, mixing chamber, and the detection channel.

59. The cartridge of claim 49, further comprising a sensing assembly including screen-printed electrodes, the one or more sensors including the screen-printed electrodes.

60. A cartridge for sensing one or more analytes in a sample, the cartridge comprising:
   a sample inlet chamber for receiving a sample;
   a reagent chamber configured to store a solid phase reagent;
   a mixing circuit connected to the sample inlet chamber and comprising a mixing chamber and the reagent chamber;
   one or more sensors;
   a detection channel providing a flow path over the one or more sensors; and
   a de-bubbling channel disposed between the reagent chamber and the detection channel and configured to vent out bubbles in the sample, wherein the de-bubbling channel is covered by a hydrophobic membrane.

61. The cartridge of claim 60, wherein the de-bubbling channel is external to the mixing circuit.

62. A cartridge for sensing one or more analytes in a sample, the cartridge comprising:
   a sample inlet chamber for receiving a sample;
   a reagent chamber configured to store a solid phase reagent;
   a mixing circuit connected to the sample inlet chamber and comprising a mixing chamber and the reagent chamber;
   one or more sensors;
   a detection channel providing a flow path over the one or more sensors; and
   a plurality of fluid stops connected to a hydrophobic membrane.

63. The cartridge of claim 1, wherein each of the two sensors is configured to sense a different biomarker for sepsis.

64. The cartridge of claim 63, wherein the biomarkers for sepsis are selected from the group consisting of CRP, PCT, IL-6, lactate, endotoxin, and 1-3 beta glucan.

65. The cartridge of claim 9, wherein the cardiac-related biomarkers are selected from the group consisting of a cardiac troponin, myoglobin, fatty acid binding protein, D-dimer, brain natriuretic peptide, creatine kinase-MB, and creatinine.

* * * * *